US012653848B2

(12) United States Patent
De Vos et al.

(10) Patent No.: US 12,653,848 B2
(45) Date of Patent: Jun. 16, 2026

(54) FECAL MATTER FOR PREVENTING OR TREATING INTESTINAL MICROBIOME ABERRATIONS IN CESAREAN SECTION-BORN INFANTS

(71) Applicant: CAELUS PHARMACEUTICALS B.V., Zegveld (NL)

(72) Inventors: Willem Meindert De Vos, Amsterdam (NL); Lucas Gerardus Willibrordus Sterkman, Heiloo (NL)

(73) Assignee: CAELUS PHARMACEUTICALS B.V., Zegveld (NL)

( * ) Notice: Subject to any disclaimer, the term of this patent is extended or adjusted under 35 U.S.C. 154(b) by 515 days.

(21) Appl. No.: 18/246,495

(22) PCT Filed: Sep. 24, 2021

(86) PCT No.: PCT/EP2021/076348
§ 371 (c)(1),
(2) Date: Mar. 23, 2023

(87) PCT Pub. No.: WO2022/063980
PCT Pub. Date: Mar. 31, 2022

(65) Prior Publication Data
US 2023/0364164 A1 Nov. 16, 2023

(30) Foreign Application Priority Data
Sep. 25, 2020 (NL) ...................................... 2026545

(51) Int. Cl.
*A61K 35/745* (2015.01)
*A61K 35/24* (2015.01)
*A61P 1/00* (2006.01)

(52) U.S. Cl.
CPC ............ *A61K 35/745* (2013.01); *A61K 35/24* (2013.01); *A61P 1/00* (2018.01)

(58) Field of Classification Search
None
See application file for complete search history.

(56) References Cited

FOREIGN PATENT DOCUMENTS

WO 2016/183535 A1 11/2016

OTHER PUBLICATIONS

Bibbo et al., "Fecal Microbiota Transplantation: Screening and Selection to Choose the Optimal Donor", J. Clin. Med., vol. 9, No. 6, (Jun. 5, 2020), p. 1757.

Brunse et al., "Effect of fecal microbiota transplantation route of administration on gut colonization and host response in preterm pigs", The ISME Journal, vol. 13, No. 3, (Oct. 26, 2018), pp. 720-733.
Helve et al., 2843. Maternal Fecal Transplantation to Infants Born by Cesarean Section: Safety and Feasibility, Open Forum Infect. Dis., vol. 6, No. S2, (Oct. 1, 2019), p. S68.
International Search Report for International Application No. PCT/EP2021/076348, mailed Dec. 22, 2021, 6 pages.
International Written Opinion for International Application No. PCT/EP2021/076348, mailed Dec. 22, 2021, 6 pages.
Naito et al., "A next-generation beneficial microbe: Akkermansia muciniphila", J. Clin. Biochem. Nutr., vol. 63, No. 1, (Jan. 1, 2018), pp. 33-35.
Rinninella et al., "What is the Healthy Gut Microbiota Composition? A Changing Ecosystem across Age, Environment, Diet, and Diseases", Microorganisms, vol. 7, No. 1, (Jan. 10, 2019), p. 14.
De Koff et al. "Mode of delivery modulates the intestinal microbiota and impacts the response to vaccination" Article, Nature Communications 13, 6638 (Nov. 15, 2022) 12 pages.
Andersen et al. "Caesarean delivery and risk of chronic inflammatory diseases (Inflammatory Bowel Disease, Rheumatoid Arthritis, Coeliac Disease, and Diabetes Mellitus): A population-based registry study of 2,699,479 births in Denmark during 1973-2016" Clin. Epidemiol. 12:287-293 (Mar. 9, 2020).
Dominguez-Bellow et al. "Partial restoration of the microbiota of cesarean-born infants via vaginal microbial transfer" Nature Med. 22:250-3 (Feb. 1, 2016).
Gensollen et al. "How colonization by microbiota in early life shapes the immune system" Science 352, 539-544 (Apr. 29, 2016).
Korpela et al. "Fucosylated oligosaccharides in mother's milk alleviate the effects of caesarean birth on infant gut microbiota" Sci. Rep. 8:13757 (Sep. 13, 2018).
Korpela et al. "Intestinal microbiome is related to lifetime antibiotic use in Finnish pre-school children" Nature Comm. 7:10410 (Jan. 26, 2016).
Korpela et al. "Selective maternal seeding and environment shape the human gut microbiome" Genome Res. 28:561-568 (Apr. 28, 2018).
Shao et al. "Stunted microbiota and opportunistic pathogen colonization in caesarean-section birth" Nature 574:117-121 (Oct. 2019).

*Primary Examiner* — Michelle F. Paguio Frising
(74) *Attorney, Agent, or Firm* — TraskBritt

(57) ABSTRACT

A composition for use in the prevention or treatment of intestinal microbiota aberration in a Cesarean section- (CS-) born infant, wherein the use is particularly for one or more of reducing intestinal colonization of pathogenic microorganisms, increasing intestinal relative abundance of *Bacteroides* species and/or *Bifidobacterium* species, increasing intestinal microbial diversity, increasing level of intestinal secretory IgA and/or intestinal antimicrobial peptides, reducing susceptibility to a disorder particularly chosen from the group consisting of metabolic disease, obesity, type 2 diabetes, auto-immune disease, atopy-related disease, allergy and asthma, and increasing immune response to vaccines.

23 Claims, 5 Drawing Sheets

Specification includes a Sequence Listing.

SEQUENCE LISTING

```
<160> NUMBER OF SEQ ID NOS: 17

<210> SEQ ID NO 1
<211> LENGTH: 1533
<212> TYPE: DNA
<213> ORGANISM: Bacteroides vulgatus
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
```

```
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (1204)..(1204)
<223> OTHER INFORMATION: n is a, c, g, or t
<220> FEATURE:
<221> NAME/KEY: misc_feature
<222> LOCATION: (1255)..(1255)
<223> OTHER INFORMATION: n is a, c, g, or t
<220> FEATURE:
<221> NAME/KEY: misc_feature
<222> LOCATION: (1499)..(1499)
<223> OTHER INFORMATION: n is a, c, g, or t
<220> FEATURE:
<221> NAME/KEY: misc_feature
<222> LOCATION: (1510)..(1518)
<223> OTHER INFORMATION: n is a, c, g, or t

<400> SEQUENCE: 1
tattacaatg aagagtttga tcctggctca ggatnaacgc tagctacagg cttaacacat      60
gcaagtcgag gggcagcatg gtcttagctt gctaagncna tggcgaccgg cgcacgggtg     120
agtaacacgt atccaacctg ccgtctactc ttggacagcc ttctgaaagg aagattaata     180
caagatggca tcatgagtcc gcatgttcac atgattaaag gtattccggt agacgatggg     240
gatgcgttcc attagatagt aggcggggta acggcccacc tagtcttcga tggatagggg     300
ttctgagagg aaggtccccc acattggaac tgagacacgg tccaaactcc tacgggaggc     360
agcagtgagg aatattggtc aatgggcgag agccngaacc agccaagtag cgtgaaggat     420
gactgcccta tgggttgtaa acttcttta taaaggaata aagtcgggta tggatacccg     480
nttgcatgta ctttatgaat aaggatcggc taactccgtg ccagcagccg cggtaatacg     540
gagnatccga gcgttatccg gatttattgg gtttaaaggg agcgtagatg gatgtttaag     600
tcagttgtga aagtttgcgg ctcaaccgta aaattgcagt tgatactgga tatcttgagt     660
gcagttgagc aggcggaat tcgtggtgta gcggtgaaat gcttagatat cacgaagaac     720
tccgattgcg aaggcagcct gctnagctgc aactgacatt gaggctcgaa agtgtgggta     780
tcaaacagga ttagatacc tggtagtcca cacggtaaac gatgaatact cgctgtttgc     840
gatatactgc aagcggccaa gcgaaagcgt taagtattcc acctggggag tacgccggca     900
acggtgaaac tcaaaggaat tgacgggggc cngcacaagc ggaggaacat gtggtttaat     960
tcgatgatac gcgaggaacc ttacccgggc ttaaattgca gatgaattac ggtgaaagcc    1020
gtaagccgca aggcatctgt gaaggtgctg catggttgtc gtcagctcgt gccgtgaggt    1080
gtcggcttaa gtgccataac gagcgcaacc cttgttgtca gttactaaca ggttatgctg    1140
aggactctga caagactgcc atcgtaagat gtgaggaagg tggggatgac gtcaaatcag    1200 cacngcccctt acgtccgggg ctacacacgt gttacaatgg ggggtacaga gggcngctac    1260
cacgcgagtg gatgccaatc cccaaaacct ctctcagttc ggactggagt ctgcaacccg    1320
actccacgaa gctggattcg ctagtaatcg cgcatcagcc acggcgcggt gaatacgttc    1380
ccgggccttg tacacaccgc ccgtcaagtc atgggagccg ggggtacctg aagtgcgtaa    1440
ccgcgaggag cgccctaggg taaaactggt gactgggggct aagtcgtaac aaggtagcng    1500
taccggaagn nnnnnnnnga acacctcctt tct                                 1533

<210> SEQ ID NO 2
<211> LENGTH: 1475
<212> TYPE: DNA
<213> ORGANISM: Bacteroides thetaiotaomicron
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (1274)..(1274)
<223> OTHER INFORMATION: n is a, c, g, or t
<220> FEATURE:
<221> NAME/KEY: misc_feature
<222> LOCATION: (1405)..(1405)
<223> OTHER INFORMATION: n is a, c, g, or t
<220> FEATURE:
<221> NAME/KEY: misc_feature
<222> LOCATION: (1412)..(1412)
<223> OTHER INFORMATION: n is a, c, g, or t

<400> SEQUENCE: 2
cantgaagag tttgatcctg gctcaggatn aacgctagct acaggcttaa cacatgcaag      60
tcgaggggca gcatttcnnt ttgcttgcaa actnnagatg gcgaccggcg cacgggtgag     120
taacacgtat ccaacctgcc gataactcgg ggatagcctt tcgaaagaaa gattaatacc     180
cgatggcata atcanaccgc atggtcttat tattaaagaa tttcggttat cgatggggat     240
gcgttccatt aggcagttgg tgaggtaacg gctcacnaaa ccttcgatgg ataggggttc     300
tgagaggaag gtcccccaca ttggaactga gacacggtcc naactcctac gggaggcagc     360
agtgaggaat attggtcaat gggcgcaggc ctnaaccagc caagtagcgt gaaggatgac     420
tgccctatgg gttgtaaact nctnttatat gggaataaag tnttccacgt gtggaatttt     480
```

```
gtatgtacca tatgaataag gatcggctaa ctccgtgcca gcagccgcgg tnatacggag   540
gatccgagcg ttatccggat ttattgggtt taaagggagc gtaggtggac agttaagtca   600
gttgtgaaag tttgcggctc aaccgtaaaa ttgcagttga tactggctgt cttgagtaca   660
gtagaggtgg gcggaattcg tggtgtagcg gtgaaatgct tagatatcac gaagaactcc   720
gattgcgaag gcagctcact ggactgcaac tgacactgat gctcgaaagt gtgggtatca   780
aacaggatta gataccctgg tagtccacac agtaaacgat gaatactcgc tgtttgcgat   840
atacagtaag cggccaagcg aaagcattaa gtattccacc tggggagtac gccggcaacg   900
gtgaaactca aaggaattga cggggqcccg cacaagcgga ggaacatgtg gtttaattcg   960
atgatacgcg aggaacctta cccgggctta aattgcattt gaataatctg gaaacaggtt   1020
agccgcaagg caaatgtgaa ggtgctgcat ggttgtcgtc agctcgtgcc gtgaggtgtc   1080
ggcttaagtg ccataacgag cgcaacccct atctttagtt actaacaggt catgctgagg   1140
actctagaga gactgccgtc gtaagatgtg aggaaggtgg ggatgacgtc aaatcagcac   1200
ggcccttacg tccgggccta cacacgtgtt acaatggggg gtacagaagg cagctacctg   1260
gtgacaggat gctnatccca aaagcctctc tcagttcgga tcgaagtctg caacccgact   1320
tcgtgaagct ggattcgcta gtaatcgcgc atcagccatg gcgcggtgaa tacgttcccg   1380
ggccttgtac acaccgcccg tcaanccatg anagccgggg gtacctgaag tacgtaaccg   1440
caaggagcgt cctagggtaa aactggtaat tggggg                              1475
```

```
<210> SEQ ID NO 3
<211> LENGTH: 1533
<212> TYPE: DNA
<213> ORGANISM: Bacteroides fragilis

<400> SEQUENCE: 3
```

```
ttacaacgaa gagtttgatc ctggctcagg atgaacgcta gctacaggct taacacatgc    60
aagtcgaggg gcatcaggaa gaaagcttgc tttctttgct ggcgaccggc gcacgggtga   120
gtaacacgta tccaacctgc cctttactcg gggatagcct ttcgaaagaa agattaatac   180
ccgatagcat aatgattccg catggtttca ttattaaagg attccggtaa aggatgggga   240
tgcgttccat taggttgttg gtgaggtaac ggctcaccaa gccttcgatg gatagggtt    300 ctgagaggaa ggtcccccac attggaactg agacacggtc caaactccta cgggaggcag   360
cagtgaggaa tattggtcaa tgggcgctag cctgaaccag ccaagtagcg tgaaggatga   420
aggctctatg ggtcgtaaac ttcttttata taagaataaa gtgcagtatg tatactgttt   480
tgtatgtatt atatgaataa ggatcggcta actccgtgcc agcagccgcg gtaatacgga   540
ggatccgagc gttatccgga tttattgggt ttaaagggag cgtaggtgga ctggtaagtc   600
agttgtgaaa gtttgcggct caaccgtaaa attgcagctg atactgtcag tcttgagtac   660
agtagaggtg ggcggaattc gtggtgtagc ggtgaaatgc ttagatatca cgaagaactc   720
cgattgcgaa ggcagctcac tggactgcaa ctgacactga tgctcgaaag tgtgggtatc   780
aaacaggatt agatacctg gtagtccaca cagtaaacga tgaatactcg ctgtttgcga   840
tatacagtaa gcggccaagc gaaagcatta agtattccac ctggggagta cgccggcaac   900
ggtgaaactc aaaggaattg acggggqccc gcacaagcgg aggaacatgt ggtttaattc   960
gatgatacgc gaggaacctt acccgggctt aaattgcagt ggaatgatgt ggaaacatgt   1020
cagtgagcaa tcaccgctgt gaaggtgctg catggttgtc gtcagctcgt gccgtgaggt   1080
gtcggcttaa gtgccataac gagcgcaacc cttatcttta gttactaaca ggttatgctg   1140
```

-continued

```
aggactctag agagactgcc gtcgtaagat gtgaggaagg tgggggatgac gtcaaatcag      1200 cacggcccctt acgtccgggg ctacacacgt gttacaatgg ggggtacaga aggcagctag      1260
cgggtgaccg tatgctaatc ccaaaatcct ctctcagttc ggatcgaagt ctgcaacccg      1320
acttcgtgaa gctggattcg ctagtaatcg cgcatcagcc acggcgcggt gaatacgttc      1380
ccgggccttg tacacaccgc ccgtcaagcc atgggagccg ggggtacctg aagtacgtaa      1440
ccgcaaggat cgtcctaggg taaaactggt gactgggggct aagtcgtaac aaggtagccg      1500
taccggaagg tgcggctgga acacctcctt tct                                   1533
```

<210> SEQ ID NO 4
<211> LENGTH: 1422
<212> TYPE: DNA
<213> ORGANISM: Bacteroides caccae
<220> FEATURE:
<221> NAME/KEY: misc_feature
<222> LOCATION: (179)..(181)
<223> OTHER INFORMATION: n is a, c, g, or t
<220> FEATURE:
<221> NAME/KEY: misc_feature
<222> LOCATION: (901)..(901)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1420)..(1420)
<223> OTHER INFORMATION: n is a, c, g, or t

<400> SEQUENCE: 4

```
atgaacgcta gctacaggct taacacatgc aagtcgaggg gcatcagttt gtttgcttgc        60
aaacaaacgc tggcgaccgg cgcacgggtg agtaacacgt atccaaccta cctcatactc       120
ggggatagcc tttcgaaaga aagattaata tccgatagca tatatttccc gcatgggtnn       180
natattaaag aaattcggta tgagatgggg atgcgttcca ttagtttgtt gggggggtaa       240
cggcccacca agactacgat ggatagggggt tctgagagga aggtccccca cattggaact      300
gagacacggt ccaaactcct acgggaggca gcagtgagga atattggtca atggacgcga       360
gtctgaacca gccaagtagc gtgaaggatg actgccctat gggttgtaaa cttcttttat       420
atgggaataa agtggtccac gtgtggactt ttgtatgtac catatgaata aggatcggct       480
aactccgtgc cagcagccgc ggtaatacgg aggatccgag cgttatccgg atttattggg       540 tttaaagggga gcgtaggcgg attgttaagt cagttgtgaa agtttgcggc tcaaccgtaa       600
aattgcagtt gatactggca gtcttgagtg cagtagaggt gggcggaatt cgtggtgtag       660
cggtgaaatg cttagatatc acgaagaact ccgattgcga aggcagctca ctggagtgta       720
actgacgctg atgctcgaaa gtgtgggtat caaacaggat tagataccct ggtagtccac       780
acagtaaacg atgaatactc gctgtttgcg atatacagta agcggccaag cgaaagcatt       840
aagtattcca cctggggagt acgccggcaa cggtgaaact caaaggaatt gacgggggcc       900
ngcacaagcg gaggaacatg tggtttaatt cgatgatacg cgaggaacct tacccgggct       960
taaattgcaa atgaattatg gggaaaccca tacgccgcaa ggcatntgtg aaggtgctgc      1020
atggttgtcg tcagctcgtg ccgtgaggtg tcggcttaag tgccataacg agcgcaaccc      1080
ttatcttcag ttactaacag gtcatgctga ggactctgga gagactgccg tcgtaagatg      1140
tgaggaaggt ggggggatgacg tcaaatcagc acggccctta cgtccggggc tacacacgtg      1200
```

-continued

```
ttacaatggg gggtacagaa ggcagctacc tggtgacagg atgccaatcc caaaaacctc      1260
tctcagttcg gatcgaagtc tgcaacccga cttcgtgaag ctggattcgc tagtaatcgc      1320
gcatcagcca tggcgcggtg aatacgttcc cgggccttgt acacaccgcc cgtcaagcca      1380
tgaaagccgg gggtacctga agtacgtaac cgcaaggagn gt                         1422
```

<210> SEQ ID NO 5
<211> LENGTH: 1493
<212> TYPE: DNA
<213> ORGANISM: Bacteroides dorei

<400> SEQUENCE: 5

```
agagtttgat cctggctcag gatgaacgct agctacaggc ttaacacatg caagtcgagg       60
ggcagcatgg tcttagcttg ctaaggctga tggcgaccgg cgcacgggtg agtaacacgt      120
atccaacctg ccgtctactc ttggccagcc ttctgaaagg aagattaatc caggatggga      180
tcatgagttc acatgtccgc atgattaaag gtattttccg gtagacgatg gggatgcgtt      240
ccattagata gtaggcgggg taacggccca cctagtcaac gatggatagg ggttctgaga      300
ggaaggtccc ccacattgga actgagacac ggtccaaact cctacgggag gcagcagtga      360
ggaatattgg tcaatgggcg atggcctgaa ccagccaagt agcgtgaagg atgactgccc      420
tatgggttgt aaacttcttt tataaaggaa taaagtcggg tatgcatacc cgtttgcatg      480
tactttatga ataaggatcg gctaactccg tgccagcagc cgcggtaata cggaggatcc      540
gagcgttatc cggatttatt gggtttaaag ggagcgtaga tggatgttta agtcagttgt      600
gaaagtttgc ggctcaaccg taaaattgca gttgatactg gatgtcttga gtgcagttga      660
ggcaggcgga attcgtggtg tagcggtgaa atgcttagat atcacgaaga actccgattg      720
cgaaggcagc ctgctaagct gcaactgaca ttgaggctcg aaagtgtggg tatcaaacag      780
gattagatac cctggtagtc cacacggtaa acgatgaata ctcgctgttt gcgatacg        840 gcaagcggcc aagcgaaagc gttaagtatt ccacctgggg agtacgccgg caacggtgaa      900
actcaaagga attgacgggg gcccgcacaa gcggaggaac atgtggttta attcgatgat      960
acgcgaggaa ccttacccgg gcttaaattg cactcgaatg atccggaaac ggttcagcta     1020
gcaatagcga gtgtgaaggt gctgcatggt tgtcgtcagc tcgtgccgtg aggtgtcggc     1080
ttaagtgcca taacgagcgc aacccttgtt gtcagttact aacaggtgat gctgaggact     1140
ctgacaagac tgccatcgta agatgtgagg aaggtgggga tgacgtcaaa tcagcacggc     1200
ccttacgtcc ggggctacac acgtgttaca atggggggta cagagggccg ctaccacgcg     1260
agtggatgcc aatccctaaa acccctctca gttcggactg gagtctgcaa cccgactcca     1320
cgaagctgga ttcgctagta atcgcgcatc agccacggcg cggtgaatac gttcccgggc     1380
cttgtacaca ccgcccgtca agccatggga gccggggggta cctgaagtgc gtaaccgcga     1440
ggatcgccct agggtaaaac tggtgactgg ggctaagtct aaccaaggta acc            1493
```

<210> SEQ ID NO 6
<211> LENGTH: 1425
<212> TYPE: DNA
<213> ORGANISM: Bacteroides eggerthii

<400> SEQUENCE: 6

```
aggttgatca tggctcagga tgaacgttag ctacaggact tacacatgca agtcgagggg       60
cagcatgatt gaagcttgct tcaatcgatg gcgaccggcg cacgggtgag taacacgtat      120
ccaacctgcc gataactcgg ggatagcctt tcgaaagaaa gattaatacc cgatagtata      180
```

-continued

```
gtttttccgc atggtttcat tattaaagaa tttcggttat cgatgggat gcgttccatt    240 agatagttgg cggggtaacg gcccaccaag tcaacgatgg ataggggttc tgagaggaag    300
gtcccccaca ttggaactga gacacggtcc aaattcctac gggaggcagc agtgaggaat    360
attggtcaat ggacgagagt ctgaaccagc caagtagcgt gaaggatgac tgccctatgg    420
gttgtaaact tctttttatac gggaataaag tggagtatgc atactccttt gtatgtaccg    480
tatgaataag gatcggctaa ctccgtgcca gcagccgcgg taatacggag gatccgagcg    540
ttatccggat ttattgggtt taaagggagc gtaggcgggt gcttaagtca gttgtgaaag    600
tttgcggctc aaccgtaaaa ttgcagttga tactgggcgc cttgagtgca gcataggtag    660
gcggaattcg tggtgtagcg gtgaaatgct tagatatcac gaagaactcc gattgcgaag    720
gcagcttact ggactgtaac tgacgctgat gctcgaaagt gtgggtatca aacaggatta    780
gataccctgg tagtccacac agtaaacgat gaatactcgc tgttggcgat acacagtcag    840
cggccaagcg aaagcattaa gtattccacc tggggagtac gccggcaacg gtgaaactca    900
aaggaattga cggggggcccg cacaagcgga ggaacatgtg gtttaattcg atgatacgcg    960
aggaacctta cccgggctta aattgcagcg gaatgtagtg gaaacattac agccttcggc    1020
cgctgtgaag tgctgcatgg ttgtcgtcag ctcgtgccgt gaggtgtcgg cttaagtgcc    1080
ataacgagcg caaccttat ctatagttac tatcaggtca tgctgaggac tctatgagga    1140
ctgccgtcgt aagatgtgag gaaggtgggg atgacgtcaa atcagcacgg cccttacgtc    1200
cggggctaca cacgtgttac aatggggggt acagaaggca gctacctggc gacaggatgc    1260
taatcccgaa aacctctctc agttcggatt ggagtctgca acccgactcc atgaagctgg    1320
attcgmtagt aatcgcgcat cagccacggc gcggtgaata cgttcccggg ccttgtacac    1380
accgcccgtc aagccatgaa agccgggggt acctgaagta cgtaa               1425
```

```
<210> SEQ ID NO 7
<211> LENGTH: 1539
<212> TYPE: DNA
<213> ORGANISM: Bacteroidetes distasonis
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (482)..(482)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (932)..(932)
```

```
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1490)..(1491)
<223> OTHER INFORMATION: n is a, c, g, or t
<220> FEATURE:
<221> NAME/KEY: misc_feature
<222> LOCATION: (1500)..(1505)
<223> OTHER INFORMATION: n is a, c, g, or t
<220> FEATURE:
<221> NAME/KEY: misc_feature
<222> LOCATION: (1516)..(1524)
<223> OTHER INFORMATION: n is a, c, g, or t

<400> SEQUENCE: 7
caatttaaac aacgaagagt ttgatcctgg ctcaggatna acgctagcga caggcttaac        60
acatgcaagt cgaggggcac gcgcgrgtag caataccgng ngctggcnac cggcgcacgg       120
gtgagtaacg cgtatgcaac ttgcctatca gaggggata acccggcgaa agtcggacta       180
ataccgcatg aagcagggat cccgcatggg aatatttgct aaagattcat cgctnataga       240
taggcatgcg ttccattagg cagttggcgg ggtaacggcc caccaaaccg acgatggata       300
ggggttctga gaggaaggtc ccccacattg gtactgagac acggaccaaa ctcctacggg       360
aggcagcagt gaggaatatt ggtcaatggc cgagaggctg aaccagccaa gtcgcgtgag       420
ggatgaaggt tctatggatc gtaaacctct tttataaggg aataaagtgc gggacgtgtc       480
cngttttgta tgtaccttat gaataaggat cggctaactc cgtgccagca gccgcggtaa       540
tacggaggat ccgagcgtta tccggattta ttgggtttaa agggtgcgta ggcggccttt       600
taagtcagcg gtgaaagtct gtggctcaac catagaattg ccgttgaaac tgggggngctt       660 gagtatgttt gaggcaggcg gaatgcgtgg tgtagcggtg aaatgcatag atatcacgca       720
gaaccccgat tgcgaaggca gcctgccaag ccattactga cgctgatgca cgaaagcgtg       780
gggatcaaac aggattagat accctggtag tccacgcagt aaacgatgat cactagctgt       840
ttgcgataca ctgtaagcgg cacagcgaaa gcgttaagtg atccacctgg ggagtacgcc       900
ggcaacggtg aaactcaaag gaattgacgg gngccngcac aagcggagga acatgtggtt       960
taattcgatg atacgcgagg aaccttaccc gggtttgaac gcattcggac cgaggtggaa      1020 acacctttc tagcaatagc cgtttgcgag gtgctgcatg gttgtcgtca gctcgtgccg      1080
tgaggtgtcg gcttaagtgc cataacgagc gcaacccttg ccactagtta ctaacaggtt      1140
aggctgagga ctctggtggn actgccagcg taagctgcga ggaaggcggg gatgacgtca      1200
aatcagcacg gcccttacat ccggggcgac acacgtgtta caatggcgtg acaaaggga      1260 ggccacctgg cgacagggag cgaatcccca aaccacgtct cagttcggat cggagtctgc      1320 aaccgactc cgtgaagctg gattcgctag taatcgcgca tcagccatgg cgcggtgaat      1380
acgttcccgg gccttgtaca caccgcccgt caagccatgg gagccggggg tacctgaagt      1440
ccgtaaccga aaggatcggc ctaggtaaa actggtgact ggggctaagn ngtaacaagn      1500
nnnnngtacc ggaagnnnnn nnnngaacac ctcctttct                            1539

<210> SEQ ID NO 8
<211> LENGTH: 1515
```

-continued

<212> TYPE: DNA
<213> ORGANISM: Bifidobacterium infantis

<400> SEQUENCE: 8

```
tttgatcatg gctcaggatg aacgctggcg gcgtgcttaa cacatgcaag tcgaacggga      60
tccatcgggc tttgcttggt ggtgagagtg gcgaacgggt gagtaatgcg tgaccgacct     120
gccccataca ccggaatagc tcctggaaac gggtggtaat gccggatgtt ccagttgatc     180
gcatggtctt ctgggaaagc tttcgcggta tgggatgggg tcgcgtccta tcagcttgac     240
ggcggggtaa cggcccaccg tggcttcgac gggtagccgg cctgagaggg cgaccggcca     300
cattgggact gagatacggc ccagactcct acgggaggca gcagtgggga atattgcaca     360
atgggcgcaa gcctgatgca gcgacgccgc gtgagggatg gaggccttcg ggttgtaaac     420
ctcttttatc ggggagcaag cgtgagtgag tttacccgtt gaataagcac cggctaacta     480
cgtgccagca gccgcggtaa tacgtagggt gcaagcgtta tccggaatta ttgggcgtaa     540
agggctcgta ggcggttcgt cgcgtccggt gtgaaagtcc atcgcttaac ggtggatccg     600
cgccgggtac gggcgggctt gagtgcggta ggggagactg gaattcccgg tgtaacggtg     660
gaatgtgtag atatcgggaa gaacaccaat ggcgaaggca ggtctctggg ccgttactga     720
cgctgaggag cgaaagcgtg gggagcgaac aggattagat accctggtag tccacgccgt     780
aaacggtgga tgctggatgt ggggcccgtt ccacgggttc cgtgtcggag ctaacgcgtt     840
aagcatcccg cctggggagt acggccgcaa ggctaaaact caaagaaatt gacggggggcc     900 cgcacaagcg gcggagcatg cggattaatt cgatgcaacg cgaagaacct tacctgggct     960
tgacatgttc ccgacgatcc cagagatggg gtttcccttc ggggcgggtt cacaggtggt    1020
gcatggtcgt cgtcagctcg tgtcgtgaga tgttgggtta agtcccgcaa cgagcgcaac    1080
cctcgccccg tgttgccagc ggattgtgcc gggaactcac gggggaccgc cggggttaac    1140
tcggaggaag gtggggatga cgtcagatca tcatgcccct tacgtccagg gcttcacgca    1200
tgctacaatg gccggtacaa cgggatgcga cgcggcgacg cggagcggat ccctgaaaac    1260
cggtctcagt tcggatcgca gtctgcaact cgactgcgtg aaggcggagt cgctagtaat    1320
cgcgaatcag caacgtcgcg gtgaatgcgt tcccgggcct tgtacacacc gcccgtcaag    1380
tcatgaaagt gggcagcacc cgaagccggt ggcctaaccc cttgtgggat ggagccgtct    1440
aaggtgaggc tcgtgattgg gactaagtcg taacaaggta gccgtaccgg aaggtgcggc    1500
tggatcacct cctta                                                     1515
```

<210> SEQ ID NO 9
<211> LENGTH: 1476
<212> TYPE: DNA
<213> ORGANISM: Bifidobacterium longum
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (268)..(269)
<223> OTHER INFORMATION: n is a, c, g, or t
<220> FEATURE:

```
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1137)..(1138)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1394)..(1394)
<223> OTHER INFORMATION: n is a, c, g, or t
<220> FEATURE:
<221> NAME/KEY: misc_feature
<222> LOCATION: (1443)..(1443)
<223> OTHER INFORMATION: n is a, c, g, or t

<400> SEQUENCE: 9
ttttgtggag ggttcgattc tggctcagga tgaacgctgg cggcgtgctt aacacatgca        60
agtcgaacgg gatccatcaa gcttgcttgg tggtgagagt ggcgaacggg tgagtaatgc       120
gtgaccgacc tgccccatac accggaatag ctcctggaaa cgggtggtaa tgccggatgt       180
tccagttgat cgcatggtct tctggngaaa gcntttcgcg gtatgggatg gggtcgcgtc       240
ctatcagctt gacggnggggg taacggcnna ccgtggcttc gacgggtagc cggcctgaga      300
gggcgaccgg ccacattggg actgagatac ggcccngact cctacgggag gcagcagtgg       360
ggaatattgc acaatgggcg caagcctgat gcagcgacgc cgcgtgaggg atggaggcct       420
tcgggttgta aacctctttt atcggggagc aagcgagagt gagtttaccc gttgaataag       480
caccggctaa ctacgtgcca gcagccgcgg taatacgtag ggtgcnagcg ttatccggaa       540
ttattgggcg taaagggctc gtaggcggtt cgtcgcgtcc ggtgtgaaag tccatcgctt       600
aacggtggat ccgcgccggg tacgggcggg cttgagtgcg gtaggggaga ctggaattcc       660
cggtgtaacg gtggaatgtg tagatatcgg gaagaacacc aatggcgaag gcaggtctct       720
gggccgttac tgacgctgag gagcgaaagc gtggggagcg aacaggatta gataccctgg       780
```

-continued

```
tagtccacgc cgtaaacggt ggatgctgga tgtggggccn gttccacggg ttccgtgtcg      840
gagctaacgc gttaagcatc ccgcctgggg agtacggccg caaggctaaa actcaaagaa      900
attgacgggg gccngcacaa gcggcggagc atgcggatta attcgatgna acgcgaagaa      960
ccttacctgg gcttgacatg ttcccgacgg tcgtagagat acggcntccc ttcggggcgg     1020
gttcacaggt ggngcatggt cgtcgtcagc tcgtgtcgtg agatgttggg ttaagtcccg     1080
caacgagcgc aaccctcgcc ccgtgttgcc agcggattat gccggnaact cacgggnnac     1140
cgccggggtt aactcggagg aaggtgggga tgacgtcaga tcatcatgcc ccttacgtcc     1200
agggcttcac gcatgctaca atggccgta caacgggatg cgacgcggcg acgcggagcg     1260
gatccctgaa aaccngtctc agttcggatc gcagtctgca actcgactgc gtgaaggcgg     1320
agtcgctagt aatcgcgaat cagcaacgtc gcggtgaatg cgttcccngg ccttgtacac     1380
accgcccgtc aagncatgaa agtgggcagc acccgaagcc ggtggcctaa ccccttgtgg     1440
ganggagccg tctaaggtga ggctcgtgat tgggac                              1476
```

<210> SEQ ID NO 10
<211> LENGTH: 1520
<212> TYPE: DNA
<213> ORGANISM: Bifidobacterium breve
<400> SEQUENCE: 10

```
ttcgattctg gctcaggatg aacgctggcg gcgtgcttaa cacatgcaag tcgaacggga       60
tccatcgggc tttgcttggt ggtgagagtg cgaacgggt gagtaatgcg tgaccgacct      120
gccccatgca ccggaatagc tcctggaaac gggtggtaat gccggatgct ccatcacacc      180
gcatggtgtg ttgggaaagc ctttgcggca tgggatgggg tcgcgtccta tcagcttgat      240
ggcggggtaa cggcccacca tggcttcgac gggtagccgg cctgagaggg cgaccggcca      300
cattgggact gagatacggc ccagactcct acgggaggca gcagtgggga atattgcaca      360
atgggcgcaa gcctgatgca gcgacgccgc gtgagggatg gaggccttcg ggttgtaaac      420
ctcttttgtt agggagcaag gcactttgtg ttgagtgtac ctttcgaata agcaccggct      480
aactacgtgc cagcagccgc ggtaatacgt agggtgcaag cgttatccgg aattattggg      540
cgtaaagggc tcgtaggcgg ttcgtcgcgt ccggtgtgaa agtccatcgc ttaacggtgg      600
atccgcgccg ggtacgggcg gcttgagtg cggtaggga gactggaatt cccggtgtaa      660
cggtggaatg tgtagatatc gggaagaaca ccaatggcga aggcaggtct ctgggccgtt      720
actgacgctg aggagcgaaa gcgtggggag cgaacaggat tagataccct ggtagtccac      780
gccgtaaacg gtggatgctg atgtggggc ccgttccacg ggttccgtgt cggagctaac      840
gcgttaagca tcccgcctgg ggagtacggc cgcaaggcta aaactcaaag aaattgacgg      900
gggcccgcac aagcggcgga gcatgcggat taattcgatg caacgcgaag aaccttacct      960
gggcttgaca tgttcccgac gatcccagag atggggtttc ccttcggggc gggttcacag     1020
gtggtgcatg gtcgtcgtca gctcgtgtcg tgagatgttg ggttaagtcc cgcaacgagc     1080
gcaaccctcg ccccgtgttg ccagcggatt gtgccgggaa ctcacggggg accgccgggg     1140
ttaactcgga ggaaggtggg gatgacgtca gatcatcatg ccccttacgt ccagggcttc     1200
acgcatgcta caatggccgg tacaacggga tgcgacagtg cgagctggag cggatccctg     1260
aaaaccggtc tcagttcgga tcgcagtctg caactcgact gcgtgaaggc ggagtcgcta     1320
gtaatcgcga atcagcaacg tcgcggtgaa tgcgttcccg gccttgtac acaccgcccg     1380
```

```
tcaagtcatg aaagtgggca gcacccgaag ccggtggcct aaccccttgc gggagggagc      1440
cgtctaaggt gaggctcgtg attgggacta agtcgtaaca aggtagccgt accggaaggt      1500
gcggctggat cacctcctta                                                  1520

<210> SEQ ID NO 11
<211> LENGTH: 1533
<212> TYPE: DNA
<213> ORGANISM: Bifidobacterium thermophilum

<400> SEQUENCE: 11
agagtttgat catggctcag gatgaacgct ggcggcgtgc ttaacacatg caagtcgaac       60
gggatcctgc gggctttgcc tgcgggtgag agtggcgaac gggtgagtaa tgcgtgacca      120
acctgcccca tgctccggaa tagctcctgg aaacgggtgg taatgccgga tgttcccgcg      180
ccccgcatgg ggtgcgggga aaagcttttg cggcgtggga tggggtcgcg tcctatcagc      240
ttgttggcgg ggtgagggcc caccaaggct tcgacgggta gccggcctga gaaggcgacc      300
ggccacattg ggactgagat acggcccaga ctcctacggg aggcagcagt ggggaatatt      360
gcacaatggg cgcaagcctg atgcagcgac gccgcgtgcg ggatggaggc cttcgggttg      420
taaaccgctt ttgtttggga gcaagccctt cggggtgagt gtacctttcg aataagcacc      480
ggctaaatac gtgccagcag ccgcggtaat aagtagggtg cgagcgttat ccggatttat      540
tgggcgtaaa gggcttgtag gcggtttgtc gcgtccggtg tgaaagtcca tcgcctaacg      600
gtggatttgc gccgggtacg ggcgggctgg agtgcggtag gggagactgg aattcccggt      660
gtaacggtgg aatgtgtaga tatcgggaag aacaccaatg gcgaaggcag gtctttgggc      720
cgttactgac gctgaggagc gaaagcgtgg ggagcgaaca ggattagata ccctggtagt      780
ccacgccgta aacggtggat gctggatgtg gggcccttcc acgggtcccg tgtcggggcc      840
aacgcgttaa gcatcccgcc tggggagtac ggccgcaagg ctaaaactca aagaaattga      900 cggggggcccg cacaagcggc ggagcatgcg gattaattcg atgcaacgcg aaaaacctta      960
cctgggcttg acatgttccc gacgacggca gagatgtcgt ttcccttcgg ggcgggttca     1020
caggtggtgc atggtcgtcg tcagctcgtg tcgtgagatg ttgggtcaag tcccgcaacg     1080
agcgcaaccc tcgccccgtg ttgccagcgc gtcttggcgg gaactcaccg gggaccgccg     1140
gggtttaccc ggaggaaggt ggggatgacg tcagatcatc atgccccctta cgtccagggc     1200 ttcacggcat gctacaatgg ccgggtacag gcggggatgc agacatggtg acatggagcg     1260
ggatccctga aaaccggtct cagttcggga tcggagcgtg caacccggct cggtgaaggc     1320
ggagtcggct aagtaatcgc ggatcagcaa cgccgcggtg aatgcgttcc cgggccttgt     1380
acacaccgcc cgtcaagtca tgaaagtggg cagcacccga gccggtggc ctgaccagta     1440 ttgctggggg gagccgtcta aggtgaggct cgcgattggg agtaagtcgt aacaaggtag     1500
ccgtaccgga aggtgcggct ggatcacctc ctt                                 1533

<210> SEQ ID NO 12
<211> LENGTH: 1532
<212> TYPE: DNA
<213> ORGANISM: Bifidobacterium bifidum
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
```

```
<220> FEATURE:
<221> NAME/KEY: misc_feature
<222> LOCATION: (525)..(528)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (1139)..(1140)
<223> OTHER INFORMATION: n is a, c, g, or t
<220> FEATURE:
<221> NAME/KEY: misc_feature
<222> LOCATION: (1156)..(1156)
<223> OTHER INFORMATION: n is a, c, g, or t
<220> FEATURE:
<221> NAME/KEY: misc_feature
<222> LOCATION: (1471)..(1471)
<223> OTHER INFORMATION: n is a, c, g, or t
<220> FEATURE:
<221> NAME/KEY: misc_feature
<222> LOCATION: (1483)..(1484)
<223> OTHER INFORMATION: n is a, c, g, or t
<220> FEATURE:
<221> NAME/KEY: misc_feature
<222> LOCATION: (1493)..(1498)
<223> OTHER INFORMATION: n is a, c, g, or t
<220> FEATURE:
<221> NAME/KEY: misc_feature
<222> LOCATION: (1509)..(1517)
<223> OTHER INFORMATION: n is a, c, g, or t

<400> SEQUENCE: 12
tttttgtgga gggttcgatt ctggctcagg atgaacgctg gcggcgtgct taacacatgc      60
aagtcgaacg ggatccatca agcttgcttg gtggtgagag tggcgaacgg gtgagtaatg     120
cgtgaccgac ctgccccatg ctccggaata gctcctggaa acgggtggta atgccgnatg     180
ttccacatga tcgcatgtga ttgtgggaaa gattctatcg gcgtgggatg gggtcgngtc     240
ctatcagctt gttggtgagg taacggctca ccaaggcttc gacgggtagc cggcctgaga     300
gggcgaccgg ccacattggg actgagatac ggcccagact cctacgggag gcagcagtgg     360
ggaatattgc acaatgggcg caagcctgat gcagcgacgc cgcgtgaggg atggaggcct     420
tcgggttgta aacctctttt gtttgggagc aagccttcgg gtgagtgtac ctttcgaata     480
agcgccggct aactacgtgc cagcagccgc ggtaatacgt agggnnnnag cgttatccgg     540
atttattggg cgtaaagggc tcgtaggcgg ctcgtcgcgt ccggtgtgaa agtccatcgc     600
ttaacggtgg atctgcgccg ggtacgggcg ggctggagtg cggtagggga gactggaatt     660
cccggtgtaa cggtggaatg tgtagatatc gggaagaaca ccgatggcga aggcaggtct     720
ctgggcngtc actgacgctg aggagcnaaa gcgtggggag cgaacaggat tagataccct     780
ggtagtccac gccgtaaacg gtggacgctg gatgtggggc acgttccacg tgttccgtgt     840
cggagctaac gcgttaagcg tcccgcctgg ggagtacggc cgcaaggcta aaactcaaag     900
aaattgacgg gggccngcac aagcggcgga gcatgcggat taattcgaac naacgcgaag     960
```

```
aaccttacct gggcttgaca tgttcccgac gacgccagag atggcgtttc ccttcggggc      1020
gggttcacag gtggtgcatg gtcgtcgtca gctcgtgtcg tgagatgttg ggttaagtcc      1080
cgcaacgagc gcaaccctcg ccccgtgttg ccagcacgtt atggtgggaa ctcacgggnn      1140
accgccgggg ttaacncgga ggaaggtggg gatgacgtca gatcatcatg ccccttacgt      1200
ccagggcttc acgcatgcta caatggccgg tacagcggga tgcgacatgg cgacatggag      1260
cggatccctg aaaaccggtc tcagttcgga tcggagcctg caacccggct ccgtgaaggc      1320
ggagtcgcta gtaatcgcgg atcagcaacg ccgcggtgaa tgcgttcccg ggccttgtac      1380
acaccgcccg tcaagtcatg aaagtgggca gcacccgaag ccggtggcct aaccccttgt      1440
gggatggagc cgtctaaggt gaggctcgtg nttgggacta agnngtaaca agnnnnnngt      1500
accggaagnn nnnnnnngat cacctccttt ct      1532
```

```
<210> SEQ ID NO 13
<211> LENGTH: 1477
<212> TYPE: DNA
<213> ORGANISM: Bifidobacterium adolescentis
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
```

-continued

```
<222> LOCATION: (667)..(667)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (916)..(917)
<223> OTHER INFORMATION: n is a, c, g, or t
<220> FEATURE:
<221> NAME/KEY: misc_feature
<222> LOCATION: (920)..(921)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (954)..(955)
<223> OTHER INFORMATION: n is a, c, g, or t
<220> FEATURE:
<221> NAME/KEY: misc_feature
<222> LOCATION: (1011)..(1013)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1132)..(1132)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1175)..(1175)
<223> OTHER INFORMATION: n is a, c, g, or t
<220> FEATURE:
<221> NAME/KEY: misc_feature
<222> LOCATION: (1283)..(1283)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1435)..(1435)
<223> OTHER INFORMATION: n is a, c, g, or t
<220> FEATURE:
<221> NAME/KEY: misc_feature
<222> LOCATION: (1466)..(1466)
<223> OTHER INFORMATION: n is a, c, g, or t
<220> FEATURE:
<221> NAME/KEY: misc_feature
<222> LOCATION: (1475)..(1475)
<223> OTHER INFORMATION: n is a, c, g, or t

<400> SEQUENCE: 13
nnnnttgtgg agggttcgat tctggctcag gatnaacgct ngcggcgtgc ttaacacatg      60
```

```
caagtcgaac gggatcggct ngagcttgct ccggctgtga gagtggcgaa cgggtgagta    120
atgcgtgacc gacctgcccc atacaccgga atagctcctg gaaacgggtg gtaatgccgg    180
atgctccagt tggatgcatg tccttctggg aaagattcta tcggtatggg atggggtcgc    240
gtcctatcag cttgatggcg gggtaacggc ccnccatggc ttcgacgggn agccggcctg    300
agagggcgac cggccacatt gggactgaga tacggcccng actcctacgg gaggcagcag    360
tgggnaatat tgcacaatgg cgcaagcct aatgcagcga cgccgcgtgc gggatgacgg    420
ccttcgggtt gtaaaccgct tttgactggg agcaagcctt cggggtgagt gtacctttcg    480
aataagcacc ggctaactac gtgccagcag ccncggtaat acgtagggtg cnagcgttat    540
ccggaattat tgggcgtaaa gggctcgtag gcggttcgtc gcgtccggtg tgaaagtcca    600
tcgcttaacg gtggntccgc gccgggtacg ggcggncttg agtgcggtag ggnagactgg    660
aattccnggt gtaacggtgg aatgtgtaga tatcgggaag aacaccaatg gcgaaggcag    720
gtctctgggc ngtnactgac gctgaggagc gaaagcgtgg ggagcgaaca ggattagata    780
ccctggtagt ccacgccgta aacggtggat gctggatgtg gggaccattc cacggtctcc    840
gtgtcggagc caacgcgtta agcatcccgc ctggggagta cggccgcaag gctaaaactc    900
aaagaaattg acgggnnccn ncacaagcgg cngagcatgc ggattaattc gatnnaacgc    960
gaagaacctt acctgggctt gacatgttcc cgacaggccc cagagatggg nnntccttcg   1020
ggncgggntc acaggtggng catggtcgtc gtcagctcgt gtcgtgagat gttgggttaa   1080
gtcccgcaac gagcgcaacc ctcgccctgt gttgccagca cgtcgtggtg gnaactcacg   1140
ggngaccgcc ggggtcaact cggaggaagg tgggnatgac gtcagatcat catgcccctt   1200
acgtccaggg cttcacgcat gctacaatgg ccggtacaac gggatgcgac ctcgtgaggg   1260
ggagcggatc ccttaaaacc ggnctcagtt cggattggag tctgcaaccc gactccatga   1320
aggcggagtc gctagtaatc gcggatcagc aacgccgcgg tnaatgcgtt cccgggcctt   1380
gtacacaccg cccgtcaagc catgaaagtg ggtagcaccc gaagccggtg gcccnacctt   1440
tttgggggga gccgtctaag gtgagnctcg tgatngg                            1477
```

```
<210> SEQ ID NO 14
<211> LENGTH: 1478
<212> TYPE: DNA
<213> ORGANISM: Bifodbacterium catenulatum
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
```

-continued

```
<222> LOCATION: (208)..(208)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (269)..(271)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (336)..(337)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (402)..(404)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t
<220> FEATURE:
<221> NAME/KEY: misc_feature
<222> LOCATION: (822)..(823)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
```

-continued

```
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (890)..(894)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (917)..(917)
<223> OTHER INFORMATION: n is a, c, g, or t
<220> FEATURE:
<221> NAME/KEY: misc_feature
<222> LOCATION: (928)..(928)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t
<220> FEATURE:
<221> NAME/KEY: misc_feature
<222> LOCATION: (950)..(952)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1025)..(1026)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1051)..(1051)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1129)..(1129)
<223> OTHER INFORMATION: n is a, c, g, or t
<220> FEATURE:
<221> NAME/KEY: misc_feature
<222> LOCATION: (1139)..(1140)
<223> OTHER INFORMATION: n is a, c, g, or t
<220> FEATURE:
<221> NAME/KEY: misc_feature
<222> LOCATION: (1279)..(1279)
<223> OTHER INFORMATION: n is a, c, g, or t
<220> FEATURE:
<221> NAME/KEY: misc_feature
<222> LOCATION: (1388)..(1388)
<223> OTHER INFORMATION: n is a, c, g, or t
```

<220> FEATURE:
<221> NAME/KEY: misc_feature
<222> LOCATION: (1396)..(1396)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1436)..(1436)
<223> OTHER INFORMATION: n is a, c, g, or t

<400> SEQUENCE: 14
nnnttttgtg agnggttcga ttctggctca ggatgaacgc tggcggcgtg cttaacacat      60
gcaagtcgaa cgggatcagg cagcttgctg cctggngaga gtggcgaacg ggnnagtaat     120
gcgtgaccna cctgccnnat acaccggaat agctcctgga aacgggtggt aatgccggat     180
gctccgactc ctcgcatggg gtgtcggnaa agatttcatc ggtatgggat ggggtcgngt     240
cctatcaggt agtcggcggg gtaacggcnn nccgagcctn cgacgggtag ccggcctgag     300
agggcgaccg gccacattgg gactgagata cggccnngac tcctacggga ggcagcagtg     360
ggncatattg cacaatgggc gcaagcctna tgcagcgacg cnnngtgcgg gntgacggcc     420
tncgggttgt aaacncntt tgatcgggag caagccttcg ggtgagtgta ccnttcgaat     480
aagcaccggc taactacgtg ccagcagccg cggtaatacg tagggtgcna gcgttatccg     540
gaattattgg gcgtaaaggg ctcgtaggcg gttcgtcgcg tccggtgtga aagtccatcg     600
cttaacggtg gatctgcgcc gggtacgggc gggctggagt gcggtagggg ngactggaat     660
tcccggtgta acggtggaat gtgtagatat cgggaagaac accaatggcg aaggcnggtc     720
tctgggcngn nactgacgct gaggagcgaa agcgtgggga gcgaacagga ttagataccc     780
tggtagtcca cgccgtaaac ggtggatgct ggatgtgggg cnngttccac gggttccgtg     840
tcggagctaa cgcgttaagc atccngcctg gggngtncgg cngcaaggcn nnnncncaaa     900
gaaattgang ggggccngca caagcggngg agcatgcgga ttnattcgan nnaacgcgaa     960
gaaccttacc tgggcttgac atgttcccga cagccgtaga gatacggnct cccttcggggg   1020 cgggnncaca ggtggngcat ggtcgtcgtc ngctcgtgtc gtgagatgtt gggttaagtc    1080
ccncaacgag cgcaaccctc gccctgtgtt gccgacacgt catgtnggna ctcacgggnn    1140
accgccgggg tcaactcgga ggaaggtggg gatgacgtca gatcatcatg cccccttacgt   1200 ccagggcttc acgcatgcta caatggccgg tacaacggga tgcgacatgg cgacatggag    1260
cggatccctg aaaaccggnc tcagttcgga ttggagtctg caacccgact ccatgaaggc    1320
ggagtcgcta gtaatcgcgg atcagcaacg ccgcggtgaa tgcgttcccg ggccttgtac    1380
acaccgcncg tcaagncatg aaagtgggta gcacccgaag ccggtggcct naccncttgt    1440
gggatggagc cgtctaaggt gagactcgtg attgggac                           1478

<210> SEQ ID NO 15
<211> LENGTH: 1519
<212> TYPE: DNA
<213> ORGANISM: Bifidobacterium pseudocatenulatum

<400> SEQUENCE: 15
gtttcgattc tggctcagga tgaacgctgg cggcgtgctt aacacatgca agtcgaacgg      60
gatccatcag gctttgcttg gtggtgagag tggcgaacgg gtgagtaatg cgtgaccgac     120
ctgccccata caccggaata gctcctggaa acgggtggta atgccggatg ctccgactcc     180

-continued

```
tcgcatgggg tgtcgggaaa gatttcatcg gtatgggatg gggtcgcgtc ctatcaggta        240
gtcggcgggg taacggccca ccgagcctac gacgggtagc cggcctgaga gggcgaccgg        300
ccacattggg actgagatac ggcccagact cctacgggag gcagcagtgg ggaatattgc        360
acaatgggcg caagcctgat gcagcgacgc cgcgtgcggg atgacggcct tcgggttgta        420
aaccgctttt gatcgggagc aagccttcgg gtgagtgtac ctttcgaata agcaccggct        480
aactacgtgc cagcagccgc ggtaatacgt agggtgcaag cgttatccgg aattattggg        540
cgtaaagggc tcgtaggcgg ttcgtcgcgt ccggtgtgaa agtccatcgc ttaacggtgg        600
atctgcgccg gtacgggcg ggctggagtg cggtagggga gactggaatt cccggtgtaa        660
cggtggaatg tgtagatatc gggaagaaca ccaatggcga aggcaggtct ctgggccgtt        720
actgacgctg aggagcgaaa gcgtggggag cgaacaggat tagataccct ggtagtccac        780
gccgtaaacg gtggatgctg gatgtggggc ccgttccacg ggttccgtgt cggagctaac        840
gcgttaagca tcccgcctgg ggagtacggc cgcaaggcta aaactcaaag aaattgacgg        900
gggcccgcac aagcggcgga gcatgcggat taattcgatg caacgcgaag aaccttacct        960
gggcttgaca tgttcccgac agccgtagag atatggcctc ccttcggggc gggttcacag       1020
gtggtgcatg gtcgtcgtca gctcgtgtcg tgagatgttg ggttaagtcc cgcaacgagc       1080
gcaaccctcg ccctgtgttg ccagcacgtc atggtgggaa ctcacggggg accgccgggg       1140
tcaactcgga ggaaggtggg gatgacgtca gatcatcatg cccccttacgt ccagggcttc       1200 acgcatgcta caatggccgg tacaacggga tgcgacacgg cgacgtggag cggatccctg       1260
aaaaccggtc tcagttcgga ttggagtctg caacccgact ccatgaaggc ggagtcgcta       1320
gtaatcgcgg atcagcaacg ccgcggtgaa tgcgttcccg ggccttgtac acaccgcccg       1380
tcaagtcatg aaagtgggta gcacccgaag ccggtggcct aaccctttgt ggatggagcc       1440
gtctaaggtg agactcgtga ttgggactaa gtcgtaacaa ggtagccgta ccggaaggtg       1500
cggctggatc acctcctta                                                    1519
```

```
<210> SEQ ID NO 16
<211> LENGTH: 1433
<212> TYPE: DNA
<213> ORGANISM: Akkermansia muciniphila

<400> SEQUENCE: 16
aacgaacgct ggcggcgtgg ataagacatg caagtcgaac gagagaattg ctagcttgct         60
aataattctc tagtggcgca cgggtgagta acacgtgagt aacctgcccc cgagagcggg        120
atagccctgg gaaactggga ttaataccgc atagtatcga aagattaaag cagcaatgcg        180 cttgggatg ggtcgcggc ctattagtta gttggtgagg taacggctca ccaaggcgat         240
gacgggtagc cggtctgaga ggatgtccgg ccacactgga actgagacac ggtccagaca        300
cctacgggtg gcagcagtcg agaatcattc acaatggggg aaaccctgat ggtgcgacgc        360
cgcgtggggg aatgaaggtc ttcggattgt aaaccctgt catgtgggag caaattaaaa        420
agatagtacc acaagaggaa gagacggcta actctgtgcc agcagccgcg gtaatacaga        480
ggtctcaagc gttgttcgga atcactgggc gtaaagcgtg cgtaggctgt ttcgtaagtc        540
gtgtgtgaaa ggcgcgggct caacccgcgg acggcacatg atactgcgag actagagtaa        600 tggagggggga accggaattc tcggtgtagc agtgaaatgc gtagatatcg agaggaacac        660
tcgtggcgaa ggcgggttcc tggacattaa ctgacgctga ggcacgaagg ccaggggagc        720
gaaagggatt agatacccct gtagtcctgg cagtaaacgg tgcacgcttg gtgtgcgggg        780
```

-continued

```
aatcgacccc ctgcgtgccg gagtaacgcg ttaagcgtgc cgcctgggga gtacggtcgc      840
aagattaaaa ctcaaagaaa ttgacgggga cccgcacaag cggtggagta tgtggcttaa      900
ttcgatgcaa cgcgaagaac cttacctggg cttgacatgt aatgaacaac atgtgaaagc      960
atgcgactct tcggaggcgt tacacaggtg ctgcatggcc gtcgtcagct cgtgtcgtga     1020
gatgtttggt taagtccagc aacgagcgca acccctgttg ccagttacca gcacgtgaag     1080
gtggggactc tggcgagact gcccagatca actgggagga aggtggggac gacgtcaggt     1140
cagtatggcc cttatgccca gggctgcaca cgtactacaa tgcccagtac agaggggggcc     1200 gaagccgcga ggcggaggaa atcctaaaaa ctgggcccag ttcggactgt aggctgcaac     1260
ccgcctacac gaagccggaa tcgctagtaa tggcgcatca gctacggcgc cgtgaatacg     1320
ttcccgggtc ttgtacacac cgcccgtcac atcatggaag ctggtcgcac ccgaagtatc     1380
tgaagccaac cgcaaggagg cagggtccta aggtgagact ggtaactggg atg           1433
```

<210> SEQ ID NO 17
<211> LENGTH: 1438
<212> TYPE: DNA
<213> ORGANISM: Akkermansia glycanipila

<400> SEQUENCE: 17

```
aacgaacgct ggcggcgtgg ataagacatg caagtcgaac ggagaagcaa tagcttgcta      60
atgcttctta gtggcgcacg ggtgagtaac acgtgagcaa cctgccttcg agacgggaat     120
agccctggga aaccgggatt aatgcccgat agactcgcaa gagtaaacgc agcaatgcgc     180
ttgaagaggg gctcgcggcc tattagttag ttggtgaggt aacggctcac caaggcgatg     240
acgggtagcc ggtctgagag gatgtccggc cacactggaa ctgagacacg gtccagacac     300
ctacgggtgg cagcagtcga gaatcattca caatggggga aaccctgatg gtgcgacgcc     360
gcgtggggga agaaggtctt cggattgtaa acccctgtca tgtgggagca aggcgcaagc     420
ttgatagtac cacaagagga agagacggct aactctgtgc cagcagccgc ggtaatacag     480
aggtctcaag cgttgttcgg aatcactggg cgtaaagggt acgtaggctg catcataagt     540
cgggcgtgaa aggcaggggc tcaacccctg gagtgcgctt gatactgtga tgctagagtc     600
atggaggggg aaccggaact ctcggtgtag cagtgaaatg cgtagatatc gagaagaaca     660
ctcgtggcga aggcgggttc ctggacatgt actgacgctg aggtacgaag ctagggggag     720
cgaaagggat tagataccccc tgtagtccta gcagtaaacg gtgcacgctt ggtgtgtggg     780
gaatcgaccc cccacgtgcc ggagcaaacg cgttaagcgt gccgcctggg gagtacggtc     840
gcaagattaa aactcaaaga aattgacggg gacccgcaca agcggtggag tatgtggctt     900
aattcgatgc aacgcgaaga accttacctg ggcttgacat gtgatgaaca acatgtgaaa     960
gcatgtgaca cctcggtggc gtcacacagg tgctgcatgg ccgtcgtcag ctcgtgtcgt    1020
gagatgtttg gttaagtcca gcaacgagcg caacccctgt tgccagttac cagcacgtta    1080
tggtggggac tctggcgaga ctgcccagat caactgggag gaaggtgggg acgacgtcag    1140
gtcagtatgg cccttatgcc cagggctgca cacgtactac aatgcccagt acagagggta    1200
ccgaacccgc gaggggggagg caatccatga aaactgggcc cagttcggat tgtaggctgc    1260
aactcgccta catgaagatg gaatcgctag taatggcgca tcagctacgg cgccgtgaat    1320
acgttcccgg gtcttgtaca caccgcccgt cacatcatgg aagccggtcg cacccgaagt    1380
atctgaagcc aaccgcaagg aggcagggtc ctaaggtgag actggtaact gggatgaa      1438
```

FECAL MATTER FOR PREVENTING OR TREATING INTESTINAL MICROBIOME ABERRATIONS IN CESAREAN SECTION-BORN INFANTS

CROSS-REFERENCE TO RELATED APPLICATIONS

This application is a national phase entry under 35 U.S.C. § 371 of International Patent Application PCT/EP2021/076348, filed Sep. 24, 2021, designating the United States of America and published as International Patent Publication WO 2022/063980 A1 on Mar. 31, 2022, which claims the benefit under Article 8 of the Patent Cooperation Treaty to Dutch Patent Application Serial No. NL 2026545, filed Sep. 25, 2020.

STATEMENT REGARDING ELECTRONIC FILING OF A SEQUENCE LISTING

Pursuant to 37 C.F.R. § 1.821, a Sequence Listing ASCII text file entitled "P34733US00_sequence listing_ST25.txt," 47,308 bytes in size, generated Feb. 28, 2023, has been submitted via EFS-Web is provided in lieu of a paper copy. This Sequence Listing is hereby incorporated by reference into the specification for its disclosures.

TECHNICAL FIELD

The application relates to preventing or treating intestinal microbiome aberrations in Cesarean section-born infants.

BACKGROUND

Microbial colonization of the newborn is a pivotal process that affects later life health. The natural microbiota colonization and development can however be disturbed by practices that prevent the maternal transmission of bacteria or alter the microbiota in the infant. One of the strongest factors that disrupt the normal colonization process is birth by cesarean section (CS). This practice effectively eliminates the possibility of natural vertical transfer of gut bacteria from mother to infant at birth, resulting in a deviation of microbiota development, most notably in the first 6 months of life.

CS deliveries are increasing worldwide, affecting over 50% of infants in certain regions and there is emerging evidence that infants born by CS have different bacterial and other exposures that may subtly alter neonatal physiology. Several studies have shown that birth by CS is associated with short and long-term effects, including increased risk of chronic immune diseases (Sevelsted et al., 2015, Keag et al., 2018). A recent Danish study addressing over 2.5 million childbirths in between 1982-2010 with an up to 40-years follow up, showed an increased risk in CS-born children compared with those born by vaginal delivery of four common, immune-mediated hospital-diagnosed childhood chronic inflammatory diseases, including inflammatory bowel diseases, rheumatoid arthritis, coeliac disease, and type 1 diabetes (Andersen et al., 2020). Of note, a recent large UK-based cohort study showed stunted microbiota development, an increased level of pathogens and an impaired mother to infant microbiota transfer in CS-born infants (Shao et al., 2019). Apart from the impact on the individual, this pervasive lack of vertical bacterial transfer may have intergenerational effects: once the inheritance of gut bacteria from mother to daughter is eliminated, is it possible that certain mutualistic bacteria, co-adapted with the host for millennia, are permanently lost (Blaser, 2017). As the role of the father in the vertical microbiota transfer is still enigmatic, one could also envisage that the intergenerational effects are being caused by the male impact although this is intuitively less likely.

The accumulating evidence on the importance of the gut microbiota for overall child development is raising the need for early correction of the microbiota imbalances caused by CS delivery.

In this regard, Dominguez-Bello (2016) report on a study in which infants delivered by C-section were exposed to maternal vaginal fluids at birth, in order to seed microbial communities partly resembling vaginally delivered infants.

Helve et al. (2019) found that the natural seeding of maternal fecal microbes to the newborn intestine can be mimicked in elective CS by transferring a small amount of maternal fecal microbiome orally to the newborn infant.

The aforementioned methods leave room for improvement in preventing or treating intestinal microbiome aberrations in CS-born infants. There remains a need to develop a new or improved strategy to improve the health and prevent susceptibility to disorders in CS-born infants.

BRIEF SUMMARY

It was desired to know whether administration of maternal fecal matter to Cesarean section- (CS-) born infants may have beneficial effects. After investigation, it was indeed found that the intestinal microbiota of the CS-born infants that received the maternal fecal matter resembled the intestinal microbiota of vaginally born infants.

It was found that selective outgrowth takes place of the administered bacterial species within the intestine of the CS-born infants, and that providing at least one *Bacteroides* species and/or at least one *Bifidobacterium* species may be key, since a significant increase in the relative abundance of *Bacteroides* species and/or *Bifidobacterium* species was observed in the treated CS-born infants, in comparison to CS-born infants that did not receive the treatment.

Surprisingly, it was additionally found that the treatment led to a reduction of intestinal colonization of pathogenic microorganisms, an increase in intestinal microbial diversity, an improved immune programming (e.g., as measured by an increase in the level of intestinal secretory IgA and/or intestinal antimicrobial peptides), an increase in immune response to vaccine(s), and a reduced disorder susceptibility, particularly with respect to disorders chosen from the group consisting of metabolic disease, obesity, type 2 diabetes, auto-immune disease, atopy-related disease, allergy and asthma.

Without being bound by any theory, it has been considered that even transient microbiome disturbance in early life may have long-term effects on the metabolic and immunological health, and that the investigative results suggest that, in CS-born infants, such microbiome disturbance may be corrected by providing a composition comprising at least one *Bacteroides* species and/or at least one *Bifidobacterium* species.

The disclosure relates to a composition comprising:
at least one *Bacteroides* species; and/or
at least one *Bifidobacterium* species.

The composition may further comprise at least one *Akkermansia* species.

The composition may be for medical use in a Cesarean section- (CS-) born infant, preferably for use in the prevention or treatment of intestinal microbiota aberration in a Cesarean section- (CS-) born infant.

Accordingly, the disclosure provides for a method, preferably for prevention and/or treatment of intestinal microbiota aberration in a Cesarean section- (CS-) born person, e.g., infant, comprising the step of administrating a composition comprising at least one *Bacteroides* species, at least one *Bifidobacterium* species, and/or at least one *Akkermansia* species.

Intestinal microbiota aberration refers to any deviation in the intestinal microbiota composition in CS-born infants as compared to vaginally born infants. Any such deviation may be related to health risk, such as susceptibility to infections or disorders. Alternatively, the term intestinal microbiota dysbiosis may be used instead of intestinal microbiota aberration, i.e., referring to a microbiota composition with normally dominating species underrepresented and normally outcompeted or contained species increased to fill the void. With the term "infant," a subject, preferably a human, is meant under the age of 1.

*Bacteroides* is a genus of Gram-negative, obligate anaerobic bacteria. *Bacteroides* species are considered non endospore-forming bacilli, and may be either motile or non-motile, depending on the species. The DNA base composition is typically 40-48% GC. *Bacteroides* membranes typically contain sphingolipids. They may also contain meso-diaminopimelic acid in their peptidoglycan layer. The at least one *Bacteroides* species according to the present disclosure is/are preferably able to assimilate human milk oligosaccharides (HMOs).

The at least one *Bacteroides* species of the present disclosure preferably includes one or more of:

*Bacteroides* vulgatus (able to assimilate HMO), or strain having a 16S rRNA gene with at least 97, 98, 99, 100% sequence identity with the 16S rRNA gene sequence of the type strain of *Bacteroides* vulgatus (NCBI accession code M58762, SEQ ID NO:1);

*Bacteroides* thetaiotaomicron (able to assimilate HMO) or strain having a 16S rRNA gene with at least 97, 98, 99, 100% sequence identity with the 16S rRNA gene sequence of the type strain of *Bacteroides* thetaiotaomicron (NCBI accession code L16489, SEQ ID NO:2);

*Bacteroides fragilis* (able to assimilate HMO), or strain having a 16S rRNA gene with at least 97, 98, 99, 100% sequence identity with the 16S rRNA gene sequence of the type strain of *Bacteroides fragilis* (NCBI accession code M11656, SEQ ID NO:3);

*Bacteroides* caccae, or strain having a 16S rRNA gene with at least 97, 98, 99, 100% sequence identity with the 16S rRNA gene sequence of the type strain of *Bacteroides* caccae (NCBI accession code X83951, SEQ ID NO:4);

*Bacteroides* dorei, or strain having a 16S rRNA gene with at least 97, 98, 99, 100% sequence identity with the 16S rRNA gene sequence of the type strain of *Bacteroides* dorei (NCBI accession code AB242142, SEQ ID NO:5);

*Bacteroides* eggerthii, or strain having a 16S rRNA gene with at least 97, 98, 99, 100% sequence identity with the 16S rRNA gene sequence of the type strain of *Bacteroides* eggerthii (NCBI accession code NR040864, SEQ ID NO:6);

Bacteroidetes *distasonis* or strain having a 16S rRNA gene with at least 97, 98, 99, 100% sequence identity with the 16S rRNA gene sequence of the type strain of Bacteroidetes *distasonis* (NCBI accession code M86695, SEQ ID NO:7).

*Bifidobacterium* is a genus of gram-positive, typically non-motile, often branched anaerobic bacteria. They are ubiquitous inhabitants of the gastrointestinal tract, vagina and mouth of mammals, including humans. Bifidobacteria are one of the major genera of bacteria that make up the gastrointestinal tract microbiota in mammals. The at least one *Bifidobacterium* species according to the present disclosure is/are preferably able to assimilate human milk oligosaccharides (HMOs).

The at least one *Bifidobacterium* species of the disclosure preferably includes one or more of:

*Bifidobacterium infantis* (able to assimilate HMO), or strain having a 16S rRNA gene with at least 97, 98, 99, 100% sequence identity with the 16S rRNA gene sequence of the type strain of *Bifidobacterium infantis* (NCBI accession code D86184, SEQ ID NO:8);

*Bifidobacterium longum* (able to assimilate HMO), or strain having a 16S rRNA gene with at least 97, 98, 99, 100% sequence identity with the 16S rRNA gene sequence of the type strain of *Bifidobacterium longum* (NCBI accession code M58739, SEQ ID NO:9);

*Bifidobacterium breve* (able to assimilate HMO), or strain having a 16S rRNA gene with at least 97, 98, 99, 100% sequence identity with the 16S rRNA gene sequence of the type strain of *Bifidobacterium breve* (NCBI accession code AB006658, SEQ ID NO:10);

*Bifidobacterium thermophilum*, or strain having a 16S rRNA gene with at least 97, 98, 99, 100% sequence identity with the 16S rRNA gene sequence of the type strain of *Bifidobacterium thermophilum* (NCBI accession code AB016246, SEQ ID NO:11);

*Bifidobacterium bifidum*, or strain having a 16S rRNA gene with at least 97, 98, 99, 100% sequence identity with the 16S rRNA gene sequence of the type strain of *Bifidobacterium bifidum* (NCBI accession code M38018, SEQ ID NO:12);

*Bifidobacterium adolescentis*, or strain having a 16S rRNA gene with at least 97, 98, 99, 100% sequence identity with the 16S rRNA gene sequence of the type strain of *Bifidobacterium adolescentis* (NCBI accession code M58729, SEQ ID NO:13);

*Bifidobacterium catenulatum* or strain having a 16S rRNA gene with at least 97, 98, 99, 100% sequence identity with the 16S rRNA gene sequence of the type strain of *Bifidobacterium catenulatum* (NCBI accession code M58732, SEQ ID NO:14);

*Bifidobacterium pseudocatenulatum* or strain having a 16S rRNA gene with at least 97, 98, 99, 100% sequence identity with the 16S rRNA gene sequence of the type strain of *Bifidobacterium pseudocatenulatum* (NCBI accession code D86187, SEQ ID NO:15).

*Akkermansia* is a genus in the phylum Verrucomicrobia. It was found that *Akkermansia* species improve intestinal mucosal barrier function, or intestinal barrier function, which refers to the property of the intestinal mucosa that ensures adequate containment of undesirable luminal contents within the intestine while preserving the ability to absorb nutrients. Its role in protecting the mucosal tissues and circulatory system from exposure to pro-inflammatory molecules, such as microorganisms, toxins, and antigens is vital for the maintenance of health and well-being. Accordingly, *Akkermansia* species may prevent or be used for treating intestinal mucosal barrier dysfunction, which has been implicated in numerous health conditions such as: food allergy, microbial infection, irritable bowel syndrome, inflammatory bowel disease, celiac disease, metabolic syndrome, non-alcoholic fatty liver disease, diabetes, and septic shock. See Collado et al., 2007.

The at least one *Akkermansia* species of the disclosure preferably includes one or more of:

Akkermansia muciniphila (able to assimilate HMO) or strain having a 16S rRNA gene with at least 97, 98, 99, 100% sequence identity with the 16S rRNA gene sequence of the type strain of *Akkermansia muciniphila* (NCBI accession code AY271254, SEQ ID NO:16).

Akkermansia glycaniphila or strain having a 16S rRNA gene with at least 97, 98, 99, 100% sequence identity with the 16S rRNA gene sequence of the type strain of *Akkermansia glycaniphila* (NCBI accession code NR152695, SEQ ID NO:17).

Additionally or alternatively, the use according to the disclosure may be for reducing intestinal colonization of pathogenic microorganisms and/or for increasing resistance to intestinal colonization of pathogenic microorganisms and/or for decreasing relative abundance of pathogenic microorganisms in the intestine, for example, upon measurement after 1-12, 1-4, 2-8, 4-12 weeks or after 1-12 months or 1-12 years of CS. Pathogenic microorganisms are considered microorganisms that are associated with or causative of disease. In the disclosure, the pathogenic microorganisms may be particularly chosen from *Enterococcus* species, particularly *Enterococcus faecium, Enterococcus faecalis, Enterobacter* species, particularly *Enterobacter cloacae* and/or wherein the pathogenic microorganisms are chosen from *Klebsiella* species, particularly *Klebsiella pneumonia, Klebsiella oxytoca*, and/or wherein the pathogenic microorganisms are chosen from *Haemophilus influenza, Campylobacter jejuni, Salmonella enterica*.

Additionally or alternatively, the use according to the disclosure may be for increasing intestinal relative abundance of *Bacteroides* species and/or increasing intestinal relative abundance of *Akkermansia* species and/or increasing intestinal relative abundance of *Bifidobacterium* species and/or decreasing intestinal relative abundance of *Clostridium* species and/or decreasing relative abundance of Lactobacillales species, decreasing relative abundance of Clostridiales species, decreasing relative abundance of Clostridiaceae species and/or decreasing relative abundance of Enterobacteria, for example, upon measurement after 1-12, 1-4, 2-8, 4-12 weeks or after 1-12 months or 1-12 years of CS.

As many cells in the intestinal tract cannot be cultured easily, relative abundance can be determined by dividing the number of species (or genera) within the group of interest (e.g., based on 16S rRNA or metagenome based signals) by the total number of species (or genera) within all groups (e.g., based on 16S rRNA or metagenome based signals). Group may refer to genus level (genus) or order level (order).

Additionally or alternatively, the use according to the disclosure may be for reducing (later in life) susceptibility to a disorder chosen from the group consisting of:

metabolic syndrome, obesity or overweight, type 2 diabetes;

chronic inflammatory disease, inflammatory bowel disease, Crohn's disease and Ulcerative colitis, irritable bowel syndrome;

auto-immune disease, type 1 diabetes, rheumatoid auto-immune disease, rheumatoid arthritis, Bechterew's disease, thyroid autoimmune disease, Hashimoto's disease, Graves' disease, Addison's disease, Psoriasis, Vitiligo, celiac disease;

6 systemic connective disorder, systemic lupus erythematosus;

atopy-related disease, allergy, asthma, and eczema.

Additionally or alternatively, the use according to the disclosure may be for increasing (later in life) immune response to vaccine(s) (e.g., as measured by increased level of antigen specific antibodies in a blood sample, e.g., compared to the situation where the present use is not applied), for example, vaccine(s) against measles, mumps, rubella, diphtheria, tetanus, pertussis (whooping cough), poliomyelitis, *Haemophilus, influenzae* type B, human papillomavirus (adolescent/pre-adolescent girls), hepatitis A, Influenza, invasive disease caused by *Neisseria meningitidis*, invasive disease caused by *Streptococcus pneumoniae*, rotavirus, tuberculosis, and/or varicella.

Metabolic Syndrome

A person can be considered as having metabolic syndrome if a cluster of three out of five interconnected medical conditions appear together. According to the National Cholesterol Education Program (NCEP) Adult Treatment Panel III (ATP III) definition, and as used herein, metabolic syndrome is present if three or more of the following five criteria are met:

Waist circumference over 40 inches, or 102 cm (men) or over 35 inches, or 89 cm (women);

Blood pressure over 130/85 mmHg;

Fasting triglyceride (TG) level over 150 mg/dL;

Fasting high-density lipoprotein (HDL) cholesterol level below 40 mg/dL (men) or below 50 mg/dL (women); and Fasting blood sugar level over 100 mg/dL.

To measure fasting blood sugar (glucose) levels, fasting triglyceride levels, and fasting high-density lipoprotein cholesterol levels in the blood of a subject, blood is drawn from the subject after the subject has not eaten nor drank anything but water for at least 8 hours. The skilled person is familiar with the methods used to quantify these levels.

Obesity Overweight

Obesity is a medical condition in which excess body fat has accumulated to an extent that it may have a negative effect on health. People are generally considered obese when their body mass index (BMI), a measurement obtained by dividing a person's weight by the square of the person's height, is over 30 kg/m$^2$; the range 25-30 kg/m$^2$ is defined as overweight. For infants the BMI-Z score has been developed (see International Journal of Obesity volume 30, pages 590-594(2006). Body mass index z-scores, also called BMI standard deviation (s.d.) scores, are measures of relative weight adjusted for child age and sex. Given a child's age, sex, BMI, and an appropriate reference standard, a BMI z-score (or its equivalent BMI-for-age percentile) can be determined. For example, the US standard reference may be used (Centers for Disease Control and Prevention. CDC Growth Charts: United States. Available at: cdc.gov/growthcharts/). BMI-for-age percentiles above the 95th percentile in children and adolescents may be labeled "overweight," above the 96th, 97th, 98th, 99th may be labeled as "obese."

Inflammatory Bowel Disease (IBD)

Inflammatory bowel disease (IBD) is an umbrella term used to describe disorders that involve chronic inflammation of your digestive tract. Types of IBD include:

Ulcerative colitis. This condition causes long-lasting inflammation and sores (ulcers) in the innermost lining of your large intestine (colon) and rectum.

Crohn's disease. This type of IBD is characterized by inflammation of the lining of your digestive tract, which often spreads deep into affected tissues.

Both ulcerative colitis and Crohn's disease usually involve severe diarrhea, abdominal pain, fatigue, and weight loss. The disclosure may relate to ulcerative colitis and/or Crohn's disease.

Type ½ Diabetes Mellitus

The following diagnostic criteria can be applied for Type 1 and Type 2 Diabetes mellitus (American Diabetes Association, ADA):

A fasting plasma glucose (FPG) level ≥126 mg/dL (7.0 mmol/L), or

A 2-hour plasma glucose level ≥200 mg/dL (11.1 mmol/L) during a 75-g oral glucose tolerance test (OGTT), or A random plasma glucose ≥200 mg/dL (11.1 mmol/L) in a patient with classic symptoms of hyperglycemia or hyperglycemic crisis.

Additionally and/or alternatively, C-peptide response after a mixed meal test can be assessed, as described in the Example and/or as described by Lachin et al. (2011 PLoS ONE Vol. 6(11) e26471).

Type 1 Diabetes mellitus and/or its preceding symptoms can be confirmed by the presence of one or more autoimmune markers, which include islet (beta) cell autoantibodies, autoantibodies to insulin, autoantibodies to GAD (GAD65), autoantibodies to the tyrosine phosphatases IA-2 and IA-2β, and autoantibodies to zinc transporter 8 (ZnT8) as well as increased HbA1c and altered glucose tolerance.

Autoimmune Disease

Autoimmune diseases are a class of diseases in which the immune system produces an inappropriate response against a subject's own cells, tissues and/or organs. This may result in inflammation, damage and loss of function. Among the various autoimmune diseases, autoimmune endocrine disorders are most common and encompassed by the disclosure. The endocrine system comprises glands that produce hormones and deliver these directly into the circulatory system, as well as feedback loops to achieve homeostasis. The organs of the endocrine system can be affected by several autoimmune diseases, characterized by different impact and severity. Sometimes multiple organs are involved, such as in polyglandular autoimmune syndrome. Among the different autoimmune endocrine diseases, Type 1 Diabetes mellitus, Hashimoto's disease, Graves' disease, and Addison's disease are especially frequent in clinical practice.

Rheumatoid Arthritis

Rheumatoid arthritis (RA) can be seen as an autoimmune disease in which the immune system attacks the joints. This leads to inflammation that causes the tissue that lines the inside of joints (the synovium) to thicken, resulting in painful joints.

If not treated, RA can damage cartilage, the elastic tissue that covers the ends of bones in a joint, and even the bones themselves. Eventually, there can be loss of cartilage, joints can become loose, unstable, painful and lose their mobility, or even deform. Unfortunately, joint damage generally cannot be reversed, and therefore early diagnosis and treatment is recommended to control RA.

RA most commonly occurs in the joints of the hands, feet, wrists, elbows, knees and ankles. RA can also affect body systems, such as the cardiovascular or respiratory systems, and is then called systemic RA. In the early stages, people with RA may experience tenderness and pain in the joints.

No single test can definitely confirm RA, but blood tests can be performed that measure inflammation levels and look for biomarkers such as antibodies that are linked with RA.

A high erythrocyte sedimentation rate and a high C-reactive protein (CRP) level, in comparison to healthy individuals, are biomarkers of inflammation. A high ESR or high CRP is not specific to RA, but when combined with the presence of RA-related antibodies, can confirm RA diagnosis.

Rheumatoid factor (RF) is an antibody found in the majority of people with RA. Because RF can occur in other inflammatory diseases, it is not a definitive sign of having RA. However, a different antibody—anti-cyclic citrullinated peptide (anti-CCP)—occurs primarily in RA patients. That makes a positive anti-CCP test a stronger indication of RA. In addition, an X-ray, ultrasound or magnetic resonance imaging scan can be performed to look for joint damage, such as erosions and narrowing of joint space.

Bechterew's Disease

Bechterew's disease (or Ankylosing Spondylitis) is a chronic autoimmune rheumatoid disorder involving particularly the axial skeleton. Typically, it presents in male adults of 20-30 years of age.

The most serious symptoms are neck and lower back pain. A typical symptom is nocturnal pain, as well as inflammation of the sacroiliac joint. In some patients, bony deformities of the spine can occur, which may result in motion restriction. Apart from these spinal complaints, inflammation of peripheral joints is common.

In order to diagnose Bechterew's disease, examination of the vertebral column is performed to assess restrictions in cervical and lumbar spine mobility. A Schober test can be helpful in estimating the amount of lumbar forward flexion restriction. The diagnosis could be confirmed by discovery of HLA-B27 antigens in patient's blood.

Hashimoto's Disease

Hashimoto's disease is an organ specific autoimmune disorder with the highest occurrence. It is also referred to as Hashimoto's thyroiditis, or chronic lymphocytic thyroiditis and is regarded as an autoimmune disease in which the thyroid gland is gradually destroyed. The causes of Hashimoto's disease are still unclear, although an inappropriate cell-mediated immune response and autoantibody production against the thyroid gland are generally thought to be involved.

Until thyroid hypofunction becomes apparent, an enlargement of the thyroid is typically the only symptom. However, the disease can progress into hypothyroidism, thereby often leading to symptoms including edema, weight gain, and fatigability (susceptible to fatigue), sensitivity to cold and diarrhea, and physical findings such as dry skin, hoarseness, bradycardia, and/or a prolonged relaxation phase of the Achilles tendon reflex.

Hashimoto's disease may be confirmed by the presence of anti-thyroid peroxidase (TPO) antibodies and anti-thyroglobulin (Tg) antibodies in the patient's serum. Further, an elevated level of thyroid-stimulating hormone (TSH), and lowered levels of free T4 (FT4), lowered levels of free T3, and/or elevated levels of anti-microsomal antibodies, in comparison to the average in healthy individuals, can help obtain positive diagnosis.

Graves' Disease

Graves' disease is an autoimmune disease that affects the thyroid, and is the most common cause of hyperthyroidism. The disease can be characterized by the presence of autoantibodies in the serum that bind the thyrotropin receptor, i.e., the thyroid stimulating hormone (TSH) receptor. These anti-TSH receptor antibodies (TBII) overstimulate the thyroid gland, which may lead to goiter and signs of thyrotoxicosis as well as involvement of the eye muscles in a subset of patients (Graves' ophthalmopathy).

Among the symptoms are hyperthyroidism, goiter, and orbitopathy. Other major symptoms include weight loss (with increased appetite), fatigability, shortness of breath, hyperhidrosis, finger tremors, diarrhea, periodic paralysis (in male), and muscle weakness. With regard to Graves' ophthalmopathy, patients may suffer from proptosis of the eyes, blurred vision and dry/red eyes (in rare cases it can lead to blindness). Two signs are truly specific of Graves' disease and not seen in other hyperthyroid conditions: exophthalmos and pretibial myxedema.

Graves' disease may be confirmed by low serum TSH level (sometimes not detectable) and/or elevations in free T3 and free T4, in comparison to health individuals. Patients may typically be positive for anti-TSH receptor antibodies (TBII) in their serum.

Addison's Disease

Addison's disease is a chronic endocrine autoimmune disorder in which the adrenal glands do not produce sufficient steroid hormones. The disease is caused by destruction of the adrenal glands (both cortex and medulla produced hormones). The disease may be a manifestation of polyglandular autoimmune syndrome involving complications by other organ-specific autoimmune disorders (e.g., Type 1 Diabetes mellitus, Hashimoto's disease, Vitiligo).

Hyperpigmentation due to increased secretion of ACTH is a characteristic clinical sign of Graves' disease. Other symptoms include abdominal pain in the stomach region, orthostasis and weight loss.

Medical examination will typically determine if orthostasis, hypoglycemia, hyponatremia, hyperkalemia, and peripheral blood eosinophilia are present. To confirm Addison's disease, demonstration of low adrenal hormone levels even after stimulation (called the ACTH stimulation test or synacthen test) with synthetic pituitary ACTH hormone tetracosactide is generally performed for the diagnosis.

Psoriasis (Arthritis)

Psoriasis is a chronic autoimmune disease that leads to rapid production of skin cells. The underlying etiology is that T cells attack healthy skin cells, which causes the skin cell production process to go into overdrive. The new cells are pushed to the skin's surface, where they pile up. This results in the plaques and red inflamed areas of skin, which are most commonly associated with psoriasis. Subtypes of psoriasis include:

(1) Plaque psoriasis, which is the most frequently occurring type of psoriasis, is characterized by red, inflamed patches that cover areas of the skin, typically on the elbows, knees, and scalp. These patches are often covered with whitish-silver scales or plaques;

(2) Guttate psoriasis, which is the form of psoriasis that is common in children and causes small pink spots, typically on the torso, arms, and legs;

(3) Pustular psoriasis, which is the more common form of psoriasis in adults and causes white, pus-filled blisters and areas of red inflamed skin, typically on the hands or feet;

(4) Inverse psoriasis, which causes bright areas of red, shiny, inflamed skin. Patches of inverse psoriasis typically develop under armpits or breasts, in the groin, or around skinfolds;

(5) Erythrodermic psoriasis, which is a severe and rare type of psoriasis. This form often covers large sections of the body where the skin may appear sunburned. A person with this type of psoriasis may run a fever or become very ill, and this form of psoriasis can be life-threatening;

(6) Psoriatic arthritis with involvement of the joints.

Psoriasis symptoms are different among patients. Common symptoms include red patches of skin covered with thick, silvery scales, small scaling spots (commonly seen in children), dry, cracked skin that may bleed, itching, burning or soreness, thickened, pitted or ridged nails, and/or swollen and stiff joints. Most types of psoriasis can go through cycles, flaring for a few weeks or even months, then subsiding for a period or even going into remission. Psoriasis arthritis (or psoriatic arthritis) is a condition wherein swollen, sore joints of arthritis occur together with psoriasis.

Vitiligo

Vitiligo is a disease wherein white patches of skin appear on different parts of the body. It is generally thought that this is due to autoimmune processes that destroy the cells that make pigment (color) in the skin, i.e., melanocytes. Vitiligo can also occur in mucous membranes (such as inside the mouth and nose) and in the eye.

Recent studies reveal dysbiosis in the diversity of microbial community structure in the skin microbiome of vitiligo subjects. Although the individual specific microbiome signature is dominant over the vitiligo-specific microbiota, a clear decrease in taxonomic richness and evenness can be noted in lesional patches (Ganju et al., Sci. Rep. 2016 Jan. 13; 6:18761).

Ultraviolet (UV) light can be used particularly in the early phase of vitiligo for diagnosis and to determine the effectiveness of UV treatment. Skin with vitiligo, when exposed to UV, typically will glow blue. In contrast, healthy skin will show no reaction.

Celiac Disease

Celiac disease (or coeliac disease) is an autoimmune disorder where the ingestion of gluten leads to damage of the small intestinal epithelial cells. It may typically occur in genetically predisposed people and in combination with type 1 diabetes. Celiac disease and Type 1 Diabetes mellitus may have similar pathogenesis wherein heritable genetic factors as well as dietary and microbial exposures may play a role, particularly in early life (see, e.g., Verdu and Danska Nature Immunology|VOL 19|July 2018|685-695).

When people with celiac disease eat gluten (a protein found in wheat, rye and barley), their body initiates an immune response that attacks the small intestine, leading to damage of the villi (small fingerlike projections that line the small intestine). When the villi get damaged, nutrients cannot be absorbed properly by the intestine. Symptoms are abdominal cramps, malnutrition and osteoporosis.

There are several serologic (blood) tests available that screen for celiac disease antibodies, but the most commonly used is a tTG-IgA test. For this test to work, the patient must be consuming gluten. In addition, diagnosis for Celiac disease can be reached by an endoscopic biopsy. A biopsy is then taken of the small intestine, which can subsequently be analyzed to see if there is any damage consistent with celiac disease. The diagnosis may be confirmed when improvement is seen while on a gluten-free diet.

Systemic Lupus Erythematosus (SLE)

Systemic lupus erythematosus (SLE), is the most common type of lupus. SLE is an autoimmune disease in which the immune system attacks its own tissues, causing widespread inflammation and tissue damage in the affected organs. It can affect the joints, skin, brain, lungs, kidneys, and blood vessels.

People with SLE may experience a variety of symptoms that include fatigue, skin rashes, fevers, and pain or swelling in the joints. Among some adults, having a period of SLE symptoms—called flares—may happen every so often, sometimes even years apart, and go away at other times— called remission. However, other adults may experience SLE flares more frequently throughout their life. Other symptoms can include sun sensitivity, oral ulcers, arthritis, lung problems, heart problems, kidney problems, seizures, psychosis, and blood cell and immunological abnormalities.

SLE is diagnosed by a health care provider using symptom assessments, physical examination, X-rays, and lab tests. SLE may be difficult to diagnose because its early signs and symptoms are not specific and can look like signs and symptoms of other diseases.

Asthma

In the context of the disclosure, the prevention of asthma is also foreseen, in view of autoimmune mechanisms that might be operating in asthma as well. Moreover, aberrations in early life have been shown to predispose for the development of asthma that only can be diagnosed at an age of approximately 5 years (Korpela Nat. Commun.).

Asthma is a common chronic inflammatory disease of the airways of the lungs. It can be characterized by reversible airflow obstruction and bronchospasm. Symptoms include episodes of coughing, wheezing, chest tightness, and shortness of breath.

There is currently no definitive diagnostic test for asthma, and diagnosis is typically based on the pattern of symptoms and response to therapy over time. A diagnosis of asthma can be made if there is a history of recurrent wheezing, coughing or difficulty breathing and these symptoms occur or worsen due to exercise, viral infections, allergens and/or air pollution; also FEV1 test upon bronchodilators are done to study effect on lung function.

The effectiveness of the treatment according to the disclosure confirms a link between intestinal microbiome composition and risk of developing asthma, which has been postulated by Korpela et al. (Nat. Commun. 2016 Jan. 26; 7:10410).

Other Conditions

The disclosure may also be used in the context of preventing other autoimmune diseases, particularly including autoimmune hepatitis, Diabetes mellitus Type 1a and/or 1b, polyglandular autoimmune syndrome, Guillain-Barre syndrome, Multiple sclerosis, Myasthenia gravis, Pernicious anemia, Primary biliary cirrhosis, Sclerosing cholangitis, Antiphospholipid antibody syndromes, Dermatomyositis, Mixed connective tissue disease, Polymyalgia rheumatica, Polymyositis, Scleroderma, and Sjögren's syndrome.

Additionally, the composition according to the disclosure may be used to prevent an allergy, also known as allergic diseases, which are conditions caused by hypersensitivity of the immune system to typically harmless substances in the environment. Common allergies include hay fever (plant pollen allergy) and food allergy (relating, e.g., to cow's milk, soy, eggs, wheat, peanuts, tree nuts, fish, and/or shellfish).

The disclosure may also allow for the prevention of the following diseases: gastrointestinal disorders, *Clostridium difficile* infection, Morbus Crohn (Crohn's disease), Colitis Ulcerosa or Inflammatory Bowel Disease (IBD), and/or Irritable bowel syndrome (IBS).

Additionally or alternatively, the use according to the disclosure may be for increasing immune programming, preferably as measured by increased level of intestinal secretory IgA and/or increased level of intestinal (innate immunity) antimicrobial peptides, e.g., in comparison to a control wherein the use according to the disclosure is not applied. This may be measured, for example, after 1-12, 1-4, 2-8, 4-12 weeks or after 1-12 months or 1-12 years of CS. In particular, it was found that the disclosure allows for an (improved) induction of immune defense programming, e.g., relative to not administering the composition according to the disclosure, or relative to administering vaginal fluid sample.

Levels of sIgA and of innate immunity antimicrobial peptides such as α-defensins (HNP 1-3), β-defensin 2 (HBD-2) and cathelicidin LL-37 can be measured in fecal samples. For example, for secretory immunoglobulin A (sIgA) and beta-defensin 2 (HBD-2), 1 g of fecal sample can be diluted 1:1 (w/v) with PBS buffer (130 mM NaCl and 10 mM sodium phosphate-buffered saline, pH 7.4). For alpha-defensins (HNP 1-3): 1 g of fecal sample can be diluted 1:0.5 (w/v) with the same buffer. The sample can then be centrifuged at 13,000 rpm for 15 min in 1.5-ml tubes. The supernatant can be collected for quantification by ELISA, without further dilution. HNP 1-3 can be measured by ELISA using a specific human kit (Hycult Biotechnology, Uden, The Netherlands), HBD-2 by ELISA using a specific human kit (Phoenix Pharmaceuticals, Inc., Burlingame, CA, USA) (detection limit: 0.01 ng/g) and sIgA by indirect enzyme immunoassay for human samples (Salimetrics LLC, Carlsbad, CA, USA) (detection limit: 2.5 µg/g). For LL-37 measurement, the sample (1 g of fecal sample) can be extracted with 60% acetonitrile in 1% aqueous trifluoroacetic acid (TFA) and then extracted overnight at 4° C. The extract can then be centrifuged, and the supernatant stored at −20° C. LL-37 level can then be measured, without dilution, by a commercially available ELISA kit specific for human samples (Hycult Biotechnology, Uden, The Netherlands) (detection limit: 0.1 ng/g).

Additionally or alternatively, the use according to the disclosure may be for improving general health and/or reducing inflammation status, the latter preferably measured by a decreased level of C-reactive protein, e.g., relative to not administering the composition according to the disclosure. C-reactive protein may, for example, be measured after 1-12, 1-4, 2-8, 4-12 weeks or after 1-12 months or 1-12 years of CS. C-reactive protein (CRP) is a protein made by the liver. CRP levels in the blood increase when there is a condition causing inflammation somewhere in the body. A CRP test measures the amount of CRP in the blood to detect inflammation status.

Additionally or alternatively, the use according to the disclosure may be for increasing intestinal microbial diversity, preferably as measured by increased inverse Simpson diversity index, relative to not administering the composition according to the disclosure. The increased inverse Simpson diversity index may be above 2.5 OTUs at, e.g., 12 weeks after CS. The inverse Simpson diversity index may be calculated as shown below:

$$D = \frac{1}{\sum_{i=1}^{s} p_i^2}$$

wherein s represents the total number of species within a community and $p_i$ represents relative abundance. Essentially, each of the relative abundance values (represented by OTU i) for a given species within the community are summed, and then the inverse of this sum is taken.

The composition for use according to the disclosure may be or be derived from fecal matter, e.g., obtained from one or more donor subjects (not autologous to the CS-born infant). The term "donor" as used herein denotes a subject who donates fecal matter. The fecal matter according to the disclosure is thus derived from the donor and may be administered to a recipient, i.e., the CS-born infant. Optionally after processing, the fecal matter is administered to the CS-born infant. The one or more donor subjects are preferably mammal, preferably human. Also the CS-born infant is preferably a mammal, preferably a human.

Selected donor subjects preferably have a BMI between 18-27, preferably between 20 to 25 kg/m². The term "Body Mass Index" or "BMI" as used herein denotes a value derived from dividing the mass of a person by the square of the person's body height, expressed in kg/m².

Selected donor subjects preferably have an age below 30 years or below 35 years. The at least one donor subject, for example, has an age between 18 and 30 years, such as 20 to 25 years.

Additionally or alternatively, the at least one donor subject preferably does not carry group B *Streptococcus*, human immunodeficiency virus (HIV), SARS-CoV-2 (COVID-19), human T-cell lymphotropic virus, *Treponema pallidum*, hepatitis A, B, C, and E, protozoa, helminths, *Entamoeba histolytica, Clostridium difficile*, enteric pathogens particularly *Salmonella, Shigella, Campylobacter, Vibrio cholera*, pathogenic *Escherichia coli* strains particularly EHEC, ETEC, EPEC, BIEC, EAEC, *Helicobacter pylori*, norovirus, *Giardia lamblia, Cryptosporidium parvum*, Methicillin-resistant *Staphylococcus aureus* (MRSA), Gram-negative multidrug-resistant (MDR) bacteria and vancomycin-resistant enterococci (VRE). Additionally or alternatively, the at least one donor subject has a relative abundance of *Bacteroidales* species of at least 0.1, 0.2, 0.3, 0.4, 0.5, 0.6, 0.7, 0.8, 0.9 or 1, 2, 3, 4, 5, 6, 7, 8, 9, 10, 11, 12, 13, 14, 15, 16, 17, 18, 19, 20, 25, 30% and/or a relative abundance of *Bifidobacteriales* species of at least 0.1, 0.2, 0.3, 0.4, 0.5, 0.6, 0.7, 0.8, 0.9 or 1, 2, 3, 4, 5, 6, 7, 8, 9, 10, 15, 20, 25, 30% (as compared to the number of species of other genera). Additionally or alternatively, the at least one donor subject has a relative abundance of *Akkermansia* species of at least 0.1, 0.2, 0.3, 0.4, 0.5, 0.6, 0.7, 0.8, 0.9 or 1, 2, 3, 4, 5, 6, 7, 8, 9, 10, 15, 20, 25, 30% (as compared to the number of species of other genera).

Accordingly, the disclosure may involve, in a preferred embodiment, determining in one or more samples (e.g., blood sample, fecal sample, perianal/cervical swab sample where appropriate) obtained from one or more subjects of one or more of: group B *Streptococcus*, human immunodeficiency virus (HIV), SARS-CoV-2 (COVID19), human T-cell lymphotropic virus, *Treponema pallidum*, hepatitis A, B, C, and E, protozoa, helminths, *Entamoeba histolytica, Clostridium difficile*, enteric pathogens particularly *Salmonella, Shigella, Campylobacter, Vibrio cholera*, pathogenic *Escherichia coli* strains particularly EHEC, ETEC, EPEC, EIEC, EAEC, *Helicobacter pylori*, norovirus, *Giardia lamblia, Cryptosporidium parvum*, Methicillin-resistant *Staphylococcus aureus* (MRSA), Gram-negative multidrug-resistant (MDR) bacteria and vancomycin-resistant enterococci (VRE), relative abundance of *Bacteroidales* species, relative abundance of *Bifidobacteriales* species, relative abundance of *Akkermansia* species and/or determining BMI, age; and subsequent selection of one or more donor subjects not carrying one or more of group B *Streptococcus*, human immunodeficiency virus (HIV), SARS-CoV-2 (COVID19), human T-cell lymphotropic virus, *Treponema pallidum*, hepatitis A, B, C, and E, protozoa, helminths, *Entamoeba histolytica, Clostridium difficile*, enteric pathogens particularly *Salmonella, Shigella, Campylobacter, Vibrio cholera*, pathogenic *Escherichia coli* strains particularly EHEC, ETEC, EPEC, EIEC, EAEC, *Helicobacter pylori*, norovirus, *Giardia lamblia, Cryptosporidium parvum*, Methicillin-resistant *Staphylococcus aureus* (MRSA), Gram-negative multidrug-resistant (MDR) bacteria and vancomycin-resistant enterococci (VRE), and/or having a relative abundance of *Bacteroidales* species of at least 0.1, 0.2, 0.3, 0.4, 0.5, 0.6, 0.7, 0.8, 0.9 or 1, 2, 3, 4, 5, 6, 7, 8, 9, 10, 11, 12, 13, 14, 15, 16, 17, 18, 19, 20, 25, 30% and/or a relative abundance of *Bifidobacteriales* species of at least 0.1, 0.2, 0.3, 0.4, 0.5, 0.6, 0.7, 0.8, 0.9 or 1, 2, 3, 4, 5, 6, 7, 8, 9, 10, 11, 12, 13, 14, 15, 16, 17, 18, 19, 20, 25, 30% and/or relative abundance of *Akkermansia* species of at least 0.1, 0.2, 0.3, 0.4, 0.5, 0.6, 0.7, 0.8, 0.9 or 1, 2, 3, 4, 5, 6, 7, 8, 9, 10, 15, 20, 25, 30% and/or having an age of between 18 and 30 years, such as 20 to 25 years and/or having a BMI of between 18-27, preferably between 20 to 25 kg/m².

Additionally and/or alternatively, the disclosure may involve determining antibiotic use of one or more subjects (i.e., in the preceding 1, 2, 3, 4, 5, 6 months); and subsequent selection of one or more donor subjects not having used antibiotics in the preceding 1, 2, 3, 4, 5, 6 months or 1, 2, 3, 4, 5, 6, 7, 8, 9, 10 years, for example, as measured by determining normal (not decreased) expression of bile-salt hydrolase genes in fecal microbiota, or higher expression of the genes in fecal microbiota as compared to a reference, e.g., the expression of the genes in fecal microbiota as, e.g., determined in a sample obtained from a subject known to have used antibiotics in the preceding 1, 2, 3, 4, 5, 6 months or 1, 2, 3, 4, 5, 6, 7, 8, 9, 10 years. With "preceding" is meant preceding to the moment of measurement. Recent (e.g., within last year) antibiotic use is associated with a decrease in expression of bile-salt hydrolase genes in comparison to no (recent) antibiotic use. Similarly, the recent (e.g., within last year) use of antibiotics, for example, can be measured by determining the normal (not increased) expression of antibiotic-resistance genes, notably these providing resistance to macrolides, such as erythromycin or related antibiotics such as clarithromycin, azithromycin, fidaxomicin and telithromycin.

qPCR analyses can be performed to quantify the abundances of these genes in a fecal sample. Quantification of bacterial genes bsh, ermB and ermF can be performed with primers as, for example, specified in the Supplementary Table 4 of Korpela et al., 2016. The primers for ermB and ermF genes have been previously published (Chen et al., 2007).

Group B *Streptococcus* may be determined in perianal/cervical swab sample or fecal sample as known by the skilled person. Human immunodeficiency virus (HIV), human T-cell lymphotropic virus, *Treponema pallidum*, hepatitis A, B, C, and E may be determined in a blood sample as known by the skilled person. Protozoa, helminths, *Entamoeba histolytica, Clostridium difficile*, enteric pathogens (*Salmonella, Shigella, Campylobacter, Vibrio cholera*, pathogenic *Escherichia coli* strains EHEC, ETEC, EPEC, EIEC, EAEC, *Helicobacter pylori*, norovirus, *Giardia lamblia, Cryptosporidium parvum*. Methicillin-resistant *Staphylococcus aureus* (MRSA), Gram-negative multidrug-resistant (MDR) bacteria and vancomycin-resistant enterococci (VRE), relative abundance of *Bacteroidales* species, relative abundance of *Bifidobacteriales* species, and relative abundance of *Akkermansia* species may be determined in a fecal sample as known by the skilled person.

In a particularly preferred embodiment, the donor subject is the mother of the CS-born infant and/or the composition according to the disclosure may be maternal fecal matter. Preferably the fecal matter is obtained from the mother of the CS-born infant at most 12, 11, 10, 9, 8, 7, 6, 5, 4 preferably at most 3, 2, 1 weeks prior to the CS and/or not within 5, 4, 3, 2, 1 months, 4, 3, 2, 1 week following antibiotic use. Typically, antibiotics are administered to the mother upon CS delivery. In view thereof, it is highly preferred that the maternal fecal matter is obtained prior to CS. However, it is also foreseen that the composition according to the disclosure is not maternal fecal matter and/or does not comprise maternal fecal matter, for example, in case the mother of the CS-born infant carries any of the pathogens as mentioned in the preceding paragraph. The at least one donor subject alternatively may be or include the father of the CS-born infant, the grandmother, and/or grandfather of the CS-born infant. Similarly, a sibling of the pregnant mother may be envisaged.

In case the composition for use according to the disclosure is or comprises, or is derived from, (maternal) fecal matter, the composition preferably comprises between 0.1-5 mg, preferably between 0.1-3 mg, or 0.1-2.9 mg, more preferably between 0.1-2 mg most preferably between 0.1-1 mg fecal matter and/or the composition comprises between $1 \times 10^4$ and $1 \times 10^9$, $1 \times 10^5$ and $1 \times 10^8$, preferably between $5 \times 10^5$ and $5 \times 10^7$, more preferably between $0.5 \times 10^6$ and $20 \times 10^6$ bacterial cells.

The fecal matter according to the disclosure can be feces, i.e., excreta discharged from the intestine (anus), such as (morning) stool, or part thereof, and/or a composition derived therefrom. The fecal matter may be purified, suspended in medium, filtered, centrifuged, or otherwise processed such as stabilized and freeze-dried to obtain a composition suitable for oral administration or for administration in the gastro-intestinal tract of a receiving subject.

In one aspect of the disclosure, the fecal matter comprises a total of at least 5, 6, 7, 8, 9, 10, 11, 12 different phyla selected from bacterial phyla and archaeal phyla, preferably at least 16 different phyla, more preferably at least 18 different phyla, most preferred between 20 and 34 different phyla. A total number of phyla can be determined by 16S rRNA amplicon sequencing as described in Clarke et al., Exercise and associated dietary extremes impact on gut microbial diversity, Gut microbiota, 2014.

The phyla can be selected from a group comprising the bacterial phyla: Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia; and/or a group comprising the archaeal phyla: Crenarchaeota, Euryarchaeota, Korarchaeota, Nanoarchaeota, and Thaumarchaeota. Preferably, the fecal matter according to the disclosure comprises the phyla Bacteroidetes, Firmicutes, Proteobacteria, Actinobacteria and/or Verrucomicrobioa (and Eurachaeyota).

In a particularly preferred embodiment, the composition for use according to the disclosure is comprised in breast milk or pasteurized bank milk and/or administered to the CS-born infant within at most 1, 2, 3, 4, 5, 6, 7 days or at most 1, 2, 3, 4, 5, 6, 7, 8, 9, 10, 11, 12, 12, 14, 15, 16, 17, 18, 19, 20, 21, 22, 23, 24 hours after CS, e.g., CS surgery.

Preferably, in case the composition according to the disclosure is fecal matter, the fecal matter can be feces or part thereof, preferably a purified part thereof. By purifying the fecal matter, the fecal matter can be more conveniently administered. In a particular embodiment, 50-150 mg fecal matter sample may be combined with 5-15 mL isotonic saline containing, e.g., 10% glycerol and can be frozen at −80° C. until delivery. For example, 1 mL may be mixed with mother's own milk or pasteurized bank milk to a total volume of 10 mL, and 5 mL can be administered to the CS-born infant.

A part of fecal matter as used herein denotes one or more specific groups of components including, but not limited to: enzymes, proteins, lipids, molecules, microorganisms, viruses, bacteria, fungi, yeast, archaea, compounds, complexes, solids, liquids, particles, and fibers.

A purified part of fecal matter as used herein denotes that undesired groups of components are not present in the fecal matter.

Preferably, the fecal matter for use according to the disclosure is comprised in liquid medium and/or does not comprise solids having a diameter of more than 10, 25, 50, 75, 100, 200, 400, 600, 800, or 1000 μm, preferably obtained by mixing allogenic feces with aqueous medium and subsequent filtering and/or centrifugation. This greatly reduces the viscosity and enhances flow of the fecal matter, facilitating administration of the fecal matter to the receiving subject. The liquid medium can comprise water, or another type of liquid that may be supplemented with other components, such as salts, to provide an isotonic solution.

According to one aspect of the disclosure, the fecal matter according to the disclosure is comprised in a composition, such as a pharmaceutical composition, more preferably a liquid dosage form, facilitating administration of the fecal matter to a recipient.

It is further envisaged that the fecal matter according to the disclosure is present in lyophilized and/or microencapsulated form (to protect from gastric environment). The use according to the disclosure may involve 1, 2, 3, 4, 5, 6, 7, 8, 9, 10 separate administrations of fecal matter obtained from the at least one donor subject to the recipient, preferably with intervals of at least 1, 2, 3, 4, 5, 6, 7, 8 weeks between the separate administrations.

The composition according to the disclosure may be administered by enteral, preferably by oral, nasal or rectal administration, and/or by nasoduodenal tube administration.

The composition according to the disclosure may be used as medicament and/or accompanied by a physiologically acceptable carrier, which may be any inert carrier. For instance, non-limiting examples of suitable physiologically or pharmaceutically acceptable carriers include any well-known physiological or pharmaceutical carriers, buffers, diluents, and excipients. It will be appreciated that the choice for a suitable physiological carrier will depend upon the intended mode of administration of the composition as taught herein (e.g., oral). The skilled person knows how to select a physiologically acceptable carrier that is suitable for or compatible with the compositions for use as taught herein.

It is envisaged that the composition according to the disclosure is comprised in and/or encapsulated by an (enteric) coating, preferable wherein the coating does not dissolute and/or disintegrate in the gastric environment of the recipient. Such coating may help the composition to reach the intended site for delivery, e.g., the duodenum, without suffering breakdown due to the acidic environment of the stomach. Preferred (enteric) coatings work by presenting a surface that is stable at the highly acidic pH found in the stomach, but breaking down more rapidly at a lower pH. For example, it will not dissolve in the gastric acids of the stomach (pH~3), but it will dissolve in the alkaline (pH 7-9) environment present in the small intestine, or duodenum.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

BRIEF DESCRIPTION OF THE DRAWINGS

FIG. 1A shows group means and FIG. 1B shows group means and standard errors of the mean. FIG. 1C shows Inverse Simpson diversity, number of OTUs clustered at 97% similarity (species richness), and number of species with relative abundance >0.1% are shown (species richness >0.1%) is shown as means and standard errors of means. To prevent overlap of the data points, some small shifts in the time axis were introduced—discrete time points are at 0 (meconium), 2 days, 7 days, 2 weeks, 3 weeks, 4 weeks, 12 weeks. Significance of the difference between the FMT-treated and non-treated CS groups to the vaginally delivered group was tested at 1, 3, and 12 weeks. The significance is shown as asterisks: * $p<0.05$,  $p<0.01$; * $p<0.0001$.

---

SEQUENCE LISTING

Figure 1A:
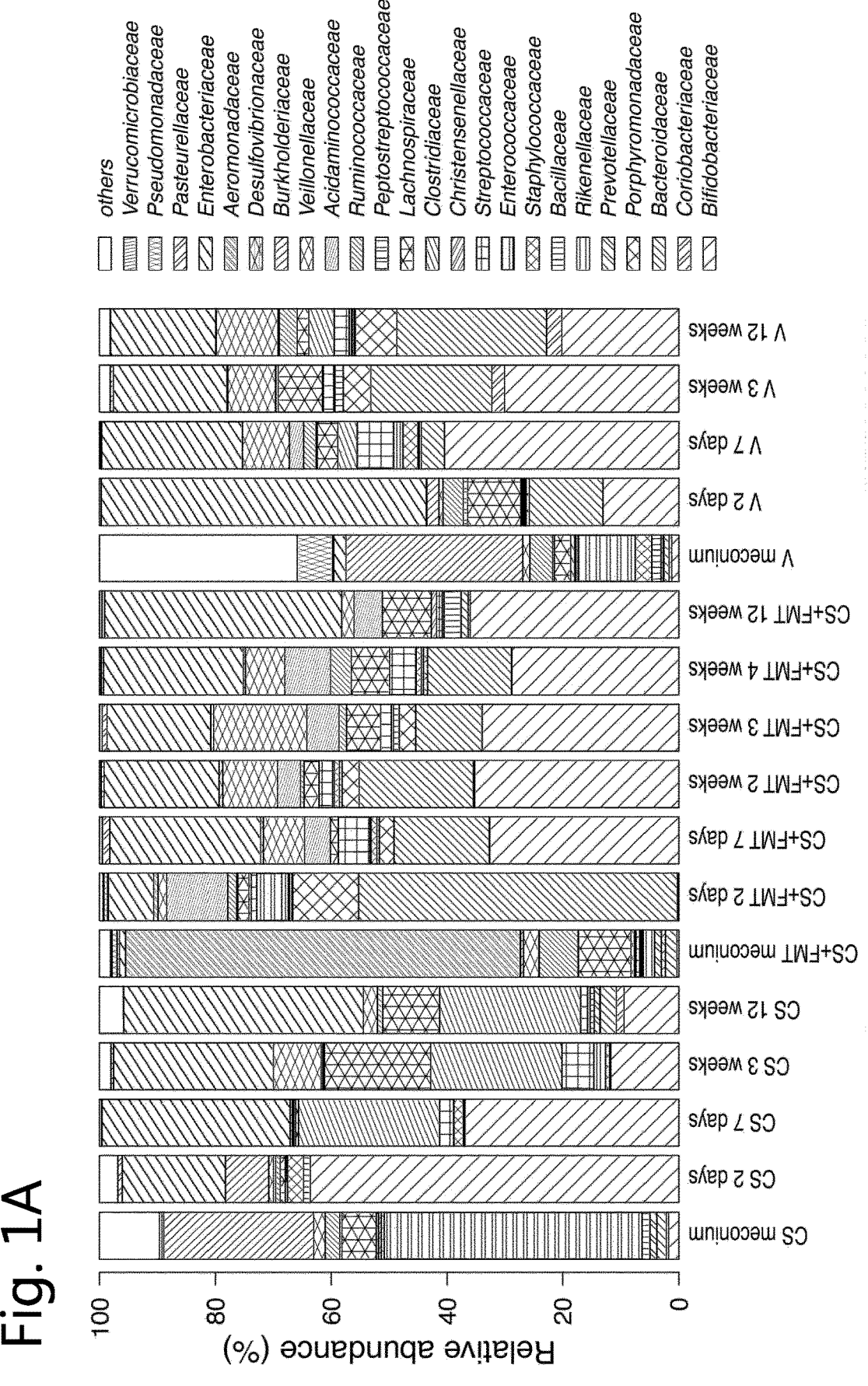
FIGS. 1A-1C: Average relative bacterial abundance, diversity and richness in the FMT treated infants, compared with the non-treated CS and vaginally delivered Finnish infants at different ages. Dominant bacterial families (FIG. 1A) and orders (FIG. 1B) are shown as means, while FIG. 1B also includes the combined relative abundance of the potential pathogens, *Enterococcus faecium*, *Enterococcus faecalis*, *Enterobacter cloacae*, *Klebsiella pneumoniae*, *Klebsiella oxytoca*, *Haemophilus influenza*, *Campylobacter jejuni* and *Salmonella enterica* (see Shao et al., 2019).

*Bacteroides vulgatus* 16S rRNA gene (NCBI/Genbank accession code M58762, SEQ ID NO: 1)

```
   1 tattacaatg aagagtttga tcctggctca ggatnaacgc tagctacagg cttaacacat
  61 gcaagtcgag gggcagcatg gtcttagctt gctaagncna tggcgaccgg cgcacgggtg
 121 agtaacacgt atccaacctg ccgtctactc ttggacagcc ttctgaaagg aagattaata
 181 caagatggca tcatgagtcc gcatgttcac atgattaaag gtattccggt agacgatggg
 241 gatgcgttcc attagatagt aggcggggta acggcccacc tagtcttcga tggatagggg
 301 ttctgagagg aaggtccccc acattggaac tgagacacgg tccaaactcc tacgggaggc
 361 agcagtgagg aatattggtc aatgggcgag agccngaacc agccaagtag cgtgaaggat
 421 gactgcccta tgggttgtaa acttcttta taaaggaata aagtcgggta tggatacccg
 481 nttgcatgta ctttatgaat aaggatcggc taactccgtg ccagcagccg cggtaatacg
 541 gagnatccga gcgttatccg gatttattgg gtttaaaggg agcgtagatg gatgtttaag
 601 tcagttgtga aagtttgcgg ctcaaccgta aaattgcagt tgatactgga tatcttgagt
 661 gcagttgagg caggcggaat tcgtggtgta gcggtgaaat gcttagatat cacgaagaac
 721 tccgattgcg aaggcagcct gctnagctgc aactgacatt gaggctcgaa agtgtgggta
 781 tcaaacagga ttagataccc tggtagtcca cacggtaaac gatgaatact cgctgtttgc
 841 gatatactgc aagcggccaa gcgaaagcgt taagtattcc acctggggag tacgccggca
 901 acggtgaaac tcaaaggaat tgacgggggc cngcacaagc ggaggaacat gtggtttaat
 961 tcgatgatac gcgaggaacc ttacccgggc ttaaattgca gatgaattac ggtgaaagcc
1021 gtaagccgca aggcatctgt gaaggtgctg catggttgtc gtcagctcgt gccgtgaggt
1081 gtcggcttaa gtgccataac gagcgcaacc cttgttgtca gttactaaca ggttatgctg
1141 aggactctga caagactgcc atcgtaagat gtgaggaagg tggggatgac gtcaaatcag
1201 cacngccctt acgtccgggg ctacacacgt gttacaatgg ggggtacaga gggcngctac
1261 cacgcgagtg gatgccaatc cccaaaacct ctctcagttc ggactggagt ctgcaacccg
1321 actccacgaa gctggattcg ctagtaatcg cgcatcagcc acggcgcggt gaatacgttc
1381 ccgggccttg tacacaccgc ccgtcaagtc atgggagccg ggggtacctg aagtgcgtaa
1441 ccgcgaggag cgccctaggg taaaactggt gactggggct aagtcgtaac aaggtagcng
1501 taccggaagn nnnnnnnnga acacctcctt tct
```

*Bacteroides thetaiotaomicron* 16S rRNA gene (NCBI/Genbank accession code L16489, SEQ ID NO: 2)

```
   1 cantgaagag tttgatcctg gctcaggatn aacgctagct acaggcttaa cacatgcaag
  61 tcgaggggca gcatttcnnt ttgcttgcaa actnnagatg gcgaccggcg cacgggtgag
 121 taacacgtat ccaacctgcc gataactcgg ggatagcctt tcgaaagaaa gattaatacc
 181 cgatggcata atcanaccgc atggtcttat tattaaagaa tttcggttat cgatggggat
 241 gcgttccatt aggcagttgg tgaggtaacg gctcacnaaa ccttcgatgg atagggggttc
 301 tgagaggaag gtcccccaca ttggaactga gacacggtcc naactcctac gggaggcagc
 361 agtgaggaat attggtcaat gggcgcaggc ctnaaccagc caagtagcgt gaaggatgac
 421 tgccctatgg gttgtaaact nctnttatat gggaataaag tnttccacgt gtggaatttt
 481 gtatgtacca tatgaataag gatcggctaa ctccgtgcca gcagccgcgg tnatacggag
 541 gatccgagcg ttatccggat ttattgggtt taaagggagc gtaggtggac agttaagtca
 601 gttgtgaaag tttgcggctc aaccgtaaaa ttgcagttga tactggctgt cttgagtaca
 661 gtagaggtgg gcggaattcg tggtgtagcg gtgaaatgct tagatatcac gaagaactcc
 721 gattgcgaag gcagctcact ggactgcaac tgacactgat gctcgaaagt gtgggtatca
 781 aacaggatta gataccctgg tagtccacac agtaaacgat gaatactcgc tctttgcgat
 841 atacagtaag cggccaagcg aaagcattaa gtattccacc tggggagtac gccggcaacg
 901 gtgaaactca aaggaattga cgggggcccg cacaagcgga ggaacatgtg gtttaattcg
```

-continued

SEQUENCE LISTING

```
 961 atgatacgcg aggaacctta cccgggctta aattgcattt gaataatctg gaaacaggtt
1021 agccgcaagg caaatgtgaa ggtgctgcat ggttgtcgtc agctcgtgcc gtgaggtgtc
1081 ggcttaagtg ccataacgag cgcaaccctt atctttagtt actaacaggt catgctgagg
1141 actctagaga gactgccgtc gtaagatgtg aggaaggtgg ggatgacgtc aaatcagcac
1201 ggcccttacg tccggggcta cacacgtgtt acaatggggg gtacagaagg cagctacctg
1261 gtgacaggat gctnatccca aaagcctctc tcagttcgga tcgaagtctg caacccgact
1321 tcgtgaagct ggattcgcta gtaatcgcgc atcagccatg gcgcggtgaa tacgttcccg
1381 ggccttgtac acaccgcccg tcaanccatg anagccgggg gtacctgaag tacgtaaccg
1441 caaggagcgt cctagggtaa aactggtaat tgggg
```

*Bacteroides fragilis* 16S rRNA gene (NCBI/Genbank accession code M11656, SEQ ID NO: 3)

```
   1 ttacaacgaa gagtttgatc ctggctcagg atgaacgcta gctacaggct taacacatgc
  61 aagtcgaggg gcatcaggaa gaaagcttgc tttctttgct ggcgaccggc gcacgggtga
 121 gtaacacgta tccaacctgc cctttactcg gggatagcct tcgaaagaa agattaatac
 181 ccgatagcat aatgattccg catggtttca ttattaaagg attccggtaa aggatgggga
 241 tgcgttccat taggttgttg gtgaggtaac ggctcaccaa gccttcgatg gataggggtt
 301 ctgagaggaa ggtcccccac attggaactg agacacggtc caaactccta cgggaggcag
 361 cagtgaggaa tattggtcaa tgggcgctag cctgaaccag ccaagtagcg tgaaggatga
 421 aggctctatg ggtcgtaaac ttctttttata taagaataaa gtgcagtatg tatactgttt
 481 tgtatgtatt atatgaataa ggatcggcta actccgtgcc agcagccgcg gtaatacgga
 541 ggatccgagc gttatccgga tttattgggt ttaaagggag cgtaggtgga ctggtaagtc
 601 agttgtgaaa gtttgcggct caaccgtaaa attgcagctg atactgtcag tcttgagtac
 661 agtagaggtg ggcggaattc gtggtgtagc ggtgaaatgc ttagatatca cgaagaactc
 721 cgattgcgaa ggcagctcac tggactgcaa ctgacactga tgctcgaaag tgtgggtatc
 781 aaacaggatt agataccctg gtagtccaca cagtaaacga tgaatactcg ctgtttgcga
 841 tatacagtaa gcggccaagc gaaagcatta agtattccac ctggggagta cgccggcaac
 901 ggtgaaactc aaaggaattg acgggggccc gcacaagcgg aggaacatgt ggtttaattc
 961 gatgatacgc gaggaacctt acccgggctt aaattgcagt ggaatgatgt ggaaacatgt
1021 cagtgagcaa tcaccgctgt gaaggtgctg catggttgtc gtcagctcgt gccgtgaggt
1081 gtcggcttaa gtgccataac gagcgcaacc cttatcttta gttactaaca ggttatgctg
1141 aggactctag agagactgcc gtcgtaagat gtgaggaagg tggggatgac gtcaaatcag
1201 cacggcccct tacgtccggg ctacacacgt gttacaatgg ggggtacaga aggcagctag
1261 cgggtgaccg tatgctaatc ccaaaatcct ctctcagttc ggatcgaagt ctgcaacccg
1321 acttcgtgaa gctggattcg ctagtaatcg cgcatcagcc acggcgcggt gaatacgttc
1381 ccgggccttg tacacaccgc ccgtcaagcc atgggagccg ggggtacctg aagtacgtaa
1441 ccgcaaggat cgtcctaggg taaaactggt gactgggggc aagtcgtaac aaggtagccg
1501 taccggaagg tgcggctgga cacctcctt tct
```

*Bacteroides caccae* 16S rRNA gene (NCBI/Genbank accession code X83951, SEQ ID NO: 4)

```
   1 atgaacgcta gctacaggct taacacatgc aagtcgaggg gcatcagttt gtttgcttgc
  61 aaacaaacgc tggcgaccgg cgcacgggtg agtaacacgt atccaaccta cctcatactc
 121 ggggatagcc tttcgaaaga aagattaata tccgatagca tatatttccc gcatgggtnn
 181 natattaaag aaattcggta tgagatgggg atgcgttcca ttagtttgtt gggggggtaa
 241 cggcccacca agactacgat ggataggggt tctgagagga aggtccccca cattggaact
 301 gagacacggt ccaaactcct acgggaggca gcagtgagga atattggtca atggacgcga
 361 gtctgaacca gccaagtagc gtgaaggatg actgccctat gggttgtaaa cttctttttat
 421 atgggaataa agtggtccac gtgtggactt ttgtatgtac catatgaata aggatcggct
 481 aactccgtgc cagcagccgc ggtaatacgg aggatccgag cgttatccgg atttattggg
 541 tttaaaggga gcgtaggcgg attgttaagt cagttgtgaa agtttgcggc tcaaccgtaa
 601 aattgcagtt gatactggca gtcttgagtg cagtagaggt gggcggaatt cgtggtgtag
 661 cggtgaaatg cttagatatc acgaagaact ccgattgcga aggcagctca ctggagtgta
 721 actgacgctg atgctcgaaa gtgtgggtat caaacaggat tagataccct ggtagtccac
 781 acagtaaacg atgaatactc gctgtttgcg atatacagta agcggccaag cgaaagcatt
 841 aagtattcca cctggggagt acgccggcaa cggtgaaact caaaggaatt gacgggggcc
 901 ngcacaagcg gaggaacatg tggtttaatt cgatgatacg cgaggaacct accccgggct
 961 taaattgcaa atgaattatg gggaaaccca tacgccgcaa ggcatntgtg aaggtgctgc
1021 atggttgtcg tcagctcgtg ccgtgaggtg tcggcttaag tgccataacg agcgcaaccc
1081 ttatcttcag ttactaacag gtcatgctga ggactctgga gagactgccg tcgtaagatg
1141 tgaggaaggt ggggatgacg tcaaatcagc acggccctta cgtccggggc tacacacgtg
1201 ttacaatggg gggtacagaa ggcagctacc tggtgacagg atgccaatcc caaaaacctc
1261 tctcagttcg gatcgaagtc tgcaacccga cttcgtgaag ctggattcgc tagtaatcgc
1321 gcatcagcca tggcgcggtg aatacgttcc cgggccttgt acacaccgcc cgtcaagcca
1381 tgaaagccgg gggtacctga agtacgtaac cgcaaggagn gt
```

*Bacteroides dorei* 16S rRNA gene (NCBI/Genbank accession code AB242142, SEQ ID NO: 5)

```
   1 agagtttgat cctggctcag gatgaacgct agctacaggc ttaacacatg caagtcgagg
  61 ggcagcatgt tcttagcttg ctaaggctga tggcgaccgg cgcacgggtg agtaacacgt
 121 atccaacctg ccgtctactc ttggccagcc ttctgaaagg aagattaatc caggatggga
 181 tcatgagttc acatgtccgc atgattaaag gtattttccg gtagacgatg gggatgcgtt
 241 ccattagata gtaggcgggg taacggccca cctagtcaac gatggatagg ggttctgaga
 301 ggaaggtccc ccacattgga actgagacac ggtccaaact cctacgggag gcagcagtga
 361 ggaatattgg tcaatgggcg atggcctgaa ccagccaagt agcgtgaagg atgactgccc
 421 tatgggttgt aaacttcttt tataaaggaa taaagtcggg tatgcatacc cgtttgcatg
 481 tactttatga ataaggatcg gctaactccg tgccagcagc cgcggtaata cggaggatcc
```

-continued

<div align="center">SEQUENCE LISTING</div>

```
 541 gagcgttatc cggatttatt gggtttaaag ggagcgtaga tggatgttta agtcagttgt
 601 gaaagtttgc ggctcaaccg taaaattgca gttgatactg gatgtcttga gtgcagttga
 661 ggcaggcgga attcgtggtg tagcggtgaa atgcttagat atcacgaaga actccgattg
 721 cgaaggcagc ctgctaagct gcaactgaca ttgaggctcg aaagtgtggg tatcaaacag
 781 gattagatac cctggtagtc cacacggtaa acgatgaata ctcgctgttt gcgatatacg
 841 gcaagcggcc aagcgaaagc gttaagtatt ccacctgggg agtacgccgg caacggtgaa
 901 actcaaagga attgacgggg gcccgcacaa gcggaggaac atgtggttta attcgatgat
 961 acgcgaggaa ccttacccgg gcttaaattg cactcgaatg atccggaaac ggttcagcta
1021 gcaatagcga gtgtgaaggt gctgcatggt tgtcgtcagc tcgtgccgtg aggtgtcggc
1081 ttaagtgcca taacgagcgc aacccttgtt gtcagttact aacaggtgat gctgaggact
1141 ctgacaagac tgccatcgta agatgtgagg aaggtgggga tgacgtcaaa tcagcacggc
1201 ccttacgtcc ggggctacac acgtgttaca atggggcg cagagggcg ctaccacgcg
1261 agtggatgcc aatccctaaa accctctca gttcggactg gagtctgcaa cccgactcca
1321 cgaagctgga ttcgctagta atcgcgcatc agccacggcg cggtgaatac gttcccgggc
1381 cttgtacaca ccgcccgtca agccatggga gccgggggta cctgaagtgc gtaaccgcga
1441 ggatcgccct agggtaaaac tggtgactgg ggctaagtct aaccaaggta acc
```

*Bacteroides eggerthii* 16S rRNA gene (NCBI/Genbank accession code
NR040864, SEQ ID NO: 6)

```
   1 aggttgatca tggctcagga tgaacgttag ctacaggact tacacatgca agtcgagggg
  61 cagcatgatt gaagcttgct tcaatcgatg gcgaccggcg cacgggtgag taacacgtat
 121 ccaacctgcc gataactcgg ggatagcctt tcgaaagaaa gattaatacc cgatagtata
 181 gttttttccgc atggtttcat tattaaagaa tttcggttat cgatgggggat gcgttccatt
 241 agatagttgg cggggtaacg gcccaccaag tcaacgatga atagggggttc tgagaggaag
 301 gtcccccaca ttggaactga gacacggtcc aaattcctac gggaggcagc agtgaggaat
 361 attggtcaat ggacgagagt ctgaaccagc caagtagcgt gaaggatgac tgccctatgg
 421 gttgtaaact tcttttatac gggaataaag tggagtatgc atactccttt gtatgtaccg
 481 tatgaataag gatcggctaa ctccgtgcca gcagccgcgg taatacggag gatccgagcg
 541 ttatccggat ttattgggtt taaagggagc gtaggcggtc gcttaagtca gttgtgaaag
 601 tttgcggctc aaccgtaaaa ttgcagttga tactgggcgc cttgagtgca gcataggtag
 661 gcggaattcg tggtgtagcg gtgaaatgct tagatatcac gaagaactcc gattgcgaag
 721 gcagcttact ggactgtaac tgacgctgat gctcgaaagt gtgggtatca aacaggatta
 781 gataccctgg tagtccacac agtaaacgat gaatactcgc tgttggcgat acacagtcag
 841 cggccaagcg aaagcattaa gtattccacc tggggagtac gccggcaacg gtgaaactca
 901 aaggaattga cgggggcccg cacaagcgga ggaacatgtg gtttaattcg atgatacgcg
 961 aggaacctta cccgggctta aattgcagcg gaatgtagtg gaaacattac agccttcggc
1021 cgctgtgaag tgctgcatgg ttgtcgtcag ctcgtgccgt gaggtgtcgg cttaagtgcc
1081 ataacgagcg caacccttat ctatagttac tatcaggtca tgctgaggac tctatggaga
1141 ctgccgtcgt aagatgtgag gaaggtgggg atgacgtcaa atcagcacgg cccttacgtc
1201 cggggctaca cacgtgttac aatggggggt acagaaggca gctacctggc gacaggatgc
1261 taatcccgaa aacctctctc agttcggatt ggagtctgca acccgactcc atgaagctgg
1321 attcgmtagt aatcgcgcat cagccacggc gcggtgaata cgttcccggg ccttgtacac
1381 accgcccgtc aagccatgaa agccgggggt acctgaagta cgtaa
```

*Bacteroidetes distasonis* 16S rRNA gene (NCBI/Genbank accession code
M86695, SEQ ID NO: 7).

```
   1 caatttaaac aacgaagagt ttgatcctgg ctcaggatna acgctagcga caggcttaac
  61 acatgcaagt cgaggggcac gcgcgrgtag caataccgng ngctggcnac cggcgcacgg
 121 gtgagtaacg cgtatgcaac ttgcctatca gagggggata acccggcgaa agtcggacta
 181 ataccgcatg aagcagggat cccgcatggg aatatttgct aaagattcat cgctnataga
 241 taggcatgcg ttccattagg cagttggcgg ggtaacggcc caccaaaccg acgatggata
 301 ggggttctga gaggaaggtc ccccacattg gtactgagac acggaccaaa ctcctacggg
 361 aggcagcagt gaggaatatt ggtcaatggc cgagaggctg aaccagccaa gtcgcgtgag
 421 ggatgaaggt tctatggatc gtaaacctct tttataaggg aataaagtgc gggacgtgtc
 481 cngtttgta tgtaccttat gaataaggat cggctaactc cgtgccagca gccgcggtaa
 541 tacggaggat ccgagcgtta tccggattta ttgggtttaa agggtgcgta ggcggccttt
 601 taagtcagcg gtgaaagtct gtggctcaac catagaattg ccgttgaaac tggggngctt
 661 gagtatgttt gaggcaggcg gaatgcgtgg tgtagcggtg aaatgcatag atatcacgca
 721 gaaccccgat tgcgaaggca gcctgccaag ccattactga cgctgatgca cgaaagcgtg
 781 gggatcaaac aggattagat accctggtag tccacgcagt aaacgatgat cactagctgt
 841 ttgcgataca ctgtaagcgg cacagcgaaa gcgttaagta tccacctggg gagtacgcc
 901 ggcaacggtg aaactcaaag gaattgacgg gngccngcac aagcggagga acatgtggtg
 961 taattcgatg atacgcgagg aaccttaccc gggtttgaac gcattcggac cgaggtggaa
1021 acaccttttc tagcaatagc cgtttgcgag gtgcgcatg gttgtcgtca gctcgtgccg
1081 tgaggtgtcg gcttaagtgc cataacgagc gcaacccttg ccactagtta ctaacaggtt
1141 aggctgagga ctctggtggn actgccagcg taagctgcga ggaaggcggg gatgacgtca
1201 aatcagcacg gcccttacat cggggggcgac aacggcggta caatggcgtg gacaaaggga
1261 ggccacctgg cgacagggag cgaatcccca aaccacgtct cagttcggat cggagtctgc
1321 aacccgactc cgtgaagctg gattcgctag taatcgcgca tcagccatgg cgcggtgaat
1381 acgttcccgg gccttgtaca caccgcccgt caagccatgg agccgggggg tacctgaagt
1441 ccgtaaccga aaggatcggc ctagggtaaa actggtgact ggggctaagn ngtaacaagn
1501 nnnnngtacc ggaagnnnnn nnnngaacac ctcctttct
```

*Bifidobacterium infantis* 16S rRNA gene (NCBI/Genbank accession code
D86184, SEQ ID NO: 8)

```
   1 tttgatcatg gctcaggatg aacgctggcg gcgtgcttaa cacatgcaag tcgaacggga
  61 tccatcgggc tttgcttggt ggtgagagtg gcgaacgggt gagtaatgcg tgaccgacct
```

-continued

SEQUENCE LISTING

```
 121 gccccataca ccggaatagc tcctggaaac gggtggtaat gccggatgtt ccagttgatc
 181 gcatggtctt ctgggaaagc tttcgcggta tgggatgggg tcgcgtccta tcagcttgac
 241 ggcggggtaa cggcccaccg tggcttcgac gggtagccgg cctgagaggg cgaccggcca
 301 cattgggact gagatacggc ccagactcct acgggaggca gcagtgggga atattgcaca
 361 atgggcgcaa gcctgatgca gcgacgccgc gtgagggatg gaggccttcg ggttgtaaac
 421 ctcttttatc ggggagcaag cgtgagtgag tttacccgtt gaataagcac ccgctaacta
 481 cgtgccagca gccgcggtaa tacgtagggt gcaagcgtta tccggaatta ttgggcgtaa
 541 agggctcgta ggcggttcgt cgcgtccggt gtgaaagtcc atcgcttaac ggtggatccg
 601 cgccgggtac gggcgggctt gagtgcggta ggggagactg gaattcccgg tgtaacggtg
 661 gaatgtgtag atatcgggaa gaacaccaat ggcgaaggca ggtctctggg ccgttactga
 721 cgctgaggag cgaaagcgtg gggagcgaac aggattagat accctggtag tccacgccgt
 781 aaacggtgga tgctggatgt ggggcccgtt ccacgggttc cgtgtcggag ctaacgcgtt
 841 aagcatcccg cctggggagt acggccgcaa ggctaaaact caaagaaatt gacggggggcc
 901 cgcacaagcg gcggagcatg cggattaatt cgatgcaacg cgaagaacct tacctgggct
 961 tgacatgttc ccgacgatcc cagagatggg gtttcccttc gggggcgggt cacaggtggt
1021 gcatggtcgt cgtcagctcg tgtcgtgaga tgttgggtta agtcccgcaa cgagcgcaac
1081 cctcgccccg tgttgccagc ggattgtgcc gggaactcac gggggaccgc cggggttaac
1141 tcggaggaag gtggggatga cgtcagatca tcatgcccct tacgtccagg gcttcacgca
1201 tgctacaatg gccggtacaa cgggatgcga cgcggcgacg cggagcggat ccctgaaaac
1261 cggtctcagt tcggatcgca gtctgcaact cgactgcgtg aaggcgagt cgctagtaat
1321 cgcgaatcag caacgtcgcg gtgaatgcgt tcccgggcct tgtacacacc gcccgtcaag
1381 tcatgaaagt gggcagcacc cgaagccggt ggcctaaccc cttgtgggat ggagccgtct
1441 aaggtgaggc tcgtgattgg gactaagtcg taacaaggta gccgtaccgg aaggtgcggc
1501 tggatcacct cctta
```

*Bifidobacterium longum* 16S rRNA gene (NCBI/Genbank accession code
M58739, SEQ ID NO: 9)
```
    1 ttttgtggag ggttcgattc tggctcagga tgaacgctgg cggcgtgctt aacacatgca
   61 agtcgaacgg gatccatcaa gcttgcttgg tggtgagagt ggcgaacggg tgagtaatgc
  121 gtgaccgacc tgccccatac accggaatag ctcctggaaa cgggtggtaa tgccggatgt
  181 tccagttgat cgcatggtct tctggngaaa gcntttcgcg gtatgggatg gggtcgcgtc
  241 ctatcagctt gacggngggg taacggcnna ccgtggcttc gacgggtagc cggcctgaga
  301 gggcgaccgg ccacattggg actgagatac ggcccngact cctacgggag gcagcagtgg
  361 ggaatattgc acaatgggcg caagcctgat gcagcgacgc cgcgtgaggg atggaggcct
  421 tcgggttgta aacctctttt atcggggagc aagcgagagt gagtttaccc gttgaataag
  481 caccggctaa ctacgtgcca gcagccgcgg taatacgtag ggtgcnagcg ttatccggaa
  541 ttattgggcg taaagggctc gtaggcggtt cgtcgcgctt ggtgtgaaag tccatcgctt
  601 aacggtggat ccgcgccggg tacggcgggg cttgagtgcg gtaggggaga ctggaattcc
  661 cggtgtaacg gtggaatgtg tagatatcgg gaagaacacc aatggcgaag gcaggtctct
  721 gggccgttac tgacgctgag gagcgaaagc gtggggagcg aacaggatta gatacccctgg
  781 tagtccacgc cgtaaacggt ggatgctgga tgtggggccn gttccacggg ttccgtgtcg
  841 gagctaacgc gttaagcatc ccgcctgggg agtacggccg caaggctaaa actcaaagaa
  901 attgacgggg gccngcacaa gcggcggagc atgcggatta attcgatgna acgcgaagaa
  961 ccttacctgg gcttgacatg ttcccgacgg tcgtagagat acggcntccc ttcggggcgg
 1021 gttcacaggt gcngcatggt cgtcgtcagc tcgtgtcgtg agatgttggg ttaagtcccg
 1081 caacgagcgc aaccctcgcc ccgtgttgcc agcggattat gccggnaact cacgggnnac
 1141 cgccggggtt aactcggagg aaggtgggga tgacgtcaga tcatcatgcc ccttacgtcc
 1201 agggcttcac gcatgctaca atggccggta caacgggatg cgacgcggcg acgcggagcg
 1261 gatccctgaa aacngtctc agttcggatc gcagtctgca actcgactgc gtgaaggcgg
 1321 agtcgctagt aatcgcgaat cagcaacgtc gcggtgaatg cgttcccngg ccttgtacac
 1381 accgcccgtc aagncatgaa agtgggcagc acccgaagcc ggtggcctaa ccccttgtgg
 1441 ganggagccg tctaaggtga ggctcgtgat tgggac
```

*Bifidobacterium breve* 16S rRNA gene (NCBI/Genbank accession code
AB006658, SEQ ID NO: 10)
```
    1 ttcgattctg gctcaggatg aacgctggcg gcgtgcttaa cacatgcaag tcgaacggga
   61 tccatcgggc tttgcttggt ggtgagagt gcgaacgggt gagtaatgcg tgaccgacct
  121 gccccatgca ccggaatagc tcctggaaac gggtggtaat gccggatgct ccatcacacc
  181 gcatggtgtg ttgggaaagc ctttgcggca tgggatgggg tcgcgtccta tcagcttgat
  241 ggcggggtaa cggcccacca tggcttcgac gggtagccgg cctgagaggg cgaccggcca
  301 cattgggact gagatacggc ccagactcct acgggaggca gcagtgggga atattgcaca
  361 atgggcgcaa gcctgatgca gcgacgccgc gtgagggatg gaggccttcg ggttgtaaac
  421 ctcttttgtt agggagcaag cactttgtg ttgagtgtac ctttcgaata agcaccggct
  481 aactacgtgc cagcagccgc ggtaatacgt agggtgcaag cgttatccgg aattattggg
  541 cgtaaagggc tcgtaggcgg ttcgtcgcgt ccggtgtgaa agtccatcgc ttaacggtgg
  601 atccgcgccg ggtacgggcg gcttgagtc cggtaggga gactggaatt cccggtgtaa
  661 cggtggaatg tgtagatatc gggaagaaca ccaatggcgaa ggcaggtctc ctggccgctt
  721 actgacgctg aggagcgaaa gcgtggggag cgaacaggat tagataccct ggtagtccac
  781 gccgtaaacg gtggatgctg atgtggggc cgttccacg gttccgtgt cggagctaac
  841 gcgttaagca tcccgcctgg ggagtacggc cgcaaggcta aaactcaaag aaattgacgg
  901 gggcccgcac aagcggcgga gcatgcggat taattcgatg caacgcgaag aaccttacct
  961 gggcttgaca tgttcccgac gatcccagag atggggtttc ccttcgggag gggttcacag
 1021 gtggtgcatg gtcgtcgtca gctcgtgtcg tgagatgttg ggttaagtcc cgcaacgagc
 1081 gcaaccctcg ccccgtgttg ccagcggatt gtgccgggaa ctcacggggg accgccgggg
 1141 ttaactcgga ggaaggtggg gatgacgtca gatcatcatg cccttacgt ccagggcttc
 1201 acgcatgcta caatggccgg tacaacggga tgcgacagtc cgagctggag cggatccctg
 1261 aaaaccggtc tcagttcgga tcgcagtctg caactcgact gcgtgaaggc ggagtcgcta
```

-continued

SEQUENCE LISTING

```
1321 gtaatcgcga atcagcaacg tcgcggtgaa tgcgttcccg ggccttgtac acaccgcccg
1381 tcaagtcatg aaagtgggca gcacccgaag ccggtggcct aacccccttgc gggagggagc
1441 cgtctaaggt gaggctcgtg attgggacta agtcgtaaca aggtagccgt accggaaggt
1501 gcggctggat cacctcctta
```

Bifidobacterium thermophilum 16S rRNA gene (NCBI/Genbank accession code
AB016246, SEQ ID NO: 11)

```
   1 agagtttgat catggctcag gatgaacgct ggcggcgtgc ttaacacatg caagtcgaac
  61 gggatcctgc gggctttgcc tgcgggtgag agtggcgaac gggtgagtaa tgcgtgacca
 121 acctgcccca tgctccggaa tagctcctgg aaacgggtgg taatgccgga tgttcccgcg
 181 ccccgcatgg ggtgcgggga aaagcttttg cggcgtggga tggggtcgcg tcctatcagc
 241 ttgttggcgg ggtgagggcc caccaaggct tcgacgggta gccggcctga gaaggcgacc
 301 ggccacattg ggactgagat acggcccaga ctcctacggg aggcagcagt ggggaatatt
 361 gcacaatggg cgcaagcctg atgcagcgac gccgcgtgcg ggatggaggc cttcgggttg
 421 taaaccgctt ttgtttggga gcaagccctt cggggtgagt gtaccttcg aataagcacc
 481 ggctaaatac gtgccagcag ccgcggtaat aagtagggtg cgagcgttat ccggatttat
 541 tgggcgtaaa gggcttgtag gcggtttgtc gcgtccggtg tgaaagtcca tcgcctaacg
 601 gtggatttgc gccgggtacg ggcgggctgg agtgcggtag gggagactgg aattcccggt
 661 gtaacggtgg aatgtgtaga tatcgggaag aacaccaatg gcgaaggcag gtctttgggc
 721 cgttactgac gctgaggagc gaaagcgtgg ggagcgaaca ggattagata ccctggtagt
 781 ccacgccgta aacggtggat gctggatgtg gggcccttcc acgggtcccg tgtcggggcc
 841 aacgcgttaa gcatcccgcc tggggagtac ggccgcaagg ctaaaactca aagaaattga
 901 cgggggcccg cacaagcggc ggagcatgcg gattaattcg atgcaacgcg aaaaacctta
 961 cctgggcttg acatgttccc gacgacggca gagatgtgt ttcccttcgg ggcgggttca
1021 caggtggtgc atggtcgtcg tcagctcgtg tcgtgagatg ttgggttcaag tcccgcaacg
1081 agcgcaaccc tcgcccgtg ttgccagcgc gtcttggcgg gaactcaccg gggaccgccg
1141 gggtttaccc ggaggaaggt ggggatgacg tcagatcatc atgcccctta cgtccagggc
1201 ttcacggcat gctacaatgg ccgggtacag gcggggatgc agacatggtg acatggagcg
1261 ggatccctga aaaccggtct cagttcggga tcggagcgtg caacccggct cggtgaaggc
1321 ggagtcggct aagtaatcgc ggatcagcaa cgccgcggtg aatgcgttcc cgggccttgt
1381 acacaccgcc cgtcaagtca tgaaagtggg cagcacccga agccggtggc ctgaccagta
1441 ttgctggggg gagccgtcta aggtgaggct cgcgattggg agtaagtcgt aacaaggtag
1501 ccgtaccgga aggtgcggct ggatcacctc ctt
```

Bifdobacterium bifidum 16S rRNA gene (NCBI/Genbank accession code
M38018, SEQ ID NO: 12)

```
   1 tttttgtgga gggttcgatt ctggctcagg atgaacgctg gcggcgtgct taacacatgc
  61 aagtcgaacg ggatccatca agcttgcttg tggtgagag tggcgaacgg gtgagtaatg
 121 cgtgaccgac ctgccccatg ctccggaata gctcctggaa acgggtggta atgccgnatg
 181 ttccacatga tcgcatgtga ttgtgggaaa gattctatcg gcgtgggatg gggtcgngtc
 241 ctatcagctt gttggtgagg taacggctca ccaaggcntc gacgggtag cggcctgaga
 301 gggcgaccgg ccacattggg actgagatac ggcccagact cctacgggag gcagcagtgg
 361 ggaatattgc acaatgggcg caagcctgat gcagcgacgc cgcgtgaggg atggaggcct
 421 tcgggttgta aacctctttt gtttgggagc aagccttcgg gtgagtgtac ctttcgaata
 481 agcgccggct aactacgtgc cagcagccgg gtaatacgt agggnnnnag cgttatccgg
 541 atttattggg cgtaaagggc tcgtaggcgg ctcgtcgcgt ccggtgtgaa agtccatcgc
 601 ttaacggtgg atctgcgccg ggtacgggcg gctggagtg cggtagggga gactggaatt
 661 cccggtgtaa cggtggaatg tgtagatatc gggaagaaca ccgatggcga aggcaggtct
 721 ctgggcngtc actgacgctg aggagcnaaa gcgtggggag cgaacaggat tagtaccct
 781 ggtagtccac gccgtaaacg gtggacgctg atgtggggc acgttccacg tgttccgtgt
 841 cggagctaac gcgttaagcg tcccgcctgg ggagtacggc cgcaaggcta aaactcaaag
 901 aaattgacgg gggccngcac aagcggcgga gcatgcggat taattcgaac naacgcgaag
 961 aaccttacct gggcttgaca tgttcccgac gacgccagag atggcgtttc ccttcgggga
1021 gggttcacag gtggtgcatg gtcgtcgtca gctcgtgtcg tgagatgttg ggttaagtcc
1081 cgcaacgagc gcaaccctcg ccccgtgttg ccagcacgtt atggtgggaa ctcacgggnn
1141 accgccgggg ttaacncgga ggaaggtggg gatgacgtca gatcatcatg cccccttacgt
1201 ccagggcttc acgcatgcta caatggccgg tacagcggga tgcgacatgg cgacatgag
1261 cggatccctg aaaacggtc tcagttcgga tcggagcctg caacccggct ccgtgaaggc
1321 ggagtcgcta gtaatcgcgg atcagcaacg ccgcggtgaa tgcgttcccg ggccttgtac
1381 acaccgcccg tcaagtcatg aaagtgggca gcacccgaag ccggtggcct aaccccttgt
1441 gggatggagc cgtctaaggt gaggctcgtg nttgggacta agnngtaaca agnnnnnngt
1501 accgaagnn nnnnnnngat cacctccttt ct
```

Bifidobacterium adolescentis 16S rRNA gene (NCBI/Genbank accession code
M58729, SEQ ID NO: 13)

```
   1 nnnnttgtgg agggttcgat tctggctcag gatnaacgct ngcggcgtgc ttaacacatg
  61 caagtcgaac gggatcggct ngagcttgct ccggctgtga gagtggcgaa cgggtgagta
 121 atgcgtgacc gacctgcccc atacaccgga atagctcctg gaaacgggtg gtaatgccgg
 181 atgctccagt tggatgcatg tccttctggg aaagattcta tcggtatggg atggggtcgc
 241 gtcctatcag cttgatggcg gggtaacggc ccnccatggc ttcgacgggn agccggcctg
 301 agagggcgac cggccacatt gggactgaga tacggcccng actcctacgg gaggcagcag
 361 tgggnaatat tgcacaatgg gcgcaagcct aatgcagcga gggatgacgg
 421 ccttcgggtt gtaaaccgct tttgactggg agcaagcctt cggggtgagt gtacctttcg
 481 aataagcacc ggctaactac gtgccagcag ccncggtaat acgtagggtg cnagcgttat
 541 ccggaattat tgggcgtaaa gggctcgtag gcggttcgtc gcgtccggtg tgaaagtcca
 601 tcgcttaacg gtggntccgc gccgggtacg gcggncttg agtgcggtag ggnagactgg
 661 aattccnggt gtaacggtgg aatgtgtaga tatcgggaag aacaccaatg gcgaaggcag
```

-continued

---

SEQUENCE LISTING

---

```
 721 gtctctgggc ngtnactgac gctgaggagc gaaagcgtgg ggagcgaaca ggattagata
 781 ccctggtagt ccacgccgta aacggtggat gctggatgtg gggaccattc cacggtctcc
 841 gtgtcggagc caacgcgtta agcatcccgc ctggggagta cggccgcaag gctaaaactc
 901 aaagaaattg acgggnnccn ncacaagcgg cngagcatgc ggattaattc gatnnaacgc
 961 gaagaacctt acctgggctt gacatgttcc cgacaggccc cagagatggg nnntccttcg
1021 ggncgggntc acaggtggng catggtcgtc gtcagctcgt gtcgtgagat gttgggttaa
1081 gtcccgcaac gagcgcaacc ctcgcccctgt gttgccagca cgtcgtggtg gnaactcacg
1141 ggngaccgcc ggggtcaact cggaggaagg tgggnatgac gtcagatcat catgcccctt
1201 acgtccaggg cttcacgcat gctacaatgg ccggtacaac gggatgcgac ctcgtgaggg
1261 ggagcggatc ccttaaaacc ggnctcagtt cggattggag tctgcaaccc gactccatga
1321 aggcggagtc gctagtaatc gcggatcagc aacgccgcg tnaatgcgtt cccgggcctt
1381 gtacacaccg cccgtcaagc catgaaagtg ggtagcaccc gaagccggtg gcccnacctt
1441 tttggggggga gccgtctaag gtgagnctcg tgatngg
```

*Bifodbacterium catenulatum* 16S rRNA gene (NCBI/Genbank accession code
M58732, SEQ ID NO: 14)

```
   1 nnnttttgtg agnggttcga ttctggctca ggatgaacgc tggcggcgtg cttaacacat
  61 gcaagtcgaa cgggatcagg cagcttgctg cctggngaga gtggcgaacg ggnnagtaat
 121 gcgtgaccna cctgccnnat acaccggaat agctcctgga aacgggtggt aatgccggat
 181 gctccgactc ctcgcatggg gtgtcggnaa agatttcatc ggtatgggat ggggtcgngt
 241 cctatcaggt agtcggcggg gtaacggcnn nccgagcctn cgacgggtag ccggcctgag
 301 agggcgaccg gccacattgg gactgagata cggccnngac tcctacggga ggcagcagtg
 361 ggncatattg cacaatgggc gcaagcctna tgcagcgacg cnnngtgcgg gntgacggcc
 421 tncgggttgt aaaccncntt tgatcgggag caagccttcg ggtgagtgta ccnttcgaat
 481 aagcaccggc taactacgtg ccagcagccg cggtaatacg tagggtgcna gcgttatccg
 541 gaattattgg gcgtaaaggg ctcgtaggcg gttcgtcgcg tccggtgtga aagtccatcg
 601 cttaacggtg gatctgcgcc gggtacgggc gggctggagt gcggtagggg ngactggaat
 661 tccgggtgta acggtggaat gtgtagatat cgggaagaac accaatggcg aaggcnggtc
 721 tctgggcngn nactgacgct gaggagcgaa agcgtgggga gcgaacagga ttagataccc
 781 tggtagtcca cgccgtaaac ggtggatgct ggatgtgggg cnngttccac gggttccgtg
 841 tcggagctaa cgcgttaagc atccngcctg gggngtncgg cngcaaggcn nnnncncaaa
 901 gaaattgang ggggccngca caagcggngg agcatgcgga ttnattcgan nnaacgcgaa
 961 gaaccttacc tgggcttgac atgttcccga cagccgtaga gatacggnct cccttcgggg
1021 cgggnncaca ggtggngcat ggtcgtcgtc ngctcgtgtc gtgagatgtt gggttaagtc
1081 ccncaacgag cgcaaccctc gccctgtgtt gccgacacgt catgtnggna ctcacgggnn
1141 accgccgggg tcaactcgga ggaaggtggg gatgacgtca gatcatcatg ccccttacgt
1201 ccagggcttc acgcatgcta caatggccgg tacaacggga tgcgacatgg cgacatggag
1261 cggatccctg aaaaccggnc tcagttcgga ttggagtctg caacccgact ccatgaaggc
1321 ggagtcgcta gtaatcgcgg atcagcaacg ccgcggtgaa tgcgttcccg ggccttgtac
1381 acaccgcncg tcaagncatg aaagtgggta gcacccgaag ccggtggcct nacccnttgt
1441 gggatggagc cgtctaaggt gagactcgtg attgggac
```

*Bifdobacterium pseudocatenulatum* 16S rRNA gene (NCBI/Genbank accession
code D86187, SEQ ID NO: 15)

```
   1 gtttcgattc tggctcagga tgaacgctgg cggcgtgctt aacacatgca agtcgaacgg
  61 gatccatcag gctttgcttg gtggtgagag tggcgaacgg gtgagtaatg cgtgaccgac
 121 ctgcccata caccggaata gctcctggaa acgggtggta atgccggatg ctccgactcc
 181 tcgcatgggg tgtcggaaa gatttcatcg gtatgggatg gggtcgcgtc ctatcaggta
 241 gtcggcgggg taacgcccca ccgagcctac gacgggtagc cggcctgaga gggcgaccgg
 301 ccacattggg actgagatac ggcccagact cctacgggag gcagcagtgg gaatattgc
 361 acaatgggcg caagcctgat gcagcgacgc cgcgtgcggg atgacggcct cgggttgta
 421 aaccgctttt gatcgggagc aagccttcgg gtgagtgtac ctttcgaata agcaccggct
 481 aactacgtgc cagcagccgc ggtaatacgt agggtgcaag cgttatccgg aattattggg
 541 cgtaaagggc tcgtaggcgg ttcgtcgcgt ccggtgtgaa agtccatcgc ttaacggtgg
 601 atctgcgccg ggtacgggcg ggctggagt cggtaggggga gactggaatt cccggtgtaa
 661 cggtggaatg tgtagatatc gggaagaaca ccaatggcga aggcaggtct ctgggccgtt
 721 actgacgctg aggagcgaaa gcgtggggag cgaacaggat tagataccct ggtagtccac
 781 gccgtaaac gtggatgctg atgtgggc cgttccacg gttccgtgt cggagctaac
 841 gcgttaagca tccgcctgg ggagtacggc cgcaaggcta aaactcaaag aaattgacgg
 901 gggcccgcac aagcggcgga gcatgcggat taattcgatg caacgcgaag aaccttacct
 961 gggcttgaca tcttcccgac agccgtagag atatggcctc ccttcggggc gggttcacag
1021 gtggtgcatg gtcgtcgtca gctcgtgtcg tgagatgttg ggttaagtcc gcaacgagc
1081 gcaaccctcg ccctgtgttg ccagcacgtc atggtgggaa ctcacggggg accgccgggg
1141 tcaactcgga ggaaggtggg gatgacgtca gatcatcatg cccttacgt ccagggcttc
1201 acgcatgcta caatggccgg tacaacggga tgcgacacgg cgacgtggag cggatccctg
1261 aaaaccggtc tcagttcgga ttggagtctg caacccgact ccatgaaggc ggagtcgcta
1321 gtaatcgcgg atcagcaacg ccgcggtgaa tgcgttcccg ggccttgtac acaccgcccg
1381 tcaagtcatg aaagtgggta gcacccgaag ccggtggcct aacccttgt ggatggagcc
1441 gtctaaggt agactcgtga ttgggactaa gtcgtaacaa ggtagccgta ccggaaggtg
1501 cggctggatc acctcctta
```

*Akkermansia muciniphila* 16S rRNA gene (NCBI/Genbank accession code
AY271254, SEQ ID NO: 16)

```
   1 aacgaacgct ggcggcgtgg ataagacatg caagtcgaac gagagaattg ctagcttgct
  61 aataattctc tagtggcgca cgggtgagta acacgtgagt aacctgcccc cgagagcggg
 121 atagccctgg gaaactggga ttaataccgc atagtatcga aagattaaag cagcaatgcg
 181 cttggggatg ggctcgcggc ctattagtta gttggtgagg taacggctca ccaaggcgat
```

-continued

SEQUENCE LISTING

```
 241 gacgggtagc cggtctgaga ggatgtccgg ccacactgga actgagacac ggtccagaca
 301 cctacgggtg gcagcagtcg agaatcattc acaatggggg aaaccctgat ggtgcgacgc
 361 cgcgtggggg aatgaaggtc ttcggattgt aaacccctgt catgtgggag caaattaaaa
 421 agatagtacc acaagaggaa gagacggcta actctgtgcc agcagccgcg gtaatacaga
 481 ggtctcaagc gttgttcgga atcactgggc gtaaagcgtg cgtaggctgt ttcgtaagtc
 541 gtgtgtgaaa ggcgcgggct caacccgcgg acggcacatg atactgcgag actagagtaa
 601 tggaggggga accggaattc tcggtgtagc agtgaaatgc gtagatatcg agaggaacac
 661 tcgtggcgaa ggcgggttcc tggacattaa ctgacgctga ggcacgaagg ccagggagc
 721 gaaagggatt agataccct gtagtcctgg cagtaaacgg tgcacgcttg gtgtgcgggg
 781 aatcgacccc ctgcgtgccg gagtaacgcg ttaagcgtgc cgcctgggga gtacggtcgc
 841 aagattaaaa ctcaaagaaa ttgacgggga cccgcacaag cggtggagta tgtggcttaa
 901 ttcgatgcaa cgcgaagaac cttacctggg cttgacatgt aatgaacaac atgtgaaagc
 961 atgcgactct tcggaggcgt tacacaggtg ctgcatggcc gtcgtcagct cgtgtcgtga
1021 gatgtttggt taagtccagc aacgagcgca accctgttg ccagttacca gcacgtgaag
1081 gtggggactc tggcgagact gcccagatca actgggagga aggtggggac gacgtcaggt
1141 cagtatggcc cttatgccca gggctgcaca cgtactacaa tgcccagtac agagggggtc
1201 gaagccgcga ggcggaggaa atcctaaaaa ctgggcccag ttcggactgt aggctgcaac
1261 ccgcctacac gaagccggaa tcgctagtaa tggcgcatca gctacggcgc cgtgaatacg
1321 ttcccgggtc ttgtacacac cgcccgtcac atcatggaag ctggtcgcac ccgaagtatc
1381 tgaagccaac cgcaaggagg cagggtccta aggtgagact ggtaactggg atg
```

*Akkermansia glycanipila* 16S rRNA gene (NCBI/Genbank accession code NR152695, SEQ ID NO: 17)

```
   1 aacgaacgct ggcggcgtgg ataagacatg caagtcgaac ggagaagcaa tagcttgcta
  61 atgcttctta gtggcgcacg ggtgagtaac acgtgagcaa cctgccttcg agacgggaat
 121 agccctggga aaccgggatt aatgcccgat agactcgcaa gagtaaacgc agcaatgcgc
 181 ttgaagaggg gctcgcggcc tattagttag ttggtgaggt aacggctcac caaggcgatg
 241 acgggtagcc ggtctgagag gatgtccggc cacactggaa ctgagacacg gtccagacac
 301 ctacggtgg cagcagtcga gaatcattca caatggggga aaccctgatg gtgcgacgcc
 361 gcgtggggga agaaggtctt cggattgtaa accctgtca tgtgggagca aggcgcaagc
 421 ttgatagtac cacaagagga agagacggct aactctgtgc cagcagccgc ggtaatacag
 481 aggtctcaag cgttgttcgg aatcactggg cgtaaagggt acgtaggctg catcataagt
 541 cgggcgtgaa aggcaggggc tcaacccctg gagtgcgctt gatactgtga tgctagagtc
 601 atggaggggg aaccggaact ctcggtgtag cagtgaaatg cgtagatatc gagaagaaca
 661 ctcgtggcga aggcgggttc ctggacatgt actgacgctg aggtacgaag gctaggggag
 721 cgaaagggat tagatacccc tgtagtccta gcagtaaacg gtgcacgctt ggtgtgtggg
 781 gaatcgaccc cccacgtgcc ggagcaaacg cgttaagcgc gccgcctggg gagtacggtc
 841 gcaagattaa aactcaaaga aattgacggg gacccgcaca agcggtggag tatgtggctt
 901 aattcgatgc aacgcgaaga accttacctg ggcttgacat gtgatgaaca acatgtgaaa
 961 gcatgtgaca cctcggtggc gtcacacagg tgctgcatgg ccgtcgtcag ctcgtgtcgt
1021 gagatgtttg gttaagtcca gcaacgagcg caaccctgt tgccagttac cagcacgtta
1081 tggtggggac tctggcgaga ctgcccagat caactgggag gaaggtgggg acgacgtcag
1141 gtcagtatgg cccttatgcc cagggctgca cacgtactac aatgcccagt acagagggta
1201 ccgaacccgc gagggggagg caatccatga aaactgggcc cagttcggat tgtaggctgc
1261 aactcgccta catgaagaty gaatcgctag taatggcgca tcagctacgg cgccgtgaat
1321 acgttccccgg gtcttgtaca caccgcccgt cacatcatgg aagccggtcg cacccgaagt
1381 atctgaagcc aaccgcaagg aggcagggtc ctaaggtgag actggtaact gggatgaa
```

As used herein, the term "identity" refers to a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J.

Bishop, ed., Academic Press, San Diego, 1994, and Carillo, H., and Lipton, D., SIAM J. Applied Math (1988) 48:1073. Methods to determine identity and similarity are codified in computer programs. For example, NCBI Nucleotide Blast with standard settings (blastn, blast.ncbi.nlm.nih.gov/). Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215: 403).

As an illustration, by a nucleotide sequence having at least, for example, 95% "identity" to a reference nucleotide sequence, it is intended that the nucleotide sequence is identical to the reference sequence except that there may be up to five point mutations per each 100 nucleotides of the reference polypeptide sequence. In other words, to obtain a nucleotide sequence being at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence.

EXPERIMENTAL SECTION

Example 1

Infants born by vaginal delivery are colonized with maternal fecal microbes. Cesarean section (CS) birth disturbs the mother-to-neonate transmission. Here, it was evaluated whether the disturbed intestinal microbiota development could be restored in term CS-born infants by postnatal, orally-delivered fecal microbiota transplantation (FMT). Seventeen mothers were recruited, from which seven were selected after careful screening. Their infants received a diluted fecal sample of their own mothers taken 3 weeks prior to delivery. All seven infants had an uneventful clinical course during the three-month follow-up and showed no adverse effects. Time-series of the fecal microbiota composition of the FMT-treated CS-born infants no longer resembled that of untreated CS-born infants but showed significant similarity with that of the vaginally-born infants. This proof-of-concept demonstrates that the intestinal microbiota of CS-born infants can be postnatally restored by maternal FMT.

Results

Maternal Fecal Microbiota Transplantation in Caesarean Section-Born Infants

A total of 17 pregnant mothers due to deliver by CS were enrolled for the postnatal FMT of their to-be-born infants. A total of 7 mothers were selected following an extensive screening with modifications relevant for newborns, including group B streptococci (GBS) carrier status analysis. All mothers delivered at the gestational age of 37 weeks (±3 days) and breastfed exclusively at least for two months. The mother of infant M11 received oral cephalexin for mastitis for 7 days starting 32 days after delivery, the other mother-infant pairs did not receive antibiotics apart from the single intravenous dose of 1.5 g cefuroxime, given 30 to 60 minutes before incision to all women undergoing elective CS. After birth by CS, the 7 selected newborns, 5 girls and 2 boys, were subject to FMT with the stool transplant of their own mother that was delivered in 5 mL of the first human milk feeding. The infants were followed at the maternity ward for 2 days and their inflammatory markers were assessed. The mean birth weight of the FMT-treated infants was 3240±285 grams and height 49.9±1.7 cm. All infants were healthy with a mean APGAR score of 9±1. All infants received 3.5 mg of the transplant except for one infant (M6), who was given 7 mg of the transplant. Anaerobic plating indicated that a single dose contained approximately 0.7-16 $10^6$ live bacterial cells.

While all other neonates had a C-Reactive Protein (CRP) of 10 mg/L or less at 48 hours after birth, the infant M6 presented the value of 67 mg/L. This infant did not have clinical symptoms related to infection and during follow-up, the CRP decreased to 39 mg/L the next day and the infant was discharged without the commencement of antimicrobial treatment. Although clinically inconsequential, due to this increase in CRP, all subsequent infants received 3.5 mg of transplant and no increased CRP was observed. The clinical course of the infants was uneventful. No increase in temperature was observed during follow-up at the maternity ward. At the four-week follow-up visit, the parents of three neonates (infants M4, M8 and M12) reported mild gastrointestinal symptoms. The four other parents reported no gastrointestinal symptoms. Overall, the parents did not report any other symptoms, illness, or need for doctor's appointments that could be related to the treatment, indicating that the FMT did not cause any adverse health effects by the age of 3 months. The weight of the treated infants at 3 months (5702±525 g) was in the range of normal development.

Maternal Fecal Microbiota Shows Selective Outgrowth Upon Transplantation in Caesarean Section-Born Infants Since the health and development of the FMT-treated infants was normal, the research was next focused on their fecal microbiota that was analyzed by 16S rRNA gene amplicon sequencing and comparison with that of their mothers. The mothers' fresh fecal sample generated 3 weeks prior to delivery (samples coded "Mother A") was used to prepare the transplant (samples coded "Transplant") and hence compared these with the mothers' samples donated a few days prior to delivery (samples coded "Mother B") for the microbiota compositions. As expected for adults, the microbiota in these mothers' samples were highly similar, but clearly distinct from that of the infants' samples in an unsupervised principal component (PCoA) visualization. The microbiota in the meconium samples were equally different from any of the fecal samples. The infant samples collected after day 2 were rather similar in composition. The microbiota in the FMT-treated infants' samples was found to be very different from the microbiota of their mothers that donated the transplant, indicating highly selective outgrowth upon transplantation. The mothers' microbiota had the characteristic adult composition that was dominated by Ruminococcaceae and Lachnospiraceae. The meconium samples were mostly dominated by Aeromonas spp., except for infants M12 and M17, who had a more diverse composition resembling fecal samples. Six of the seven infants showed a uniform microbiota development with Bacteroides and Bizdobacterium spp. rapidly rising to dominance, while infant M17 had high abundances of Enterobacter Escherichia, Streptococcus and Veillonella. Remarkably, these were already present in the meconium of M17. In the 2-day fecal samples the microbiota consisted nearly exclusively of Bacteroides spp. (M10 and M11), or approximately half Bacteroides spp. together with uncultured Acidaminococcaceae (M4), Butyricimonas and Enterococcus spp. (M6—this infant had an elevated CRP at that day), or Paludibacter (M8), or Enterobacter Escherichia (M12). Infant M17 retained a diverse composition at day 2. The abundance of Bacteroides spp. declined with age in all infants, except for M17, in which Bacteroides outgrowth was observed at 4 weeks. By the age of 7 days, Bifidobacteria had emerged as the dominant group in all but two infants (M17 and M11) that were dominated by Enterobacteriaceae. Bifidobacteria remained abundant in all subsequent samples, with the exception of the 4-week samples of infants M6 and M17, were Enterobacteriaceae and Bacteroides were abundant.

Microbiota Development in Transplanted Caesarean Section-Born Infants Resembles that of Vaginally Delivered Infants To compare the samples from the FMT-treated infants with representative data from untreated Finnish infants, 82 additional samples were collected from vaginally-born and CS-born fully breastfed infants, which were sampled, processed and analyzed for their microbiota composition following the same methodology. Most of the FMT-treated CS-born infants received probiotics. These mainly include Lactobacillus reuteri that is present in the commonly used brand of vitamin D supplement, which, in the Finnish national program, is given to infants from two weeks onward. No effects of this intervention were observed in the microbiota of the FMT-CS infants or in the samples of the Finnish control infants that also received this probiotic (32 of the 3 weeks or later samples). The overall microbiota development in the FMT-treated CS-born infants resembled much more that of the vaginally delivered infants than that of the non-treated CS-born infants. During the first few days of life the microbiota of the FMT-treated infants differed from the vaginally delivered infants (p=0.03, PER-MANOVA), but from 7 days onwards the FMT-treated infants were similar to the vaginally delivered infants and distinct from the non-treated CS-delivered ones. To further detail the microbiota development in the transplanted infants, tests were performed to ascertain the microbiota differences between the vaginally born infants and the CS-born treated and untreated infants. The tests were adjusted for probiotic use (all control infants were fully breastfed and did not receive antibiotics) and did a sensitivity analysis by omitting the urgent CS-cases.

Figure 1B:
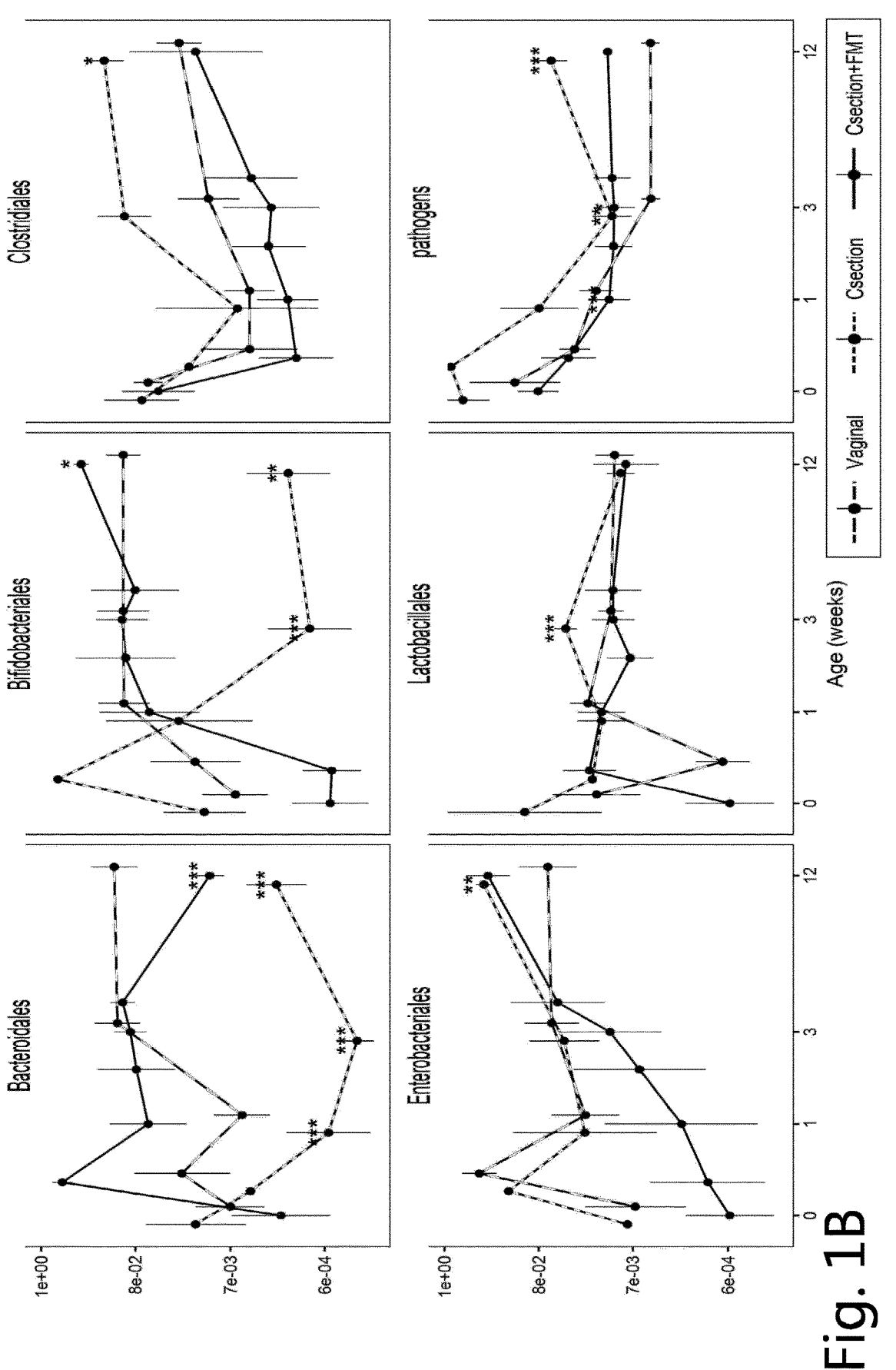
Figure 1C:
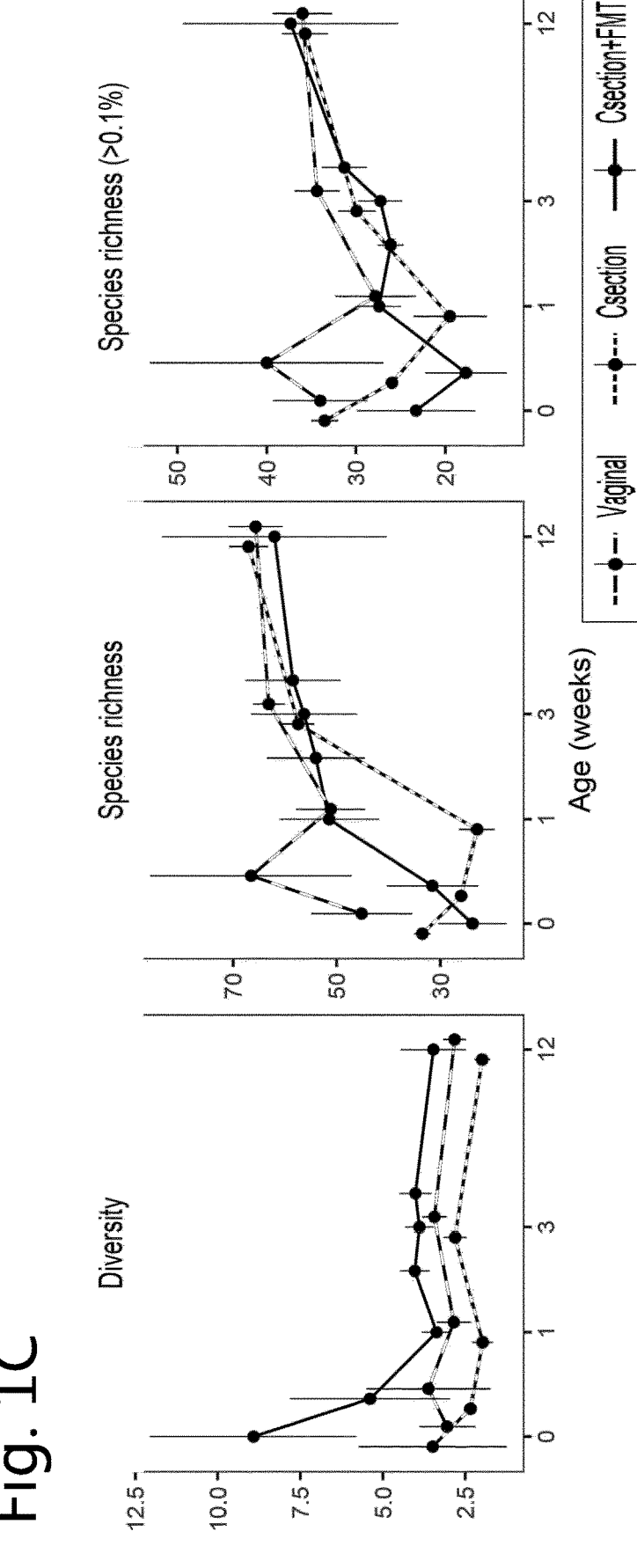
Figure 2A:
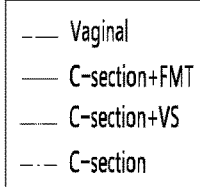
FIGS. 2A-2F: Comparison of the newly generated samples with publicly available data sets on infant microbiota. Microbiota composition is compared between the CS+FMT infants, untreated CS, vaginally delivered infants, and CS-born infants treated with vaginal swabs (VS). Principal coordinates analysis is based on Bray-Curtis dissimilarities of the class-level microbiota in the infants at different time points: 2 days (FIG. 2A), 7 days (FIG. 2B), 2 weeks (FIG. 2C), 3 weeks (FIG. 2D), 1 month (FIG. 2E), 3 months (FIG. 2F). The CS+FMT samples derive from this study, the VS sampled from an earlier study (Dominguez Bello et al., 2016) and all CS and controls from this and earlier published studies (Abrahamsson et al., 2012; Fouhy et al., 2012; Jakobsson et al., 2014; Yap et al., 2014; Kostic et al., 2015; Zijlmans et al., 2015; Hill et al., 2017; Korpela et al., 2017 and 2018a; Nagpal et al., 2017; Sakwinska et al., 2017; Tun et al., 2017; Backhed et al., 2015; Chu et al., 2017; Asnicar et al., 2015).
Figure 2B:
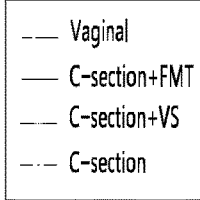
Figure 2C:
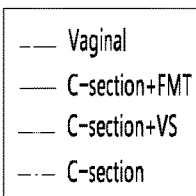
Figure 2C:
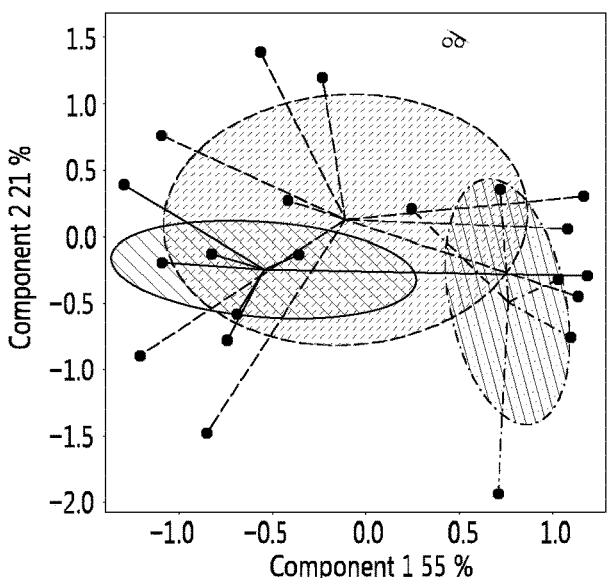
Figure 2D:
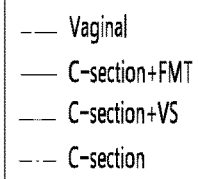
Figure 2E:
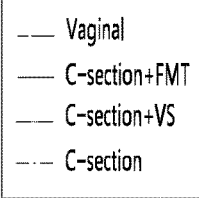
Figure 2F:
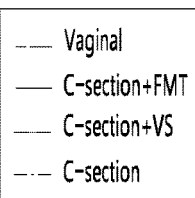
Figure 2F:
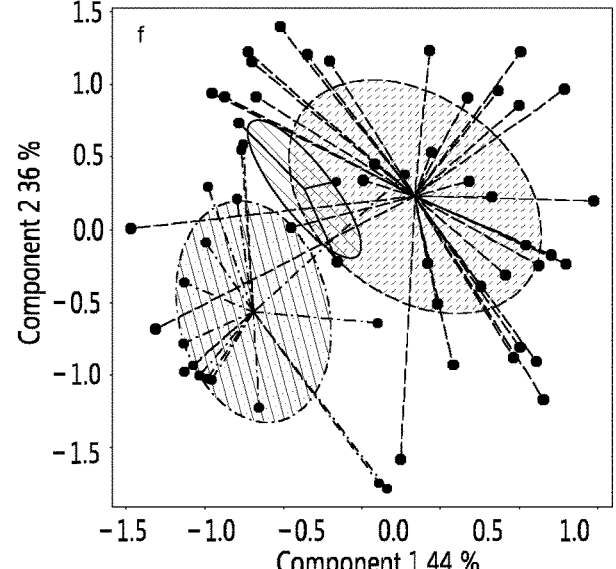

When comparing the abundances of the major microbiota families (FIG. 1A) and orders (FIG. 1), it was observed that compared with the vaginally delivered infants, the CS-born infants had consistently and significantly low abundances of *Bacteroidales* (mainly genus *Bacteroides*) and *Bifidobacteriales*, and an increased abundance of Lactobacillales, Clostridiales and *Enterobacteria*. This was not the case in the FMT-treated CS-born infants (excluding a potential effect of the used probiotic Lactobacilli) and the most remarkable effect of the FMT treatment was the rapid normalization of the *Bacteroidales* abundance. Indeed, the abundance of *Bacteroidales* was significantly lower in the CS group compared with both the FMT group and the vaginally born group at 1 and 3 weeks (p 0.001). At 12 weeks, the abundance of *Bacteroidales* declined in the FMT group. The FMT-treated infants had a non-significantly reduced abundance of Bifidobacteria during the first two days of life, after which, the levels of Bifidobacteria were comparable to those in the vaginally born infants. *Clostridiacaea* were significantly elevated in the infants of CS group compared with those in the vaginal and FMT treated groups, especially at 3 and 12 weeks (p<0.01). In addition to the differences in the dominant taxa, there were further, mostly transient, differences between the groups in the lower-abundance taxa. The FMT treatment changed the microbiota of the CS-born infants in such a way that the temporal development of all relevant groups resembled that of the vaginally delivered infants. Importantly, the combined relative abundance of the potential pathogens *Enterococcus faecium, Enterococcus faecalis, Enterobacter cloacae, Klebsiella pneumoniae, Klebsiella oxytoca, Haemophilus influenza, Campylobacter jejuni* and *Salmonella enterica* were consistently elevated in the CS group, but not in the FMT-CS group (FIG. 1i). The difference in the pathogen abundance between the CS and the FMT-CS groups was significant at 1 week (p<0.0001) and 12 weeks (p<0.00001). Microbial diversity, as measured by the inverse Simpson diversity index, counts of operational taxonomic units (OTU) and species count, tended to be lower in the CS group compared with both the vaginal and the FMT-treated groups (FIG. 1C). The FMT treatment increased diversity, particularly the OTU count by the age of 1 week. This was due to an increase in very low abundance OTUs, many of which mapped to the same taxonomic species, since the number of abundant species was similar between the groups.

Maternal FMT, But Not Vaginal Swabbing, Restored Microbiota in CS-Born Infants

To generalize the observations that the FMT-treatment restored the microbiota of CS-born infants, the data was expanded with publicly available microbiota data sets obtained from cohorts in Sweden (Backhed et al., 2015), Germany (Korpela et al., 2018a), Italy (Ansicar et al., 2015)

and the US (Chu et al., 2017). These included in total 163 vaginally and 38 CS-born infants as well as 6 CS-born infants that were experimentally inoculated with maternal vaginal microbes (Dominguez Bello et al., 2016). Moreover, the average microbiota data was added that were available from an additional 12 studies from Sweden (Abrahamsson et al., 2012; Jakobsson et al., 2014), Singapore (Yap et al., 2014, Sakwinska et al., 2017)), Finland (Kostic et al., 2015; Korpela et al., 2017), Netherlands (Zijlmans et al., 2015; Korpela et al., 2017), Ireland (Fouhy et al., 2012; Hill et al., 2017), Japan (Nagpal et al., 2017), and Canada (Tun et al., 2017). The microbiota was characterized at class level (Proteobacteria summarized to phylum level for simplicity), as this appeared sufficiently robust against biases caused by technical variation, as reported previously (Korpela and de Vos, 2018). A PCoA plot of this mixed data set revealed that the microbiota composition clustered clearly by birth mode (FIGS. 2A-2F). Confirming and expanding the earlier observations, the microbiota from the FMT-treated CS-born infants clustered with those from vaginally born infants from 2 days till 3 months.

Notably, the samples from the infants treated by vaginal swabs as described previously (Dominguez Bello et al., 2016) clustered either with the untreated CS-born infants (2 days, 7 days, 4 weeks) or did not resemble any of the other samples (2-3 weeks). This result was very generic and not driven by the country where the samples were collected, probiotic use, breast or formula feeding, or the type of C-section (urgent or elective).

Conclusion

None of the 7 treated infants showed complications and the FMT restored the microbiota development to resemble that of the infants born by vaginal delivery. Importantly, the maternal FMT corrected the persistent lack of *Bacteroides* spp. in CS-born infants and the delayed Bifidobacteria development, a signature of CS-born infants (Backhed et al., 2017, Korpela and de Vos, 2018, Shao et al., 2019). A recent large-scale study of the microbiota of newborns confirmed the disrupted transmission of *Bacteroides* strains in CS-born infants (Shao et al., 2019) Of interest, it was also observed that compared with vaginally-delivered infants, the CS-born infants showed increased levels of potential opportunistic pathogens, such as *Enterococcus, Enterobacter* and *Klebsiella* spp. (Shao et al., 2019). A similar pattern was observed in the CS-born infants that was mitigated by the FMT (FIG. 1i).

The mothers were carefully selected for their suitability to serve as donors for their own to-be-born infants using established and newly developed criteria, from which the carrier state of GBS was a counter-selective parameter. Using a healthy non-GBS carrying donor for the CS-born infants of the excluded mothers was refrained from. However, such allotransplantation of fecal microbiota could be considered, i.e., a composition comprising *Bacteroides* strains and/or Bifidobacteria. The FMT procedure was developed by using human milk as a delivery system and inoculated the first milk that was offered to the CS-born infant. This is based on the concept that fecal-oral microbiota transfer is a normal way of vertical microbiota transmission (Zoetendal et al., 2001, Sakwinska et al., 2017). Moreover, it capitalizes on recent studies indicating the role of breast-feeding in the mother to infant microbiota transmission (Pannaraj et al., 2017) and the presence in mothers' milk of a significant number of culturable cells or their DNA that derive from species found in the human gut (Schwab et al., 2019; Asnicar et al., 2018). Finally, for simplicity reasons, a single transfer was used with diluted fecal microbiota corresponding to 3.5 or 7 mg of the transplant ($10^6$-$10^7$ viable cells). Whether the higher dose was associated with the temporally elevated CRP values of the infant M6 cannot be ascertained, but this pilot study shows that the lower dose is effective and did not cause deleterious effects in the infants treated. The transplant used was found to contain on average $7\times10^6$ viable bacterial cells with numbers and variations that are in line with what can be expected of diluted adult fecal microbiota. It has been well established that most women experience some degree of bowel movement during labor. This would provide a potential route of seeding that may have been more manifest when hygiene measures were not as strict as presently in the Western world. It is noteworthy to mention that a day of fasting or anal lavage preceding vaginal birth is practiced in some countries. It would be of interest to determine whether this also affects mother-to-baby microbiota transfer in vaginally-delivered infants.

In this proof-of-principle study, a fresh fecal sample was taken when the mother was at ease during a scheduled study visit 3 weeks prior to delivery in order to rapidly process the transplant and enable pathogen screening in the actual transplant. During screening, it was found that 10 of the 17 pregnant mothers showed properties that may eliminate their use as donor. A total of 29% (5/17) screened positive for pathogenic microbes, four for GBS and one for herpes. In addition, a single case of suspected hepatitis was found. Moreover, 3 other pregnant mothers may not qualify for other reasons related to the position of the fetus. No significant differences were found in microbiota composition between the transplant sample and that of fecal sample of the mothers taken within 3 days before delivery (Mother B). However, it was clearly demonstrated that the infant gut is a highly selective environment as the microbial composition of the single maternal transplant changed dramatically after 2 days and beyond. The temporal development of the newborn infant microbiota has been attributed to choreographed colonization by bacterial populations in a view that the human body is continuously sampling the pool of available colonists.

However, it was shown here that the temporal development in the FMT-CS infants is rather a consequence of selective outgrowth of a fecal maternal inoculum. It has to be determined whether in vaginally born infants the normal seeding is also a single large inoculation as applied here, or the result of multiple and consecutive transfer events of the maternal microbiota. There are indications that maternal gut microbes gradually colonize CS-born infants in a delayed manner over the first several months of life suggesting that bacterial transfer between family members occurs postnatally as well (Korpela et al., 2018a). Once the maternal inoculum has been transferred, the factors driving the selective pressure may include the fucosylated and other human milk oligosaccharides of the mother's milk as well as other factors yet to be discovered. Some of these factors may show temporal developments since in a recent mouse model it was shown that the seeding moment of the transplant determines the resulting community (Martinez et al., 2018). This all may also contribute to the variations observed in the temporal development of the early life microbiota.

Until now, there have been no safe and effective means of full microbiota restoration in CS-delivered infants. Vaginal microbiota transfer has been suggested as a means to naturalize the section-born infant's gut microbiota (Dominguez-Bello et al., 2016). However, is shown here that vaginal swabbing does not correct the CS-induced microbiota imbalance. Some formulations marketed as probiotics contain Bifidobacteria that may partly normalize the overall microbiota (Korpela et al., 2018c). However, the most dramatic difference between vaginally and CS-delivered infants is the ubiquitous lack of *Bacteroides* spp. in the latter group (Backhed et al., 2015, Korpela and de Vos, 2018). This cannot be restored by administering Bifidobacteria or by a vaginal swab. Therefore, the most natural and cost-effective way to inoculate the term infant gut is to expose the infant to maternal intestinal bacteria as shown in this proof-of-concept study.

Pediatric immune system-related diseases, as well as obesity and metabolic diseases, are increasing in prevalence globally and constitute a significant public health burden. Many such chronic diseases have been associated with CS birth and are likely at least partly due to the abnormal microbiota signals that the infant is exposed to (Stiemsma and Michels, 2018). The gut bacteria are in constant interaction with the host, signaling to the host and influencing metabolic and immunological functions. The microbial signals are considered especially important during early development when the immune system is taking shape. Indeed, mouse experiments indicate that the gut microbiota may influence epigenetic programming (Pan et al., 2018), guide the development of the immune system (Gensollen et al., 2016), and affect growth and energy metabolism (Blanton et al., 2016). Successful restoration of the normal vertical microbiota transfer and subsequent age-associated microbiota development in CS-born infants may thus have widespread consequences on the long-term health of these infants.

Experimental Model and Subject Details

Human Subjects

Recruitment of the mothers-to-be took place after the antenatal visit at 33-34 gestational weeks at the Helsinki University Hospital for the assessment of the method of delivery. The mothers had an uncomplicated pregnancy. Gestational age was calculated from the first day of the mother's last menstrual period and confirmed by ultrasound examination of the fetus during the first trimester according to the national practice.

Potential participants (total of 50) planning CS delivery were initially informed about the study by the personnel at the maternity outpatient clinic of the Women's Hospital (Helsinki University Hospital) and written information was given to all. Interested participants were contacted by the study nurse and informed about the study practicalities in more detail. Those who decided to join the study (total of 17) were visited by the study nurse at home to be consulted further about the study and to answer any questions. Moreover, the possibility to talk with the study physician was given, either through a phone call or by appointment. A written consent was collected during the visit of the study nurse if the mothers fulfilled the eligibility criteria, including a healthy pregnancy and willingness to be subject of elaborate screening of themselves and analysis of their infant. Maternal exclusion criteria included positive GBS status, maternal antibiotic treatment within 3 months of delivery, any travel outside the EU within the last 3 months, multiple pregnancy and cesarean section after the onset of labor. In addition, the mothers were subject to intensive screening for pathogens as detailed below).

Following the pathogen screening and further clinical inspection before the due date, it appeared that 10 of the 17 mothers were ineligible since 4 were positive for GBS, 1 had initially inconclusive results for hepatitis E antigen, 1 had a clinically assessed herpes infection, while 2 infants were born in an emergency operation, 1 infant presented with transient tachypnea of the newborn and in one pregnancy the screening had not been carried out before delivery. Therefore, seven pregnant mothers were selected for the FMT procedure with an average age of 34.9 years.

Prior to the transplantation, all seven mothers (and fathers when available) were met by one of the clinicians (OH or SA) to discuss the practical aspects and potential risks associated with the study, and answer any questions related to the study. In the CS procedure as practiced at the Helsinki Hospital (both for elective and urgent CS delivery) all mothers receive a single intravenous dose of 1.5 g cefuroxime, given 30 to 60 minutes prior to incision.

Two observational cohorts were used for delivering control samples that were collected at the same time points as in the FMT-treated infants. Samples from healthy, term-born, normal-weight breastfed infants that were never exposed to antibiotics, excluding CS-associated antibiotics, were selected to be used as control samples. All samples were processed and analyzed in the same laboratory and the same personnel using the same protocol.

Method Details

Maternal Screening

At 3 weeks before the planned CS delivery, a fresh fecal sample was collected and a blood sample of 5 mL was taken from the recruited mothers. As the experiments were performed in the pre-COVID19 times, the blood samples were screened for the presence of human immunodeficiency virus, human T-cell lymphotropic virus, Treponema pallidum, and hepatitis A, B, C and E. Their fecal samples were analyzed for the presence of protozoa and helminths, Entamoeba histolytica, Clostridium difficile, enteric pathogens (Salmonella, Shigella, Campylobacter, Vibrio cholerae, pathogenic Escherichia coli strains EHEC, ETEC, EPEC, EIEC, EAEC), Helicobacter pylori, norovirus, Giardia lamblia, Cryptosporidium parvum, methicillin-resistant Staphylococcus aureus (MRSA), Gram-negative multidrug-resistant (MDR) bacteria and vancomycin-resistant enterococci (VRE). This screening was performed using standard serological tests for Helicobacter pylori, Entamoeba histolytica, Giardia lamblia and Cryptosporidium spp. while all other pathogens were detected using nucleic acid-based PCR or RT-PCR assays at the Helsinki University Hospital Laboratory (HUSLAB, Helsinki, Finland). Except for EAEC, EIEC, EPEC and ETEC, culture-based methods were used for further typing in cases of any positive findings. The presence of MRSA, MDR bacteria and VRE were tested by culturing on specific plates but none of the samples tested positive. In addition, the presence of group B streptococci (GBS) in perianal and cervical swabs was assayed by PCR in the first five mothers (infants M1-M5) and by culture in all consecutive mothers.

The fresh fecal sample of each mother taken 3 weeks before the planned C-section was further processed within 5 hours of donation by dissolving 100 mg in 15 mL of isotonic saline containing 10% glycerol (pharmaceutical grade), and frozen at −80° C. until delivery (Transplant). Viable counts of this preparation were determined by plating on Fastidious Anaerobic Agar and colonies were scored after 7 days of anaerobic incubation at 37° C. An aliquot of 100 mg was also immediately frozen at −80° C. and used for DNA isolation (Mother A sample). Another fecal sample of the mothers was taken 1-3 days prior to delivery and used for DNA isolation (Mother B sample).

For the FMT procedure, the Transplant sample was thawed in the morning of the elective CS, and 1.0 mL was mixed with mother's own milk obtained before the CS and if needed pasteurized bank milk to a total volume of 10 ml.

A sample (10 ml for infant M2 and 5 mL for all other infants) was administered in the first feeding of the infant within 2 h of birth. Mixing own milk and bank milk for the first feeding of the newborn is common practice in the Helsinki birth clinics and is applied to neonates if the maternal milk supply is not sufficient, most typically after elective CS.

The infants were followed after delivery according to the normal clinical routine including determination of the APGAR score. In addition, temperature measurements took place every 6 hours and complete blood counts and C-reactive protein (CRP) levels were determined at 2 days of age, and the meconium and fecal sample at 2 days of age were preserved in the hospital ward first by freezing at −20° C. and subsequently stored at −80° C. in the research lab. After discharge, fecal samples were gathered weekly at home for the first 4 weeks and again at 3 months of age. These samples were immediately frozen at −20° C. in the home freezer and transferred in frozen form in containers to the research laboratory where they were stored at −80° C. until use for DNA extraction. A follow-up visit took place at 4 weeks of age, during which a pediatrician performed a clinical examination of the infant, documented the use of vitamin D supplementation and any probiotics, and received the collected fecal samples. At three months of age the families met with the study nurse, who collected the 3-month fecal sample and documented information on weight and height gain, further probiotic use, and vaccinations according to the routine follow-up schedule at the well-baby-clinic. All infants were breast-fed for three months, except for infant M17 who started formula feeding at the age of 2 months.

Except for one infant (M6), all infants received probiotics from the age of 2-4 weeks (predominantly Lactobacillus reuteri) but in all cases after the 2-week fecal sample had been donated or later. All infants received vitamin D from the age of two weeks as recommended by the Finnish National Welfare Institute. Rotavirus vaccine was administered to all but for infant M8 at 2 and 3 months of age. Infant M6 was presented with inguinal hernia, which was surgically operated at 76 days of age. Comparative microbiota analyses (see below) were performed with fecal samples, collected and processed as described above, from non-treated CS- and vaginally delivered infants. The probiotic use of these infants had been recorded and included the use of Lactobacillus reuteri. The control infants or their lactating mothers did not use any antibiotics during the follow-up period.

DNA Extraction and Microbiota Analysis

DNA was extracted from the fecal samples, 16S rRNA amplicons were generated and subjected to Illumina MiSeq sequencing as previously described (Korpela et al., 2018b).

Briefly, fecal DNA was extracted by repeated bead beating and processed for sequencing using primers 341F and 785R as described in Korpela et al., 2018b. The V3-V4 amplicons were equipped with Illumina TruSeq dual index primers (PE-121-1003) and sequenced with Illumina MiSeq using 2×300 bp reads and a MiSeq v3 reagent kit (MS-102-3003) with 5% PhiX as spike-in (Illumina). The DNA sequences were processed and analyzed using the R-package mare (Korpela et al., 2016), which uses usearch for read processing, and taxonomic annotation (Edgar, 2010). DNA extractions and MiSeq runs were processed in a time frame of 12 months and included internal reference samples and a mock community (Ramiro-Garcia et al., 2016). The latter samples showed highly similar results (R2<3%, P≥0.5 for run ID in PERMANOVA; Pearson correlation coefficient above 87%). The Silva database was used for taxonomic annotation (Quast et al., 2013).

The data analysis was done without rarefaction or transformations, instead the number of reads was used as an offset in all statistical models (Korpela et al., 2018b).

Quantification and Statistical Analysis

Statistical analysis was done using the R package mare (Korpela et al., 2016). PCoA was conducted using Bray-Curtis dissimilarity as the distance measure and calculated with the capscale function of R the package vegan and the Bray-Curtis dissimilarities with function vegdist of the same package (Oksanen et al., 2016). Comparison of the relative abundance of bacterial genera between the groups at each time point was performed using the GroupTest function of the mare package. This function selects the most optimal model for each taxon, depending on its distribution, using either the glm.nb function from the MASS package (Venables & Ripley 2002) or the gls function from the nlme package (Pinheiro et al., 2016). The GroupTest function tests whether the model is appropriate for each taxon separately and if not, attempts to find a suitable model. If no model is found, where the data meet the model assumptions, no p-value is reported. The read counts for each taxon and sample were modelled as a function of delivery group, using the total read count per sample as the offset in the model. In the statistical testing, the vaginally born group was used as the reference group, and tests were performed to ascertain the significance of the microbiota differences between the vaginally born reference group and the FMT-treated and non-treated CS-born groups at ages 1, 3, and 12 weeks. The tests were adjusted for probiotic use. Standard Benjamini-Hochberg corrections for FDR were applied as included in the R-package mare (Korpela et al., 2016). FDR-corrected p-values <0.05 were considered statistically significant.

Example 2

In neonates, microbiota composition differs between antibiotic-treated and non-treated infants (Tanaka et al., 2009; Fouhy et al., 2012). Antibiotic use in neonates thus disturbs microbiota development, which is comparable to the microbiota disturbance observed in CS-born infants as compared to vaginally born infants.

In Finland, the Social Insurance Institute maintains a national database on prescription drug purchases and eligibility for special reimbursement due to chronic diseases linked with personal identification information of the patient (Furu et al., 2010). This unique database together with pyrosequencing of fecal microbiomes was used to investigate the short- and long-term effects of antibiotics on health (Korpela et al., 2016).

It was found that antibiotic use in childhood is associated with marked changes in the intestinal microbiota composition, which persist for at least 6 months. Macrolides, particularly, appear to modify the microbiota and their functions, being the strongest driver of inter-individual differences in microbiota composition in the cohort. Among the children who received macrolides in early life, a positive correlation was found with body mass index (BMI), as well as an increased risk of asthma, suggesting that altered microbiota composition in infants predisposes to weight gain and asthma in later life (Korpela et al., 2016).

Results

Macrolide Use Associated with Asthma and Overweight

Early-life antibiotic use is associated with health outcomes. Current or developing asthma was significantly positively associated with frequent macrolide use during the first 2 years of life: odds ratio for the group that received >2 macrolide courses (N=32) compared with the non-exposed (N=116) was 6.11 (95% confidence interval: 1.53-26.58, P=0.004 in Fisher's test). A strong correlation was observed between antibiotic use and the BMI z-score in the children with >2 macrolide courses before the age of 2 years, but not in the non-exposed children (Korpela et al., 2016).

Discussion

Clear differences were observed in the microbiota compositions of the antibiotic-treated children as compared with those who were not exposed to antibiotics for >2 years. Some aspects of the microbiota, such as the abundance of *Bifidobacterium* and *Bacteroides*, and macrolide resistance, normalized within 12 months after a macrolide course (Korpela et al., 2016).

In an earlier mouse study, it was shown that although the microbiota recover when antibiotic administration is ceased, the metabolic changes persist (Cox et al., 2014). The results confirm corresponding patterns in human children: the children with heavy early-life use of antibiotics but no antibiotics for at least 2 years before sample donation had a microbiota similar to those with low lifetime antibiotic use. Nevertheless, early-life use of macrolides predisposed to overweight and asthma. These results suggest that even transient microbiome disturbance in early life may have long-term effects on the metabolic and immunological health of the child. A strong positive association was found between recorded antibiotic use and BMI z-scores, specifically in a group of children that were exposed to macrolides in early life (Korpela et al., 2016).

Bile acid metabolism is one of the key functions performed by the intestinal bacteria, with strong effects on host energy metabolism. Modified bile acids function as metabolic regulators, and bile-salt hydrolase activity of the microbiota has been shown to reduce host weigh gain, insulin resistance and blood cholesterol via FXR-a and TGR5 signaling (Joyce et al., 2014; Smet et al., 1998).

Increased risk of allergic disease has been associated with deviations in the microbiota characteristics in early life, such as depletion of *Lactobacillus* and/or *Bifidobacterium* (Sepp et al., 2005; Mah et al., 2006; Sjogren et al., 2009).

All of these characteristics were present in the recently macrolide-treated children in the cohort, suggesting that macrolide use alters the microbiota in a way that disrupts the healthy immune system development (e.g., as measured by increase in secretory IgA and/or increase in antimicrobial peptides in the intestine). Furthermore, other factors, which alter the microbiota in a similar manner, such as Caesarean section, lack of breastfeeding and pre- and perinatal stress, predispose to asthma (Azad et al., 2012).

A specific case is the 10-fold increased levels of Eggerthella spp. observed after macrolide exposure. Most Eggerthella spp. are pathogens and may promote an inflammatory response. Experimental evidence from animal models shows that antibiotics in early life disrupt the microbiota and thereby the development of the immune system, leading to airway hyper-responsiveness in susceptible individuals (Russell et al., 2012; Noverr et al., 2004). To conclude, macrolide use is associated with microbiota characteristics that have previously been associated with the risk of immunological and metabolic diseases, as well as obesity. Furthermore, macrolide use promoted a marked increase in macrolide resistance of the microbiota. The results confirm and extend previous results from mouse experiments (Cox et al., 2014) and indicate that microbiota aberrations due to antibiotic us or CS may have undesired effects on the developing microbiota of children, which may compromise the development of a healthy immune system and metabolism (Korpela et al., 2016).

Similar results have been observed in other studies where, for example, it was shown that antibiotic use in early life affecting microbiota development may impede immune response to vaccines. See, for example, Harris et al., 2018 and Harris et al., 2017.

Methods

Study cohort consisted of 236 Finnish children, attending the same day-care centers at the time of the study. Register-based information and full background information was available for all children; 142 children donated fecal samples. The children were part of a larger cohort originally recruited for a probiotic trial. The children attended a health check in the beginning of the study, during which weight and height were measured. Based on the weight and height, BMI z-scores were calculated according to the LMS parameters obtained from the Centers of Disease Control and Prevention (Korpela et al., 2016).

In Finland, antibiotics are only available by prescription. Information on antibiotic purchases was obtained from the records of the Finnish Social Insurance Institution, which subsidizes health-care costs. Data was collected on all antibiotics purchased for the study children from the date of birth to the date of donation of the last fecal sample. Individuals with chronic illnesses are eligible for special reimbursement of their drug purchases, and the eligibility information is stored in the national database.

Associations between health and antibiotic use were analyzed using the full cohort of 236 children. Associations between antibiotic use and BMI z-score were assessed using Pearson correlations. Associations between antibiotic use during the first 2 years of life and asthma (N=15), and allergic dermatitis (N=5) were assessed using the Fisher's test. Processing of the fecal samples (Korpela et al., 2016). The fecal samples were collected at home and transported immediately to the study center for storage in 70° C. DNA was extracted from the fecal samples using the Promega Wizard Genomic DNA Purification Kit as described (Ahlroos et al., 2009). Concentration of DNA was measured with NanoDrop and adjusted to 10 ng ml 1. Sequencing. Bacterial composition was investigated using 454 Titanium sequencing of the V4-V6 region of the 16S rRNA gene (primers S-D-Bact-0564-aS-15/S and Univ-1100-a-A-15 that have been recommended for pyrosequencing, Klindworth et al., 2013).

Example 3

A relationship between the dose as administered to the infant and the infant's level of C-Reactive Protein (CRP) level was identified. A high C-reactive protein (CRP) level, in comparison to healthy individuals, may indicate an increased level of inflammation.

REFERENCES

Abrahamsson T. R., Jakobsson H. E., Andersson A. F., Bjorksten B., Engstrand L., Jenmalm M. C. (2012): Low diversity of the gut microbiota in infants with atopic eczema. *J. Allergy Clin. Immunol.* 129:434-40.

Ahlroos, T. & Tynkkynen, S. Quantitative strain-specific detection of *Lactobacillus rhamnosus* GG in human faecal samples by real-time PCR. J. Appl. Microbiol. 106, 506-514 (2009).

Andersen V., Moller S., Jensen P. B., Moller F. T., Green A. (2020). Caesarean delivery and risk of chronic inflammatory diseases (Inflammatory Bowel Disease, Rheumatoid Arthritis, Coeliac Disease, and Diabetes Mellitus): A population-based registry study of 2,699,479 births in Denmark during 1973-2016. *Clin. Epidemiol.* 12:287-293.

Asnicar F., Manara S., Zolfo M., Truong D. T., Scholz M., Armanini F., Ferretti P., Gorfer V., Pedrotti A., Tett A., and Segata N. (2018). Studying vertical microbiome transmission from mothers to infants by strain-level metagenomic profiling. *mSystems* 17:2(1).

Azad, M. B. & Kozyrskyj, A. L. Perinatal programming of asthma: the role of gut microbiota. Clin. Dev. Immunol. 2012, 932072 (2012).

Backhed F., Roswall J., Peng Y., Feng Q., Jia H., Kovatcheva-Datchary P., Li Y., Xia Y., Xie H., Zhong H., Khan M. T., Zhang J., Li J., Xiao L., Al-Aama J., Zhang D., Lee Y. S., Kotowska D., Colding C., Tremaroli V., Yin Y., Bergman S., Xu X., Madsen L., Kristiansen K., Dahlgren J., and Wang J. (2015). Dynamics and stabilization of the human gut microbiome during the first year of life. *Cell Host Microbe* 17:852.

Blaser M. J. (2017). The theory of disappearing microbiota and the epidemics of chronic diseases. *Nat. Rev. Immunol.* 27:461-463.

Blanton L. V., Charbonneau M. R., Salih T., Barratt M. J., Venkatesh S., Ilkaveya O., Subramanian S., Manary M. J., Trehan I., Jorgensen J. M., Fan Y. M., Henrissat B., Leyn S. A., Rodionov D. A., Osterman A. L., Maleta K. M., Newgard C. B., Ashorn P., Dewey K. G., and Gordon J. I. (2016). Gut bacteria that prevent growth impairments transmitted by microbiota from malnourished children. *Science* 351(6275) aad3311.

Chen, J., Yu, Z., Michel, Jr. F. C., Wittum, T. & Morrison, M. Development and application of real-time PCR assays for quantification of erm genes conferring resistance to macrolides-lincosamides-streptogramin B in livestock

| Dose fecal matter (mg) | C-Reactive Protein (CRP) level | Normal intestinal colonization, reduction of *Enterococcus* species and *Klebsiella* species | Increased level of intestinal secretory IgA and increased level of antimicrobial peptides | Increased immune response to vaccines |
|---|---|---|---|---|
| 0.5 (from mother) | Normal | V | V | V |
| 1 (from grandfather) | Normal | V | V | V |
| 1.5 (from mother) | Normal | V | V | V |
| 2 (from sibling) | Normal | V | V | V |
| 2.5 (from father) | Normal | V | V | V |
| 2.9 (from mother) | Normal | V | V | V |
| 4 (from grandfather) | High | V | V | V |
| 5 (from mother) | High | V | V | V |
| 6 (from sibling) | High | V | V | V |
| 7 (from father) | High | V | V | V | manure and manure management systems. Appl. Environ. Microbiol. 73:4407-4416 (2007).

Chu D. M., Ma J., Prince A. L., Antony K. M., Seferovic M. D., Aagaard K. M. (2017). Maturation of the infant microbiome community structure and function across multiple body sites and in relation to mode of delivery. *Nature Med.* 23:314-326.

Collado et al. Appl. Environ. Microbiol. 2007 December; 73(23):7767-70.

Cox, L. M. et al. Altering the intestinal microbiota during a critical developmental window has lasting metabolic consequences. Cell 158:705-721 (2014).

Dominguez-Bello M. G., De Jesus-Laboy K. M., Shen N., Cox L. M., Amir A., Gonzalez A., Bokulich N. A., Song S. J., Hoashi M., Rivera-Vinas J. I., Mendez K., Knight R., and Clemente J. C. (2016). Partial restoration of the microbiota of cesarean-born infants via vaginal microbial transfer. *Nature Med.* 22:250-3.

Edgar R. C. (2010). Search and clustering orders of magnitude faster than BLAST, *Bioinformatics* 26:2460-2461.

Fouhy F., Guinane C. M., Hussey S., Wall R., Ryan C. A., Dempsey E. M., Murphy B., Ross R. P., Fitzgerald G. F., Stanton C., Cotter P. D. (2012). High-throughput sequencing reveals the incomplete, short-term recovery of infant gut microbiota following parenteral antibiotic treatment with ampicillin and gentamicin. *Antimicrob. Agents Chemother.* 56:5811-5820.

Furu, K. et al. The Nordic countries as a cohort for pharmacoepidemiological research. Basic Clin. Pharmacol. Toxicol. 106:86-94 (2010).

Gensollen T., Iyer S. S., Kasper D. L., and Blumberg R. S. (2016). How colonization by microbiota in early life shapes the immune system. *Science* 352, 539-544.

Harris et al., 2017. J. Infect. Dis. 2017 Jan. 1; 215(1):34-41.

Harris et al., 2018. Cell Host Microbe. 2018 Aug. 8; 24(2): 197-207.e4.

Helve et al. (2019) 2843. Maternal Fecal Transplantation to Infants Born by Cesarean Section: Safety and Feasibility. *Open Forum Infect. Dis.* 2019 October; 6(Suppl 2): S68.

Hill C. J., Lynch D. B., Murphy K., Ulaszewska M., Jeffery I. B., O'Shea C. A., Watkins C., Dempsey E., Mattivi F., Tuohy K., Ross R. P., Ryan C. A., O'Toole P. W., and Stanton C. (2017). Evolution of gut microbiota composition from birth to 24 weeks in the INFANTMET cohort. *Microbiome* 5:4.

Jakobsson H. E., Abrahamsson T. R., Jenmalm M. C., Harris K., Quince C., Jernberg C., Bjorksten B., Engstrand L., Andersson A. F. (2014): Decreased gut microbiota diversity, delayed Bacteroidetes colonisation and reduced Th1 responses in infants delivered by caesarean section. *Gut* 63:559-566.

Joyce, S. A. et al. Regulation of host weight gain and lipid metabolism by bacterial bile acid modification in the gut. Proc. Natl. Acad. Sci. USA 111:7421-7426 (2014).

Keag O. E., Norman J. E., and Stock S. J. (2018). Long-term risks and benefits associated with cesarean delivery for mother, baby, and subsequent pregnancies: Systematic review and meta-analysis. *PLoS Med.* 23:e1002494.

Klindworth, A. et al. Evaluation of general 16S ribosomal RNA gene PCR primers for classical and next-generation sequencing-based diversity studies. Nucleic Acids Res. 41, e1 (2013).

Kostic A. D., Gevers D., Siljander H., Vatanen T., Hyoty-lainen T., Hämäläinen A., Peet A., Tillmann V., Pöhö P., Mattila I. (2015): The dynamics of the human infant gut microbiome in development and in progression toward type 1 diabetes. *Cell Host Microbe* 17:260-273.

Korpela K., Salonen A., Virta L. J., Kekkonen R. A., Forslund K., Bork P., and de Vos W. M. (2016). Intestinal microbiome is related to lifetime antibiotic use in Finnish pre-school children. *Nature Comm.* 7:10410.

Korpela K., Zijlmans M., Kuitunen M., Kukkonen K., Savilahti E., Salonen A., de Weerth C., de Vos W. M. (2017). Childhood BMI in relation to microbiota in infancy and lifetime antibiotic use. *Microbiome* 5:26.

Korpela K. and de Vos W. M. (2018). Early life colonization of the human gut: microbes matter everywhere. *Curr. Opin. Microbiol.* 44:70-78.

Korpela K., Costea P., Coelho L. P., Kandels-Lewis S., Willemsen G., Boomsma D. I., Segata N., and Bork P. (2018a). Selective maternal seeding and environment shape the human gut microbiome. *Genome Res.* 28:561-568.

Korpela K., Salonen A., Hickman B., Kunz C., Sprenger N., Kukkonen K., Savilahti E., Kuitunen M., and de Vos W. M. (2018b). Fucosylated oligosaccharides in mother's milk alleviate the effects of caesarean birth on infant gut microbiota. *Sci. Rep.* 13:13757.

Mah, K. W. et al. Distinct pattern of commensal gut microbiota in toddlers with eczema. Int. Arch. Allergy Immunol. 140:157-163 (2006).

Martínez I., Maldonado-Gomez M. X., Gomes-Neto J. C., Kittana H., Ding H., Schmaltz R., Joglekar P., Cardona R. J., Marsteller N. L., Kembel S. W., Benson A. K., Peterson D. A., RamerTait A. E., and Walter J. (2018). Experimental evaluation of the importance of colonization history in early-life gut microbiota assembly. *Elife* 18:e36521.

Nagpal R., Tsuji H., Takahashi T., Nomoto K., Kawashima K., Nagata S., Yamashiro Y. (2017). Ontogenesis of the gut microbiota composition in healthy, full-term, vaginally born and breast-fed infants over the first 3 years of life: A quantitative bird's-eye view. *Front. Microbiol.* 8:1388.

Noverr, M. C., Noggle, R. M., Toews, G. B. & Huffnagle, G. B. Role of antibiotics and fungal microbiota in driving pulmonary allergic responses. *Infect. Immun.* 72, 4996-5003 (2004).

Oksanen J., Blanchet F. G., Friendly M., Kindt R., Legendre P., McGlinn D., Minchin P. R., O'Hara R. B., Simpson G. L., Solymos P., Stevens M. H. H., Szoecs E. and Wagner H. (2016). vegan: Community Ecology Package. R package version 2.4-0 (2016) CRAN.Rproject.org/package=vegan.

Pan W. H., Sommer F., Falk-Paulsen M., Ulas T., Best P., Fazio A., Kachroo P., Luzius A., Jentzsch M., Rehman A., Müller F., Lengauer T., Walter J., Künzel S., Baines J. F., Schreiber S., Franke A., Schultze J. L., Backhed F., and Rosenstiel P. (2018). Exposure to the gut microbiota drives distinct methylome and transcriptome changes in intestinal epithelial cells during postnatal development. *Genome Med.* 13:27.

Pannaraj P. S., Li F., Cerini C., Bender J. M., Yang S., Rollie A., Adisetiyo H., Zabih S., Lincez P. J., Bittinger K., Bailey A., Bushman F. D., Sleasman J. W., and Aldrovandi G. M. (2017). Association between breast milk bacterial communities and establishment and development of the infant gut microbiome. *JAMA Pediatr.* 171: 647-654.

Pinheiro J., Bates D., DebRoy S., Sarkar D. and R Core Team (2016). nlme: Linear and Nonlinear Mixed Effects Models. R package version 3.1-128 (2016) CRAN.Rproject.org/package=nlme>.

Ramiro-Garcia J., Hermes G. D. A., Giatsis C., Sipkema D., Zoetendal E. G., Schaap P. J., and Smidt (2016). NG-Tax, a highly accurate and validated pipeline for analysis of 16S rRNA amplicons from complex biomes. F1000Res. 5:1791.

Russell, S. L. et al. Early life antibiotic-driven changes in microbiota enhance susceptibility to allergic asthma. *EMBO Rep.* 13:440-447 (2012).

Schwab C., E. Voney, A. Ramirez Garcia, M. Vischer & C. Lacroix (2019). Characterization of the cultivable microbiota in fresh and stored mature human breast milk. Front Microbiol. 10: 2666.

Sepp, E., Julge, K., Mikelsaar, M. & Bjorksten, B. Intestinal microbiota and immunoglobulin E responses in 5-year-old Estonian children. Clin. Exp. Allergy 35:1141-1146 (2005).

Smet, I. D., Boever, P. D. & Verstraete, W. Cholesterol lowering in pigs through enhanced bacterial bile salt hydrolase activity. Br. J. Nutr. 79:185-194 (1998).

Sjogren, Y. M., Jenmalm, M. C., Bottcher, M. F., Bjorksten, B. & SverremarkEkstrom, E. Altered early infant gut microbiota in children developing allergy up to 5 years of age. Clin. Exp. Allergy 39:518-526 (2009).

Quast C., Pruesse E., Yilmaz P., Gerken J., Schweer T., Yarza P., Peplies J., and Glöckner F. O. (2013). The SILVA ribosomal RNA gene database project: improved data processing and web-based tools. *Nucl. Acids Res.* 41:D590-D596.

Sakwinska O., Foata F., Berger B., Brüssow H., Combremont S., Mercenier A., Dogra S., Soh S. E., Yen J. C. K., Heong G. Y. S., Lee Y. S., Yap F., Meaney M. J., Chong Y. S., Godfrey K. M., and Holbrook J. D. (2017). Does the maternal vaginal microbiota play a role in seeding the microbiota of neonatal gut and nose? *Benef Microbes* 13:763-778.

Sevelsted A., Stokholm J., Bønnelykke K., and Bisgaard H. (2015). Cesarean section and chronic immune disorders. *Pediatrics* 135:e92-8.

Shao Y., Forster S. C., Tsaliki E., Vervier K., Strang A., Simpson N., Kumar N., Stares M. D., Rodger A., Brocklehurst P., Field N., and Lawley T. D. (2019). Stunted microbiota and opportunistic pathogen colonization in caesarean-section birth. Nature 574:117-121.

Stiemsma L. T. and Michels K. B. (2018). The role of the microbiome in the developmental origins of health and disease. *Pediatrics* 141:e20172437.

Tanaka, S. et al. Influence of antibiotic exposure in the early postnatal period on the development of intestinal microbiota. FEMS Immunol. Med. Microbiol. 56:80-87 (2009).

Tun H. M., Konya T., Takaro T. K., Brook J. R., Chari R., Field C. J., Guttman D. S., Becker A. B., Mandhane P. J., Turvey S. E. (2017). Exposure to household furry pets influences the gut microbiota of infants at 3-4 months following various birth scenarios. *Microbiome* 5:40.

Venables, W. N. & Ripley, B. D. (2002). Modern Applied Statistics with S. Fourth Edition. Springer, New York. ISBN 0-387-95457-0.

Yap G. C., Loo E. X. L., Aw M., Lu Q., Shek L. P., Lee B. W. (2014). Molecular analysis of infant fecal microbiota in an Asian at-risk cohort-correlates with infant and childhood eczema. *BMC Res. Notes* 7:166.

Zijlmans M. A., Korpela K., Riksen-Walraven J. M., de Vos W. M., de Weerth C. (2015). Maternal prenatal stress is associated with the infant intestinal microbiota. *Psychoneuroendocrinology* 53:233-245.

Zoetendal E. G., Akkermans A. D. L., Akkermans-van Vliet W., de Visser J. A. and de Vos, W. M. (2001). The host genotype affects the bacterial community in the human gastrointestinal tract. *Microbial. Ecol. Health & Dis.* 13:129-134.

The invention claimed is:

1. A method of increasing immune response to a vaccine in a Cesarean section- (CS-) born infant, the method comprising:

administering to the CS-born infant a composition comprising:
(a) at least one *Bacteroides* species; and
(b) at least one *Bifidobacterium* species,
in combination with administering to the CS-born infant a vaccine, wherein the composition increases the infant's immune response to the vaccine.

2. The method according to claim 1, wherein the composition comprises at least one *Akkermansia* species.

3. The method according to claim 2, wherein the vaccine is a vaccine against invasive disease caused by *Streptococcus pneumoniae*.

4. The method according to claim 1, wherein the method reduces intestinal colonization of pathogenic microorganisms selected from the group consisting of *Enterococcus* species, *Enterococcus faecium*, *Enterococcus faecalis*, *Enterobacter* species, *Enterobacter cloacae*, *Klebsiella* species, *Klebsiella pneumonia*, *Klebsiella oxytoca*, *Haemophilus influenza*, *Campylobacter jejuni*, and *Salmonella enterica*.

5. The method according to claim 1, wherein the method increases intestinal relative abundance of *Bacteroides* species and/or increases intestinal relative abundance of *Bifidobacterium* species and/or decreases intestinal relative abundance of *Clostridium* species.

6. The method according to claim 1, wherein the method reduces susceptibility to a disorder selected from the group consisting of metabolic or immune disease, obesity, type 2 diabetes, chronic inflammatory disease, inflammatory bowel disease, Crohn's disease, ulcerative colitis, irritable bowel syndrome, auto-immune disease, type 1 diabetes, rheumatoid autoimmune disease, rheumatoid arthritis, Bechterew's disease, thyroid autoimmune disease, Hashimoto's disease, Graves' disease, Addison's disease, psoriasis, vitiligo, celiac disease, systemic connective disorder, systemic lupus erythematosus, atopy-related disease, allergy, and asthma.

7. The method according to claim 1, wherein the method increases levels of intestinal secretory IgA and/or increases levels of intestinal antimicrobial peptides.

8. The method according to claim 1, wherein the method increases intestinal microbial diversity as may be measured by increased inverse Simpson diversity index.

9. The method according to claim 1, wherein the composition is fecal matter obtained from at least one donor subject.

10. The method according to claim 9, wherein the at least one donor subject is the CS-born infant's mother.

11. The method according to claim 10, wherein the fecal matter is obtained from the mother of the CS-born infant at most five (5) weeks prior to the CS.

12. The method according to claim 10, wherein the fecal matter is obtained from the mother of the CS-born infant at most three (3) weeks prior to the CS.

13. The method according to claim 9, wherein the method includes:

determining in a sample of one or more subjects of one or more of group B *Streptococcus*, human immunodeficiency virus (HIV), SARS-COV-2 (COVID-19), human T-cell lymphotropic virus, *Treponema pallidum; Treponema pallidum*, hepatitis A, B, C, and E, proto-zoa, helminths, *Entamoeba histolytica*, *Clostridium difficile*, enteric pathogens, *Salmonella*, *Shigella*, *Campylobacter*, *Vibrio cholera*, pathogenic *Escherichia coli* strains, EHEC, ETEC, EPEC, EIEC, EAEC, *Helicobacter pylori*, Norovirus, *Giardia lamblia*, *Cryptosporidium parvum*, methicillin-resistant *Staphylococcus aureus* (MRSA), Gram-negative multidrug-resistant (MDR) bacteria and vancomycin-resistant enterococci (VRE); and subsequent selection of one or more donor subjects not carrying one or more of group B *Streptococcus*, human immunodeficiency virus (HIV), human T-cell lymphotropic virus, *Treponema pallidum*, hepatitis A, B, C, and E, protozoa, helminths, *Entamoeba histolytica*, *Clostridium difficile*, enteric pathogens, *Salmonella*, *Shigella*, *Campylobacter*, *Vibrio cholera*, pathogenic *Escherichia coli* strains, EHEC, ETEC, EPEC, EIEC, EAEC, *Helicobacter pylori*, Norovirus, *Giardia lamblia*, *Cryptosporidium parvum*, methicillin-resistant *Staphylococcus aureus* (MRSA), Gram-negative multidrug-resistant (MDR) bacteria and vancomycin-resistant enterococci (VRE).

14. The method according to claim 9, wherein the method includes:

determining antibiotic use of one or more subjects; and
subsequent selection of one or more donor subjects not having used antibiotics in the preceding month.

15. The method according to claim 9, wherein the method includes:

determining antibiotic use of one or more subjects; and
selecting one or more donor subjects not having used antibiotics in the preceding six (6) months.

16. The method according to claim 1, wherein the composition comprises between 0.1-5 mg fecal matter and/or wherein the composition comprises between $1\times10^5$ and $1\times10^8$ bacterial cells.

17. The method according to claim 1, wherein the composition comprises between 0.1-2.9 mg fecal matter obtained from the mother, father, grandmother, and/or grandfather of the CS-born infant.

18. The method according to claim 1, wherein the composition is comprised in breast milk or pasteurized bank milk and/or administered to the CS-born infant within, at most, twenty-four (24) hours of CS.

19. The method according to claim 1, wherein the infant is a mammal.

20. The method according to claim 1, wherein the infant is a human.

21. The method according to claim 1, wherein the composition is administered to the CS-born infant within, at most, four (4) hours of CS.

22. The method according to claim 1, wherein the vaccine is a vaccine selected from the group consisting of vaccines against measles, mumps, rubella, diphtheria, tetanus, pertussis, poliomyelitis, *Haemophilus influenzae* type B, human papillomavirus, hepatitis A, influenza, invasive disease caused by *Neisseria meningitidis*, invasive disease caused by *Streptococcus pneumoniae*, rotavirus, tuberculosis, and varicella.

23. The method according to claim 1, wherein the increased immune response to the vaccine is as measured by increased level of antigen specific antibodies in a blood sample of the CS-born infant.

*     *     *     *     *